(12) United States Patent
Wackett et al.

(10) Patent No.: US 6,265,201 B1
(45) Date of Patent: Jul. 24, 2001

(54) DNA MOLECULES AND PROTEIN DISPLAYING IMPROVED TRIAZINE COMPOUND DEGRADING ABILITY

(75) Inventors: Lawrence P. Wackett, St. Paul; Michael J. Sadowsky, Roseville; Mervyn L. de Souza, St. Paul, all of MN (US); Jeremy S. Minshull, Menlo Park, CA (US)

(73) Assignees: Regents of the University of Minnesota, Minneapolis, MN (US); Maxygen Inc., Redwood City, CA (US)

( * ) Notice: Subject to any disclaimer, the term of this patent is extended or adjusted under 35 U.S.C. 154(b) by 0 days.

(21) Appl. No.: 09/155,036

(22) PCT Filed: Jan. 16, 1998

(86) PCT No.: PCT/US98/00944

§ 371 Date: Sep. 17, 1998

§ 102(e) Date: Sep. 17, 1998

(87) PCT Pub. No.: WO98/31816

PCT Pub. Date: Jul. 23, 1998

Related U.S. Application Data

(60) Provisional application No. 60/035,404, filed on Jan. 17, 1997.

(51) Int. Cl.[7] .............................. C07H 21/04; C12N 9/14
(52) U.S. Cl. ................... 435/252.3; 435/69.1; 435/93.1; 435/183; 435/195; 435/320.1; 435/252.33; 536/23.2
(58) Field of Search ................................ 435/69.1, 93.1, 435/183, 195, 252.33, 320.1, 252.3; 536/23.2, 23.1; 530/350

(56) References Cited

U.S. PATENT DOCUMENTS

| | | |
|---|---|---|
| 4,745,064 | 5/1988 | Cook et al. . |
| 5,429,949 | 7/1995 | Radosevich et al. . |
| 5,508,193 | 4/1996 | Mandelbaum . |

FOREIGN PATENT DOCUMENTS

| | | |
|---|---|---|
| 0 141 784 | 5/1985 | (EP) . |
| WO 90/07576 | 7/1990 | (WO) . |
| WO 91/01087 | 2/1991 | (WO) . |
| WO 95/01437 | 1/1995 | (WO) . |
| WO 95/22625 | 8/1995 | (WO) . |
| WO 97/15675 | 5/1997 | (WO) . |

OTHER PUBLICATIONS

Arkin et al., "An algorithm for protein engineering: Simulations of recursive ensemble mutagenesis," *Proc. Natl. Acad. Sci. USA*, 89, 7811–7815 (1992).
Armstrong et al., "Adsorption Catalyzed Chemical Hydolysis of Atrazine," *Environ. Sci. Technol.*, 2, 683–689 (1968).
Bartel et al., "Isolation of New Ribozymes from a Large Pool of Random Sequences," *Science*, 261, 1411–1418 (1993).
Behki et al., "Degradation of Atrazine by Pseudomonas: N–Dealkylation and Dehalogenation of Atrazine and Its Metabolites," *J. Agric. Food Chem.*, 34, 746–749 (1986).
Behki et al., "Metabolism of the Herbicide Atrazine by Rhodococcus Strains," *Appl. Environ. Microbiol.*, 59, 1955–1959 (1993).
Bergmann et al., "Determination of Trace Amounts of Chlorine in Naphtha," *Analytical Chem.*, 29, 241–243 (1957).
Bock et al., "Selection of single–stranded DNA molecules that bind and inhibit human thrombin," *Nature*, 355, 564–566 (1992).
de Bruijin et al., "The use of transposon Tn5 mutagenesis in the rapid generation of correlated physical and genetic maps of DNA segments cloned into multicopy plasmids—a review," *Gene*, 27, 131–149 (1984).
Burchfield et al., "Pyridine–Alkali Reactions in the Analysis of Pesticides Containing Active Halogen Atoms," *Agricultural and Food Chemistry*, 6, 106–110 (1958).
Caldwell et al., "Limits of Diffusion in the Hydrolysis of Substrates by the Phosphotriesterase from Pseudomonas diminuta," *Biochem*, 30, 7438–7444 (1991).
Calogero et al., "In vivo recombination and the production of hybrid genes," *FEMS Microbiology Lett.*, 97, 41–44 (1992).
Caren et al., "Efficient Sampling of Protein Sequence Space for Multiple Mutants," *Bio/Technology*, 12, 517–520 (1994).
Cook, "Biodegradation of s–triazine xenobiotics," *FEMS Microbiol Rev.*, 46, 93–116 (1987).
Cook et al., "s–Triazines as Nitrogen Sources for Bacteria," *J. Agic. Food Chem.*, 29, 1135–1143 (1981).
Cwirla et al., "Peptides on phage: A vast library of peptides for indentifying ligands," *Proc. Natl. Acad. Sci. USA*, 87 6378–6382 (1990).
Delagrave et al., "Searching Sequence Space to Engineer Proteins: Exponential Ensemble Mutagenesis," *Bio/Technology*, 11, 1548–1552 (1993).
Delagrave et al., "Recursive ensemble mutagenesis," *Protein Engineering*, 6, 327–331 (1993).
Eaton et al., "Cloning and Analysis of s–Triazine Catabolic Genes from Pseudomonas sp. Strain NRRLB–12227," *J. Bacteriol.*, 173, 1215–1222 (1991).

(List continued on next page.)

*Primary Examiner*—Rebecca E. Prouty
*Assistant Examiner*—Richard Hutson
(74) *Attorney, Agent, or Firm*—Mueting, Raasch & Gebhardt, P.A.

(57) ABSTRACT

This invention relates to the identification of homologs of atrazine chlorohydrolase and the use of these homologs to degrade s-triazine-containing compounds. In particular, this invention includes the identification of homologs of atrazine chlorohydrolase encoded by a DNA fragment having at least 95% homology to the sequence from the nucleic acid sequence beginning at position 236 and ending at position 1655 of SEQ ID NO:1, where the DNA fragment is capable of hybridizing under stringent conditions to SEQ ID NO:1 and has altered catalytic activity as compared with wild-type atrazine chlorohydrolase.

10 Claims, 16 Drawing Sheets

OTHER PUBLICATIONS

Eaton et al., "Cloning and Comparison of the DNA Encoding Ammelide Aminohydrolase and Cyanuric Acid Amidohydrolase from Three s–Triazine–Degrading Bacteriol Strains," *J. Bacteriol.*, 173, 1362–1366 (1991).

EMBL Database entry TT3ITRA, Accession No. M13165, Jul. 16, 1988, Huang et al., *Gene*, 41, 23–31 (1986).

EMBL Database Entry RCTRZA, Accession No. L16534, Oct. 2, 1993, Shao et al., *J. Bacteriol.*, 177, 5748–5755 (1995).

Epstein, "Estimation of Microquantities of Cyanide," *Analytical Chemistry*, 19, 272–276 (1947).

Erickson et al., "Degradation of atrazine and related s–triazines," *Critical Rev. Environ. Cont.*, 19, 1–13 (1989).

Giardina et al., "4–Amino–2–chloro–1,3,5–triazine: A New Metabolite of Atrazine by a Soil Bacterium," *Agric. Biol. Chem.*, 44, 2067–2072 (1980).

Goldman et al., "An Algorithmically Optimized Combinational Library Screened by Digital Imaging Spectroscopy," *Bio/Technology*, 10, 1557–1561 (1992).

Habig et al., "Assays for Differentiation of Glutathione s–transferases," *Methods in Enzymology*, 77, 398–405 (1981).

Hayashi et al., "Simultaneous Mutagenesis of Antibody CDR Regions by Overlap Extension and PCR," *Biotechniques*, 17, 310–315 (1994).

Hermes et al., "Searching sequence space by definably random mutagensis: Improving the catalytic potency of an enzyme," *Proc. Natl. Acad. Sci. USA*, 87, 696–700 (1990).

Jessee et al., "Anaerobic Degradation of Cyanuric Acid, Cysteine, and Atrazine by a Facultative Anaerobic Bacterium," *Appl. Environ. Microbiol.*, 45, 97–102 (1983).

Leung et al., "A Method for Random Mutagenesis of a Defined DNA Segment using a Modified Polymerase Chain Reaction," *Technique*, 1, 11–15 (1989).

Loos, "Indicator media for microorganisms degrading chlorinated pesticides," *Can. J. Microbiol.*, 21, 104–107 (1975).

Maleki et al., "Degradation of Atrazine by Soil Consortia: Characterization of Enzymatically Active Fractions for Cell––Bound and Cell–Free Enrichment Cultures," *Abstracts of the 95$^{th}$ General Meeting of the American Society for Microbiology*, Abstract No. Q–88, p. 415 (1995).

Mandelbaum et al., "Isolation and Characterization of a Pseudomonas sp. That Mineralizes the s–Triazine Herbicide Atrazine," *Appl. Environ. Microbiol.*, 61, 1451–1457 (1995).

Mandelbaum et al., "Mineralization of the s–Triazine Ring of Atrazine by Stable Bacterial Mixed Cultures," *Appl. Environ. Microbiol.*, 59, 1695–1701 (1993).

Mandelbaum et al., "Rapid Hydrolysis of Atrazine to Hydroxyatrazine by Soil Bacteria," *Environ. Sci. Technol.*, 27, 1943–1946 (1993).

Maniatis et al., *Molecular Cloning: A Laboratory Manual*, Cold Spring Harbor Press, Cold Spring Harbor, NY, title page and table of contents (1989).

Marton et al., "DNA nicking favors PCR recombination," *Nucl. Acids Res.*, 19, 2423–2426 (1991).

McCafferty et al., "Phage antibodies: filamentous phage displaying antibody variable domains," *Nature*, 348, 552–554 (1990).

Meyerhans et al., "DNA recombination during PCR," *Nucl. Acids Res.*, 18, 1687–1691 (1990).

Minshull et al., "Metabolic Pathway Engineering by Directed Evolution," abstract, Biodegradation of Organic Pollutants, UIB–GBF–CSIC–TUB Symposium, Mallorca (Jun. 29–Jul. 3, 1996).

Mulbry, "Purification and Characterization of an Inducible s–Triazine Hydrolase from Rhodococcus corallinus NRRL B–15444R," *Applied and Environmental Microbiology*, 60, 613–618 (1994).

Nagy et al., "A Single Cytochrome P–450 System Is Involved in Degradation of the Herbicides EPTC (S–Ethyl Dipropylthiocarbamate) and Atrazine by Rhodococcus sp. Strain NI86/21," *Applied and Environmental Microbiology*, 61, 2056–2060 (1995).

Nair et al., "Effects of Two Electron Acceptors on Atrazine Mineralization Rates in Soil," *Environ. Sci. Technol.*, 26, 2298–2300 (1992).

Nissim et al., "Antibody fragments from a 'single pot' phage display library as immunochemical reagents," *EMBO J.*, 13, 692–698 (1994).

Oliphant et al., "Cloning of random–sequence oligodeoxynucleotides," *Gene*, 44, 177–183 (1986).

Radke et al., "Evaluation of the Pyridine–Alkali Colorimetric Method for Determination of Atrazine," *J. Agr. Food Chem.*, 14, 70–73 (1966).

Radosevich et al., "Degradation and Mineralization of Atrazine by a Soil Bacterial Isolate," *Appl. Environ. Microbiol.*, 61, 297–302 (1995).

Ragab et al., "Colorimetric Methods for the Determination of Simazine and Related Chloro–s–triazines," *J. Agr. Food. Chem.*, 16, 284–289 (1968).

Scott et al.,"Searching for Peptide Ligands with an Epitope Library," *Science*, 249, 386–390 (1990).

Shao et al., "Cloning and Expression of the s–Traizine Hydrolase Gene (trzA) from Rhodococcus corallinus and Development of Rhodococcus Recombinant Strains Capable of Dealkylating and Dechlorinating the Herbicide Atrazine," *Journal of Bacteriology*, 177, 5748–5755 (1995).

Shao et al., "Cloning of the Genes for Degradation of the Herbicides EPTC (S–Ethyl Dipropylthiocarbamate) and Atrazine from Rhodococcus sp. Strain TE1," *Appl. Environ. Microbiol.*, 61, 2061–2065 (1995).

de Souza et al., "Indentification of a Gene Cluster from Pseudomonas sp. ADP, Involved in Atrazine Biodegradation," *Abstracts of the 95$^{th}$ General Meeting of the American Society for Microbiology 1995*, abstract Q–89, p. 415 (May 21–25, 1995).

de Souza et al., "Cloning, Characterization, and Expression of a Gene Region from Pseudomonas sp. Strain ADP Involved in the Dechlorination of Atrazine," *Appl. Environ. Microbiol.*, 61, 3373–3378 (1995).

de Souza et al., "Atrazine Chlorohydrolase from Pseudomonas sp. Strain ADP: Gene Sequence, Enzyme Purification, and Protein Characterization," *J. Bacteriology*, 178, 4894–4900 (1996).

Stemmer et al., "DNA shuffling by random fragmentation and reassembly: In vitro recombination for molecular evolution," *Proc. Natl. Acad. Sci. USA*, 91, 10747–10751 (1994).

Stemmer et al., "Rapid evolution of a protein in vitro by DNA shuffling," *Nature*, 370, 389–391 (1994).

U.S. Department of Agriculture–BARD Program, Grant No. 94–34339–112, obtained from the Department of BARD, abstract only (1994).

Winter et al., "Making Antibodies by Phage Display Technology," *Ann. Rev. Immunol.*, 12, 433–455 (1994).

Yanze–Kontchou et al., "Mineralization of the Herbicide Atrazine as a Carbon Source by a Pseudomonas Strain," *Appl. Environ. Microbiol.*, 60, 4297–4302 (1994).

```
  1 .............................................GCGA   4
                                                 ||||
  1 CTCGGGTAACTTCTTGAGCGCGGCCACAGCAGCCTTGATCATGAAGGCGA  50

5 GCATGGTGACCTTGACGCCGCTCTTTTCGTTCTCTTTGTTGAACTGCACG  54
    ||||||||||||||||||||||||||||||||||||||||||||||||||
 51 GCATGGTGACCTTGACGCCGCTCTTTTCGTTCTCTTTGTTGAACTGCACG 100

55 CGAAAGGCTTCCAGGTCGGTGATGTCCGCGTCGTCGTGGTTGGTGACGTG 104
    ||||||||||||||||||||||||||||||||||||||||||||||||||
101 CGAAAGGCTTCCAGGTCGGTGATGTCCGCGTCGTCGTGGTTGGTGACGTG 150

105 CGGGATGACCACCCAGTTGCGGTGCAGGTTTTTCGATGGCATAATATCTG 154
    ||||||||||||||||||||||||||||||||||||||||||||||||||
151 CGGGATGACCACCCAGTTGCGGTGCAGGTTTTTCGATGGCATAATATCTG 200

155 CGTTGCGACGTGTAACACACTATTGGAGACATATCATGCAAACGCTCAGC 204
    ||||||||||||||||||||||||||||||||||||||||||||||||||
201 CGTTGCGACGTGTAACACACTATTGGAGACATATCATGCAAACGCTCAGC 250

205 ATCCAGCACGGTACCCTCGTCACGATGGATCAGTACCGCAGAGTCCTTGG 254
    ||||||||||||||||||||||||||||||||||||||||||||||||||
251 ATCCAGCACGGTACCCTCGTCACGATGGATCAGTACCGCAGAGTCCTTGG 300

255 GGATAGCTGGGTTCACGTGCAGGATGGACGGATCGTCGCGCTCGGAGTGC 304
    ||||||||||||||||||||||||||||||||||||||||||||||||||
301 GGATAGCTGGGTTCACGTGCAGGATGGACGGATCGTCGCGCTCGGAGTGC 350

305 ACGCCGAGTCGGTGCCTCCGCCAGCGGATCGGGTGATCGATGCACGCGGC 354
    ||||||||||||||||||||||||||||||||||||||||||||||||||
351 ACGCCGAGTCGGTGCCTCCGCCAGCGGATCGGGTGATCGATGCACGCGGC 400

355 AAGGTCGTGTTACCCGGTTTCATCAATGCCCACACCCATGTGAACCAGAT 404
    ||||||||||||||||||||||||||||||||||||||||||||||||||
401 AAGGTCGTGTTACCCGGTTTCATCAATGCCCACACCCATGTGAACCAGAT 450

405 CCTCCTGCGCGGAGGGCCCTCGCACGGGCGTCAATTCTATGACTGGCTGT 454
    |||||||||||||||||||||||||| |||||||||||||||||||||||
451 CCTCCTGCGCGGAGGGCCCTCGCACGGACGTCAATTCTATGACTGGCTGT 500

455 TCAACGTTGTGTATCCGGGACAAAAGGCGATGAGACCGGAGGACGTAGCG 504
    ||||||||||||||||||||||||||||||||||||||||||||||||||
501 TCAACGTTGTGTATCCGGGACAAAAGGCGATGAGACCGGAGGACGTAGCG 550

505 GTGGCGGTGAGGTTGTATTGTGCGGAAGCTGTGCGCAGCGGGATTACGAC 554
    ||||||||||||||||||||||||||||||||||||||||||||||||||
551 GTGGCGGTGAGGTTGTATTGTGCGGAAGCTGTGCGCAGCGGGATTACGAC 600

555 GATCAACGAAAACGCCGATTCGGCCATCTACCCAGGCAACATCGAGGCCG 604
    ||||||||||||||||||||||||||||||||||||||||||||||||||
601 GATCAACGAAAACGCCGATTCGGCCATCTACCCAGGCAACATCGAGGCCG 650
```

Fig. 1A

```
 605 CGATGGCGGTCTATGGTGAGGTGGGTGTGAGGGTCGTCTACGCCCGCATG  654
     ||||||||||||||||||||||||||||||||||||||||||||||||||
 651 CGATGGCGGTCTATGGTGAGGTGGGTGTGAGGGTCGTCTACGCCCGCATG  700

655 TTCTTTGATCGGATGGACGGGCGCATTCAAGGGTATGTGGACGCCTTGAA  704
     ||||||||||||||||||||||||||||||||||||||||||||||||||
 701 TTCTTTGATCGGATGGACGGGCGCATTCAAGGGTATGTGGACGCCTTGAA  750

705 GGCTCGCTCTCCCCAAGTCGAACTGTGCTCGATCATGGAGGGAACGGCTG  754
     ||||||||||||||||||||||||||||||||||||||||| ||||||||
 751 GGCTCGCTCTCCCCAAGTCGAACTGTGCTCGATCATGGAGGAAACGGCTG  800

755 TGGCCAAAGATCGGATCACAGCCCTGTCAGATCAGTATCATGGCACGGCA  804
     ||||||||||||||||||||||||||||||||||||||||||||||||||
 801 TGGCCAAAGATCGGATCACAGCCCTGTCAGATCAGTATCATGGCACGGCA  850

805 GGAGGTCGTATATCAGTTTGGCCCGCTCCTGCCACTACCACGGCGGTGAC  854
     ||||||||||||||||||||||||||||||||||||||||||||||||||
 851 GGAGGTCGTATATCAGTTTGGCCCGCTCCTGCCACTACCACGGCGGTGAC  900

855 AGTTGAAGGAATGCGATGGGCACAAGCCTTCGCCCGTGATCGGGCGGTAA  904
     ||||||||||||||||||||||||||||||||||||||||||||||||||
 901 AGTTGAAGGAATGCGATGGGCACAAGCCTTCGCCCGTGATCGGGCGGTAA  950

905 TGTGGACGCTTCACATGGCGGAGAGCGATCATGATGAGCGGATTCATGGG  954
     ||||||||||||||||||||||||||||||||||||||||||||||||||
 951 TGTGGACGCTTCACATGGCGGAGAGCGATCATGATGAGCGGATTCATGGG 1000

955 ATGAGTCCCGCCGAGTACATGGAGTGTTACGGACTCTTGGATGAGCGTCT 1004
     ||||||||||||||||||||||||||||||||||||||||||||||||||
1001 ATGAGTCCCGCCGAGTACATGGAGTGTTACGGACTCTTGGATGAGCGTCT 1050

1005 GCAGGTCGCGCATTGCGTGTACTTTGACCGGAAGGATGTTCGGCTGCTGC 1054
     ||||||||||||||||||||||||||||||||||||||||||||||||||
1051 GCAGGTCGCGCATTGCGTGTACTTTGACCGGAAGGATGTTCGGCTGCTGC 1100

1055 ACCGCCACAATGTGAAGGTCGCGTCGCAGGTTGTGAGCAATGCCTACCTC 1104
     ||||||||||||||||||||||||||||||||||||||||||||||||||
1101 ACCGCCACAATGTGAAGGTCGCGTCGCAGGTTGTGAGCAATGCCTACCTC 1150

1105 GGCTCAGGGGTGGCCCCCGTGCCAGAGATGGTGGAGCGCGGCATGGCCGT 1154
     ||||||||||||||||||||||||||||||||||||||||||||||||||
1151 GGCTCAGGGGTGGCCCCCGTGCCAGAGATGGTGGAGCGCGGCATGGCCGT 1200

1155 GGGCATTGGAACAGATAACGGGAATAGTAATGACTCCGTAAACATGATCG 1204
     |||||||||||||||||||||||||||||||||||| |||||||||||||
1201 GGGCATTGGAACAGATAACGGGAATAGTAATGACTCCGCAAACATGATCG 1250

1205 GAGACATGAAGTTTATGGCCCATATTCACCGCGCGGTGCATCGGGATGCG 1254
     ||||||||||||||||||||||||||||||||||||||||||||||||||
1251 GAGACATGAAGTTTATGGCCCATATTCACCGCGCGGTGCATCGGGATGCG 1300
```

*Fig 1B*

1255 GACGTGCTGACCCCAGAGAAGATTCTTGAAATGGCGACGATCGATGGGGC 1304
     ||||||||||||||||||||||||||||||||||||||||||||||||||
1301 GACGTGCTGACCCCAGAGAAGATTCTTGAAATGGCGACGATCGATGGGGC 1350

1305 GCGTTCGTTGGGAATGGACCACGAGATTGGTTCCATCGAAACCGGCAAGC 1354
     ||||||||||||||||||||||||||||||||||||||||||||||||||
1351 GCGTTCGTTGGGAATGGACCACGAGATTGGTTCCATCGAAACCGGCAAGC 1400

1355 GCGCGGACCTTATCCTGCTTGACCTGCGTCACCCTCAGACGACTCCTCAC 1404
     |||||||||||||||||||||||||||| |||||||||||||   |||
1401 GCGCGGACCTTATCCTGCTTGACCTGCGTCA.CCTCAGACGACTC..TCA 1447

1405 CATCATTTGGCGGCCACGATCGTGTTTCAGGCTTACGGCAATGAGGTGGA 1454
     ||||||||||||||||||||||||||||||||||||||||||||||||||
1448 CATCATTTGGCGGCCACGATCGTGTTTCAGGCTTACGGCAATGAGGTGGA 1497

1455 CACTGTCCTGATTGACGGAAACGTTGTGATGGAGAACCGCCGCTTGAGCT 1504
     ||||||||||||||||||||||||||||||||||||||||||||||||||
1498 CACTGTCCTGATTGACGGAAACGTTGTGATGGAGAACCGCCGCTTGAGCT 1547

1505 TTCTTCCCCCTGAACGTGAGTTGGCGTTCCTTGAGGAAGCGCAGAGCCGC 1554
     ||||||||||||||||||||||||||||||||||||||||||||||||||
1548 TTCTTCCCCCTGAACGTGAGTTGGCGTTCCTTGAGGAAGCGCAGAGCCGC 1597

1555 GCCACAGCTATTTTGCAGCGGGCGAACATGGTGGCTAACCCAGCTTGGCG 1604
     ||||||||||||||||||||||||||||||||||||||||||||||||||
1598 GCCACAGCTATTTTGCAGCGGGCGAACATGGTGGCTAACCCAGCTTGGCG 1647

1605 CAGCCTCTAGGAAATGACGCCGTTGCTGCATCCGCCGCCCCTTGAGGAAA 1654
     ||||||||||||||||||||||||||||||||||||||||||||||||||
1648 CAGCCTCTAGGAAATGACGCCGTTGCTGCATCCGCCGCCCCTTGAGGAAA 1697

1655 TCGCTGCCATCTTGGCGCGGCTCGGATTGGGGGGCGGACATGACCTTGAT 1704
     ||||||||||||||||||||||||||||||||||||||||||||||||||
1698 TCGCTGCCATCTTGGCGCGGCTCGGATTGGGGGGCGGACATGACCTTGAT 1747

1705 GGATACAGAATTGCCATGAATGCGGCACTTCCGTCCTTCGCTCGTGTGGA 1754
     ||||||||||||||||||||||||||||||||||||||||||||||||||
1748 GGATACAGAATTGCCATGAATGCGGCACTTCCGTCCTTCGCTCGTGTGGA 1797

1755 ATCGTTGGTAGGTGAGGGTCGACTGCGGGCGCCAGCTTCCCGAAGAAGTG 1804
     |||||||||||||||||||||||||||||||||||||||||||||| |||
1798 ATCGTTGGTAGGTGAGGGTCGACTGCGGGCGCCAGCTTCCCGAAGAGGTG 1847

1805 AAAG....... 1808
     ||||
1848 AAAGGCCCGAG 1858

*Fig. 1C*

```
  1 ..............GAGCGCCGCCACAGCAGCCTTGATCATGAAGGCGA  35
                 ||||||| ||||||||||||||||||||||||||||
  1 CTCGGGTAACTTCTTGAGCGCGGCCACAGCAGCCTTGATCATGAAGGCGA  50

36 GCATGGTGACCTTGACGCCGCTCTTTTCGTTCTCTTTGTTGAACTGCACG  85
    ||||||||||||||||||||||||||||||||||||||||||||||||||
 51 GCATGGTGACCTTGACGCCGCTCTTTTCGTTCTCTTTGTTGAACTGCACG 100

86 CGAAAGGCTTCCAGGTCGGTGATGTCCGCGTCGTCGTGGTTGGTGACGTG 135
    ||||||||||||||||||||||||||||||||||||||||||||||||||
101 CGAAAGGCTTCCAGGTCGGTGATGTCCGCGTCGTCGTGGTTGGTGACGTG 150

136 CGGGATGACCACCCAGTTGCGGTGCAGGTTTTTCGATGGCGTAATATCTG 185
    |||||||||||||||||||||||||||||||||||||||| |||||||||
151 CGGGATGACCACCCAGTTGCGGTGCAGGTTTTTCGATGGCATAATATCTG 200

186 CGTTGCGACGTGTAACACACTATTGGAGACATATCATGCAAACGCTCAGC 235
    ||||||||||||||||||||||||||||||||||||||||||||||||||
201 CGTTGCGACGTGTAACACACTATTGGAGACATATCATGCAAACGCTCAGC 250

236 ATCCAGCACGGTACCCTCGTCACGATGGATCAGTACCGCAGAGTCCTTGG 285
    ||||||||||||||||||||||||||||||||||||||||||||||||||
251 ATCCAGCACGGTACCCTCGTCACGATGGATCAGTACCGCAGAGTCCTTGG 300

286 GGATAGCTGGGTTCACGTGCAGGATGGACGGATCGTCGCGCTCGGAGTGC 335
    ||||||||||||||||||||||||||||||||||||||||||||||||||
301 GGATAGCTGGGTTCACGTGCAGGATGGACGGATCGTCGCGCTCGGAGTGC 350

336 ACGCCGAGTCGGTGCCTCCGCCAGCGGATCGGGTGATCGATGCACGCGGC 385
    ||||||||||||||||||||||||||||||||||||||||||||||||||
351 ACGCCGAGTCGGTGCCTCCGCCAGCGGATCGGGTGATCGATGCACGCGGC 400

386 AAGGTCGTGTTACCCGGTTTCATCAATGCCCACACCCATGTGAACCAGAT 435
    ||||||||||||||||||||||||||||||||||||||||||||||||||
401 AAGGTCGTGTTACCCGGTTTCATCAATGCCCACACCCATGTGAACCAGAT 450

436 CCTCCTGCGCGGAGGGCCCTCGCACGGGCGTCAATTCTATGACTGGCTGT 485
    |||||||||||||||||||||||||||| |||||||||||||||||||||
451 CCTCCTGCGCGGAGGGCCCTCGCACGGACGTCAATTCTATGACTGGCTGT 500

486 TCAACGTTGTGTATCCGGGACAAAAGGCGATGAGACCGGAGGACGTAGCG 535
    ||||||||||||||||||||||||||||||||||||||||||||||||||
501 TCAACGTTGTGTATCCGGGACAAAAGGCGATGAGACCGGAGGACGTAGCG 550

536 GTGGCGGTGAGGTTGTATTGTGCGGAAGCTGTGCGCAGCGGGATTACGAC 585
    ||||||||||||||||||||||||||||||||||||||||||||||||||
551 GTGGCGGTGAGGTTGTATTGTGCGGAAGCTGTGCGCAGCGGGATTACGAC 600

586 GATCAACGAAAACGCCGATTCGGCCATCTACCCAGGCAACATCGAGGCCG 635
    ||||||||||||||||||||||||||||||||||||||||||||||||||
601 GATCAACGAAAACGCCGATTCGGCCATCTACCCAGGCAACATCGAGGCCG 650
```

*Fig. 2A*

```
 636 CGATGGCGGTCTATGGTGAGGTGGGTGTGAGGGTCGTCTACGCCCGCATG  685
     ||||||||||||||||||||||||||||||||||||||||||||||||||
 651 CGATGGCGGTCTATGGTGAGGTGGGTGTGAGGGTCGTCTACGCCCGCATG  700

686 TTCTTTGATCGGATGGACGGGCGCATTCAAGGGTATGTGGACGCCTTGAA  735
     ||||||||||||||||||||||||||||||||||||||||||||||||||
 701 TTCTTTGATCGGATGGACGGGCGCATTCAAGGGTATGTGGACGCCTTGAA  750

736 GGCTCGCTCTCCCCAAGTCGAACTGTGCTCGATCATGGAGGAAACGGCTG  785
     ||||||||||||||||||||||||||||||||||||||||||||||||||
 751 GGCTCGCTCTCCCCAAGTCGAACTGTGCTCGATCATGGAGGAAACGGCTG  800

786 TGGCCAAAGATCGGATCACAGCCCTGTCAGATCAGTATCATGGCACGGCA  835
     ||||||||||||||||||||||||||||||||||||||||||||||||||
 801 TGGCCAAAGATCGGATCACAGCCCTGTCAGATCAGTATCATGGCACGGCA  850

836 GGAGGTCGTATATCAGTTTGGCCCGCTCCTGCCACTACCACGGCGGTGAC  885
     ||||||||||||||||||||||||||||||||||||||||||||||||||
 851 GGAGGTCGTATATCAGTTTGGCCCGCTCCTGCCACTACCACGGCGGTGAC  900

886 AGTTGAAGGAATGCGATGGGCACAAGCCTTCGCCCGTGATCGGGCGGTAA  935
     ||||||||||||||||||||||||||||||||||||||||||||||||||
 901 AGTTGAAGGAATGCGATGGGCACAAGCCTTCGCCCGTGATCGGGCGGTAA  950

936 TGTGGACGCTTCACATGGCGGAGAGCGATCATGATGAGCGGATTCATGGG  985
     ||||||||||||||||||||||||||||||||||||||||||||||||||
 951 TGTGGACGCTTCACATGGCGGAGAGCGATCATGATGAGCGGATTCATGGG 1000

986 ATGAGTCCCGCCGATTACATGGAGTGTTACGGACTCTTGGATGAGCGTCT 1035
     ||||||||||||  ||||||||||||||||||||||||||||||||||||
1001 ATGAGTCCCGCCGAGTACATGGAGTGTTACGGACTCTTGGATGAGCGTCT 1050

1036 GCAGGTCGCGCATTGCGTGTACTTTGACCGGAAGGATGTTCGGCTGCTGC 1085
     ||||||||||||||||||||||||||||||||||||||||||||||||||
1051 GCAGGTCGCGCATTGCGTGTACTTTGACCGGAAGGATGTTCGGCTGCTGC 1100

1086 ACCGCCACAATGTGAAGGTCGCGTCGCAGGTTGTGAGCAATGCCTACCTC 1135
     ||||||||||||||||||||||||||||||||||||||||||||||||||
1101 ACCGCCACAATGTGAAGGTCGCGTCGCAGGTTGTGAGCAATGCCTACCTC 1150

1136 GGCTCAGGGGTGGCCCCCGTGCCAGAGATGGTGGAGCGCGGCATGGCCGT 1185
     ||||||||||||||||||||||||||||||||||||||||||||||||||
1151 GGCTCAGGGGTGGCCCCCGTGCCAGAGATGGTGGAGCGCGGCATGGCCGT 1200

1186 GGGCATTGGAACAGATAACGGGAATAGTAATGACTCCGTAAACATGATCG 1235
     |||||||||||||||||||||||||||||||||||||| |||||||||||
1201 GGGCATTGGAACAGATAACGGGAATAGTAATGACTCCGCAAACATGATCG 1250

1236 GAGACATGAAGTTTATGGCCCATATTCACCGCGCGGTGCATCGGGATGCG 1285
     ||||||||||||||||||||||||||||||||||||||||||||||||||
1251 GAGACATGAAGTTTATGGCCCATATTCACCGCGCGGTGCATCGGGATGCG 1300
```

Fig. 2B

```
1286 GACGTGCTGACCCCAGAGAAGATTCTTGAAATGGCGACGATCGATGGGGC 1335
     ||||||||||||||||||||||||||||||||||||||||||||||||||
1301 GACGTGCTGACCCCAGAGAAGATTCTTGAAATGGCGACGATCGATGGGGC 1350

1336 GCGTTCGTTGGGGATGGACCACGAGATTGGTTCCATCGAAACCGGCAAGC 1385
     |||||||||||| |||||||||||||||||||||||||||||||||||||
1351 GCGTTCGTTGGGAATGGACCACGAGATTGGTTCCATCGAAACCGGCAAGC 1400

1386 GCGCGGACCTTATCCTGCTTGACCTGCGTCACCCTCAGACGACTCCTCAC 1435
     |||||||||||||||||||||||||||||| ||||||||||||   |||
1401 GCGCGGACCTTATCCTGCTTGACCTGCGTCA.CCTCAGACGACT..TCA 1447

1436 CATCATTTGGCGGCCACGATCGTGTTTCAGGCTTACGGCAATGAGGTGGA 1485
     ||||||||||||||||||||||||||||||||||||||||||||||||||
1448 CATCATTTGGCGGCCACGATCGTGTTTCAGGCTTACGGCAATGAGGTGGA 1497

1486 CACTGTCCTGATTGACGGAAACGTTGTGATGGAGAACCGCCGCTTGAGCT 1535
     ||||||||||||||||||||||||||||||||||||||||||||||||||
1498 CACTGTCCTGATTGACGGAAACGTTGTGATGGAGAACCGCCGCTTGAGCT 1547

1536 TTCTTCCCCCTGAACGTGAGTTGGCGTTCCTTGAGGAAGCGCAGAGCCGC 1585
     ||||||||||||||||||||||||||||||||||||||||||||||||||
1548 TTCTTCCCCCTGAACGTGAGTTGGCGTTCCTTGAGGAAGCGCAGAGCCGC 1597

1586 GCCACAGCTATTTTGCAGCGGGCGAACATGGTGGCTAACCCAGCTTGGCG 1635
     ||||||||||||||||||||||||||||||||||||||||||||||||||
1598 GCCACAGCTATTTTGCAGCGGGCGAACATGGTGGCTAACCCAGCTTGGCG 1647

1636 CAGCCTCTAGGAAATGACGCCGTTGCTGCATCCGCCGCCCCTTGAGGAAA 1685
     ||||||||||||||||||||||||||||||||||||||||||||||||||
1648 CAGCCTCTAGGAAATGACGCCGTTGCTGCATCCGCCGCCCCTTGAGGAAA 1697

1686 TCGCTGCCATCTTGGCGCGGCTCGGATTGGGGGGCGGACATGACCTTGAT 1735
     ||||||||||||||||||||||||||||||||||||||||||||||||||
1698 TCGCTGCCATCTTGGCGCGGCTCGGATTGGGGGGCGGACATGACCTTGAT 1747

1736 GGATACAGAATTGCCATGAATGCGGCACTTCCGTCCTTCGCTCGTGTGGA 1785
     ||||||||||||||||||||||||||||||||||||||||||||||||||
1748 GGATACAGAATTGCCATGAATGCGGCACTTCCGTCCTTCGCTCGTGTGGA 1797

1786 ATCGTTGGTAGGTGAGGGTCGACTGCGGGCGCCAGCTTCCCGAAGAAGTG 1835
     |||||||||||||||||||||||||||||||||||||||||||||| |||
1798 ATCGTTGGTAGGTGAGGGTCGACTGCGGGCGCCAGCTTCCCGAAGAGGTG 1847

1836 AAAGGCCCGAG 1846
     |||||||||||
1848 AAAGGCCCGAG 1858
```

Fig. 2C

```
  1 ..............ASMVTLTPLFSFSLLNCTRKASRSVMSASSWLVTC  35
                 ||||||||||||||||||||||||||||||||||||
  1 SGNFLSAATAALIMKASMVTLTPLFSFSLLNCTRKASRSVMSASSWLVTC  50

36 GMTTQLRCRFFDGIISALRRVTHYWRHIMQTLSIQHGTLVTMDQYRRVLG  85
    |||||||||||||||||||||||||||||||||||||||||||||||||
 51 GMTTQLRCRFFDGIISALRRVTHYWRHIMQTLSIQHGTLVTMDQYRRVLG 100

86 DSWVHVQDGRIVALGVHAESVPPPADRVIDARGKVVLPGFINAHTHVNQI 135
    |||||||||||||||||||||||||||||||||||||||||||||||||
101 DSWVHVQDGRIVALGVHAESVPPPADRVIDARGKVVLPGFINAHTHVNQI 150

136 LLRGGPSHGRQFYDWLFNVVYPGQKAMRPEDVAVAVRLYCAEAVRSGITT 185
    |||||||||||||||||||||||||||||||||||||||||||||||||
151 LLRGGPSHGRQFYDWLFNVVYPGQKAMRPEDVAVAVRLYCAEAVRSGITT 200

186 INENADSAIYPGNIEAAMAVYGEVGVRVVYARMFFDRMDGRIQGYVDALK 235
    |||||||||||||||||||||||||||||||||||||||||||||||||
201 INENADSAIYPGNIEAAMAVYGEVGVRVVYARMFFDRMDGRIQGYVDALK 250

236 ARSPQVELCSIMEGTAVAKDRITALSDQYHGTAGGRISVWPAPATTTAVT 285
    |||||||||||:|||||||||||||||||||||||||||||||||||||
251 ARSPQVELCSIMEETAVAKDRITALSDQYHGTAGGRISVWPAPATTTAVT 300

286 VEGMRWAQAFARDRAVMWTLHMAESDHDERIHGMSPAEYMECYGLLDERL 335
    |||||||||||||||||||||||||||||||||||||||||||||||||
301 VEGMRWAQAFARDRAVMWTLHMAESDHDERIHGMSPAEYMECYGLLDERL 350

336 QVAHCVYFDRKDVRLLHRHNVKVASQVVSNAYLGSGVAPVPEMVERGMAV 385
    |||||||||||||||||||||||||||||||||||||||||||||||||
351 QVAHCVYFDRKDVRLLHRHNVKVASQVVSNAYLGSGVAPVPEMVERGMAV 400

386 GIGTDNGNSNDSVNMIGDMKFMAHIHRAVHRDADVLTPEKILEMATIDGA 435
    |||||||||||.|||||||||||||||||||||||||||||||||||||
401 GIGTDNGNSNDSANMIGDMKFMAHIHRAVHRDADVLTPEKILEMATIDGA 450

436 RSLGMDHEIGSIETGKRADLILLDLRHPQTTPHHHLAATIVFQAYGNEVD 485
    |||||||||||||||||||||||||||||  ||||||||||||||
451 RSLGMDHEIGSIETGKRADLILLDLRHLRRLS.HHLAATIVFQAYGNEVD 499

486 TVLIDGNVVMENRRLSFLPPERELAFLEEAQSRATAILQRANMVANPAWR 535
    |||||||||||||||||||||||||||||||||||||||||||||||||
500 TVLIDGNVVMENRRLSFLPPERELAFLEEAQSRATAILQRANMVANPAWR 549

536 SL*EMTPLLHPPPLEEIAAILARLGLGGGHDLDGYRIAMNAALPSFARVE 585
    |||||||||||||||||||||||||||||||||||||||||||||||||
550 SL*EMTPLLHPPPLEEIAAILARLGLGGGHDLDGYRIAMNAALPSFARVE 599

586 SLVGEGRLRAPASRRSE... 602
    ||||||||||||||||:|
600 SLVGEGRLRAPASRRGERPE 619
```

*Fig. 3*

```
  1 .....SAATAALIMKASMVTLTPLFSFSLLNCTRKASRSVMSASSWLVTC  45
       |||||||||||||||||||||||||||||||||||||||||||||
  1 SGNFLSAATAALIMKASMVTLTPLFSFSLLNCTRKASRSVMSASSWLVTC  50

46 GMTTQLRCRFFDGVISALRRVTHYWRHIMQTLSIQHGTLVTMDQYRRVLG  95
    ||||||||||||||:||||||||||||||||||||||||||||||||||
 51 GMTTQLRCRFFDGIISALRRVTHYWRHIMQTLSIQHGTLVTMDQYRRVLG 100

96 DSWVHVQDGRIVALGVHAESVPPPADRVIDARGKVVLPGFINAHTHVNQI 145
    |||||||||||||||||||||||||||||||||||||||||||||||||
101 DSWVHVQDGRIVALGVHAESVPPPADRVIDARGKVVLPGFINAHTHVNQI 150

146 LLRGGPSHGRQFYDWLFNVVYPGQKAMRPEDVAVAVRLYCAEAVRSGITT 195
    |||||||||||||||||||||||||||||||||||||||||||||||||
151 LLRGGPSHGRQFYDWLFNVVYPGQKAMRPEDVAVAVRLYCAEAVRSGITT 200

196 INENADSAIYPGNIEAAMAVYGEVGVRVVYARMFFDRMDGRIQGYVDALK 245
    |||||||||||||||||||||||||||||||||||||||||||||||||
201 INENADSAIYPGNIEAAMAVYGEVGVRVVYARMFFDRMDGRIQGYVDALK 250

246 ARSPQVELCSIMEETAVAKDRITALSDQYHGTAGGRISVWPAPATTTAVT 295
    |||||||||||||||||||||||||||||||||||||||||||||||||
251 ARSPQVELCSIMEETAVAKDRITALSDQYHGTAGGRISVWPAPATTTAVT 300

296 VEGMRWAQAFARDRAVMWTLHMAESDHDERIHGMSPADYMECYGLLDERL 345
    |||||||||||||||||||||||||||||||||||||:||||||||||||
301 VEGMRWAQAFARDRAVMWTLHMAESDHDERIHGMSPAEYMECYGLLDERL 350

346 QVAHCVYFDRKDVRLLHRHNVKVASQVVSNAYLGSGVAPVPEMVERGMAV 395
    |||||||||||||||||||||||||||||||||||||||||||||||||
351 QVAHCVYFDRKDVRLLHRHNVKVASQVVSNAYLGSGVAPVPEMVERGMAV 400

396 GIGTDNGNSNDSVNMIGDMKFMAHIHRAVHRDADVLTPEKILEMATIDGA 445
    ||||||||||||.||||||||||||||||||||||||||||||||||||
401 GIGTDNGNSNDSANMIGDMKFMAHIHRAVHRDADVLTPEKILEMATIDGA 450

446 RSLGMDHEIGSIETGKRADLILLDLRHPQTTPHHHLAATIVFQAYGNEVD 495
    |||||||||||||||||||||||||||||.  .||||||||||||||||
451 RSLGMDHEIGSIETGKRADLILLDLRHLRRLS.HHLAATIVFQAYGNEVD 499

496 TVLIDGNVVMENRRLSFLPPERELAFLEEAQSRATAILQRANMVANPAWR 545
    |||||||||||||||||||||||||||||||||||||||||||||||||
500 TVLIDGNVVMENRRLSFLPPERELAFLEEAQSRATAILQRANMVANPAWR 549

546 SL*EMTPLLHPPPLEEIAAILARLGLGGGHDLDGYRIAMNAALPSFARVE 595
    |||||||||||||||||||||||||||||||||||||||||||||||||
550 SL*EMTPLLHPPPLEEIAAILARLGLGGGHDLDGYRIAMNAALPSFARVE 599

596 SLVGEGRLRAPASRRSERPE 615
    |||||||||||||||:||||
600 SLVGEGRLRAPASRRGERPE 619
```

Fig. 4

```
545 CGGTATCGGGGAATTNTTGAGCGCGGCCACAGCAGCCNTGATCATGAAGG 496
      ||  |  ||:|||||||||||||||||||||||:||||||||||||
  1 ...CTCGGGTAACTTCTTGAGCGCGGCCACAGCAGCCTTGATCATGAAGG  47

495 CGAGCATGGTGACCTNGACGCCGTNTTTTNGTTNTTTTTTGTTGAACTGC 446
    ||||||||||||||||:||||||| :  |||:   |: |  ||||||||||
 48 CGAGCATGGTGACCTTGACGCCGCTCTTTTCGTTCTCTTTGTTGAACTGC  97

445 ACGCGAAAGG.TTCCAGGTCGGTGATGTCCGCGTCGTCGTGGTTGGTGAC 397
    |||||||||| |||||||||||||||||||||||||||||||||||||||
 98 ACGCGAAAGGCTTCCAGGTCGGTGATGTCCGCGTCGTCGTGGTTGGTGAC 147

396 GTGCGGGATGACCACCCAGNTGCGGTGCAGGTTTTTCGATGGCATAATAT 347
    |||||||||||||||||||:||||||||||||||||||||||||||||||
148 GTGCGGGATGACCACCCAGTTGCGGTGCAGGTTTTTCGATGGCATAATAT 197

346 CTGCGTTGCGACGTGTAACACACTANTGGAGACATATCATGCAAACGCTC 297
    |||||||||||||||||||||||||:||||||||||||||||||||||||
198 CTGCGTTGCGACGTGTAACACACTATTGGAGACATATCATGCAAACGCTC 247

296 AGCATCCAGCACGGTACCCTCGTCACGATGGATCAGTACCGCAGAGTCCT 247
    ||||||||||||||||||||||||||||||||||||||||||||||||||
248 AGCATCCAGCACGGTACCCTCGTCACGATGGATCAGTACCGCAGAGTCCT 297

246 TGGGGATAGNTGGGTTCACGTGCAGGATGGACGGATCGTCGCGCTCGGAG 197
    |||||||||:||||||||||||||||||||||||||||||||||||||||
298 TGGGGATAGCTGGGTTCACGTGCAGGATGGACGGATCGTCGCGCTCGGAG 347

196 TGCACGCCGAGTCGGTGCCTCCGCCAGCGGATCGGGTGATCGATGCACGC 147
    ||||||||||||||||||||||||||||||||||||||||||||||||||
348 TGCACGCCGAGTCGGTGCCTCCGCCAGCGGATCGGGTGATCGATGCACGC 397

146 GGCAAGGTCGTGTTACCCGGTTTCATCAATGCCCACACCCATGTGAACCA  97
    ||||||||||||||||||||||||||||||||||||||||||||||||||
398 GGCAAGGTCGTGTTACCCGGTTTCATCAATGCCCACACCCATGTGAACCA 447

96 GATCCTCCTGCGCGGAGGGCCNTCGCACGGGCGTCAATTNTATGACTGGC  47
    |||||||||||||||||||||:||||||||| ||||||:|||||||||
448 GATCCTCCTGCGCGGAGGGCCCTCGCACGGACGTCAATTCTATGACTGGC 497

46 TGTTCAACGTTGTGTATCCGGGACAAAAGGCGATGAGACCGGAGGA....   1
    |||||||||||||||||||||||||||||||||||||||||||||
498 TGTTCAACGTTGTGTATCCGGGACAAAAGGCGATGAGACCGGAGGACGTA 547
```

Fig. 5A

```
  1 ...CCTGCGCGGAGGGCCTCCGCACGGGCGTCAATTCTATGACTGGCTGT  47
         |||||||||||||||  |||||||  |||||||||||||||||||||||
451    CCTCCTGCGCGGAGGGCCCTCGCACGGACGTCAATTCTATGACTGGCTGT 500

48 TCAACGTTGTGTATCCGGGACAAAAGGCGATGAGACCGGAGGACGTANCG  97
    ||||||||||||||||||||||||||||||||||||||||||||||||:||
501 TCAACGTTGTGTATCCGGGACAAAAGGCGATGAGACCGGAGGACGTAGCG 550

98 GTGGCGGTGAGGTTGTATTGTGCGGAAGCTGTGCGCAGCGGGATTACGAC 147
    |||||||||||||||||||||||||||||||||||||||||||||||||
551 GTGGCGGTGAGGTTGTATTGTGCGGAAGCTGTGCGCAGCGGGATTACGAC 600

148 GATCAACGAAAACNCCGATTCGGCCATCTACCCAGGCAACATCGAGGCCG 197
    |||||||||||||:||||||||||||||||||||||||||||||||||||
601 GATCAACGAAAACGCCGATTCGGCCATCTACCCAGGCAACATCGAGGCCG 650

198 CGATGGCGGTCTATGGTGAGGTGGGTGTGAGGGTCGTCTACGCCCGCATG 247
    ||||||||||||||||||||||||||||||||||||||||||||||||||
651 CGATGGCGGTCTATGGTGAGGTGGGTGTGAGGGTCGTCTACGCCCGCATG 700

248 TTCTTTGATCGGATGGACGGGCGCATTCAAGGGTATGTGGACGCCTTGAA 297
    ||||||||||||||||||||||||||||||||||||||||||||||||||
701 TTCTTTGATCGGATGGACGGGCGCATTCAAGGGTATGTGGACGCCTTGAA 750

298 GGCTCGCTCTCCCCAAGTCGAACTGTGCTCGATCATGGANGAAACNGCTG 347
    |||||||||||||||||||||||||||||||||||||||:||||:||||
751 GGCTCGCTCTCCCCAAGTCGAACTGTGCTCGATCATGGAGGAAACGGCTG 800

348 TGGCCAAAGATCGGATCACANCCCTGTCANATCANTATCATGGCACNGCA 397
    ||||||||||||||||||||:|||||||||:||||:|||||||||||:|||
801 TGGCCAAAGATCGGATCACAGCCCTGTCAGATCAGTATCATGGCACGGCA 850

398 NGAGGTCCTATATCANTTTGGCCCGCTCCTGCCACTACCACNGCGGTGAC 447
    :||||||  |||||||:||||||||||||||||||||||||:|||||||
851 GGAGGTCGTATATCAGTTTGGCCCGCTCCTGCCACTACCACGGCGGTGAC 900

448 ATTTAAANGAATCCATGGGCCA....ACCTCCCCGTGATCCGGCGGTAA 493
    | || ||:|||| |  || ||      | || ||||||||| |||||||
901 AGTTGAAGGAATGCGATGGGCACAAGCCTTCGCCCGTGATCGGGCGGTAA 950

494 TGTGAC....................................... 499
    ||||
951 TGTGGACGCTTCACATGGCGGAGAGCGATCATGATGAGCGGATTCATGGG 1000
```

*Fig. 5B*

```
 360 ......................TNGCAGGTTGTGAGCA..TGCTACTTC  336
                          |:|||||||||||||   |||| ||
1101 ACCGCCACAATGTGAAGGTCGCGTCGCAGGTTGTGAGCAATGCCTACCTC 1150

335 GGTTCAGGNGTGGCCCCCGTGCCAGAGATGGTGGAGCGCGGCATGGCCGT  286
     || ||||:|||||||||||||||||||||||||||||||||||||||||
1151 GGCTCAGGGGTGGCCCCCGTGCCAGAGATGGTGGAGCGCGGCATGGCCGT 1200

285 GGGCATTGGAACAGATAACGGGAATAGTAATGACTCCGTAAACATGATCG  236
     |||||||||||||||||||||||||||||||||||| |||||||||||
1201 GGGCATTGGAACAGATAACGGGAATAGTAATGACTCCGCAAACATGATCG 1250

235 GAGACATGAAGTTTATGGCCCATATTCACCGCGCGGTGCATCGGGATGCG  186
     |||||||||||||||||||||||||||||||||||||||||||||||||
1251 GAGACATGAAGTTTATGGCCCATATTCACCGCGCGGTGCATCGGGATGCG 1300

185 GACGTGCTGACCCCAGAGAAGATTNTTGAAATGGCGACGATCGATGGGGC  136
     ||||||||||||||||||||||||:|||||||||||||||||||||||||
1301 GACGTGCTGACCCCAGAGAAGATTCTTGAAATGGCGACGATCGATGGGGC 1350

135 GCGTTTCGTTGGGGATGGACCACGAGATTGGTTCCATCGAAACCGGCAAG   86
     ||| ||||||||| ||||||||||||||||||||||||||||||||||
1351 GCG.TTCGTTGGGAATGGACCACGAGATTGGTTCCATCGAAACCGGCAAG 1399

85 CGCGCGGACCTTATCCTGCTTGACCTGCGTCACCCTCAGACGACTCCTCA   36
     |||||||||||||||||||||||||||||| |||||||||||||
1400 CGCGCGGACCTTATCCTGCTTGACCTGCGTCA.CCTCAGACGACTC..TC 1446

35 CCATCATTTGGCGGCCACGATCGTGTTTCAGGCTT...............    1
     ||||||||||||||||||||||||||||||||||
1447 ACATCATTTGGCGGCCACGATCGTGTTTCAGGCTTACGGCAATGAGGTGG 1496
```

*Fig. 5C*

```
   1 .......CGGCCACGATCGTGTTTCAGGCTTACGGCAATGAGGTGGACAC 43
           ||||||||||||||||||||||||||||||||||||||||||||||
1451 CATTTGGCGGCCACGATCGTGTTTCAGGCTTACGGCAATGAGGTGGACAC 1500

44 TGTCCTGATTGACGGAAACGTTGTGATGGAGAACCGCCGCTTGAGCTTTC 93
     ||||||||||||||||||||||||||||||||||||||||||||||||||
1501 TGTCCTGATTGACGGAAACGTTGTGATGGAGAACCGCCGCTTGAGCTTTC 1550

94 TTCCCCTGAACGTGAGTTGGCGTTCCTTGAGGAAGCGCAGAGCCGCGCC 143
     ||||||||||||||||||||||||||||||||||||||||||||||||||
1551 TTCCCCTGAACGTGAGTTGGCGTTCCTTGAGGAAGCGCAGAGCCGCGCC 1600

144 ACAGCTATTTTGCATCGGGCGAAACATGGTGGCTAACCCAGCTTGGCGCA 193
     |||||||||||| |||||| ||||||||||||||||||||||||||||||
1601 ACAGCTATTTTGCAGCGGGCG.AACATGGTGGCTAACCCAGCTTGGCGCA 1649

194 GCCTCTAGGAAATGACGCCGTTGCTGCATCCGCCGCCCCTTGAGGAAATC 243
     ||||||||||||||||||||||||||||||||||||||||||||||||||
1650 GCCTCTAGGAAATGACGCCGTTGCTGCATCCGCCGCCCCTTGAGGAAATC 1699

244 GCTGCCATCTTGGCGCGGCTCGGATTGGGGGGCGGACATGACCTTGATGG 293
     ||||||||||||||||||||||||||||||||||||||||||||||||||
1700 GCTGCCATCTTGGCGCGGCTCGGATTGGGGGGCGGACATGACCTTGATGG 1749

294 ATACAGAATTGCCATGAATGCGGCACTTCCGTCCTTCGCTCGTGTGGAAT 343
     ||||||||||||||||||||||||||||||||||||||||||||||||||
1750 ATACAGAATTGCCATGAATGCGGCACTTCCGTCCTTCGCTCGTGTGGAAT 1799

344 CGTTGGTAGGTGAGGGTCGACTGCGGGCGCCAGCTTCCCGAAGAGGTGAA 393
     ||||||||||||||||||||||||||||||||||||||||||||||||||
1800 CGTTGGTAGGTGAGGGTCGACTGCGGGCGCCAGCTTCCCGAAGAGGTGAA 1849

394 AGCCCGAGGATCCTCTAGAGTCCGATTTTTCCGATGTCATCACCGGCGCG 443
     || ||   |
1850 AGGCCCGAG.......................................  1858
```

*Fig. 5D*

```
  1 ...CCTGCGCGGA.GGCCTCCGCACGGGCGTCAATTCTATGACTGGCTGT  46
        ||||||||||  ||||  |||||||| |||||||||||||||||||||
451 CCTCCTGCGCGGAGGGCCCTCGCACGGACGTCAATTCTATGACTGGCTGT 500

47 TCAACGTTGTGTATCCGGGACAAAAGGCGATGAGACCGGAGGACGTANCG  96
    ||||||||||||||||||||||||||||||||||||||||||||||:||
501 TCAACGTTGTGTATCCGGGACAAAAGGCGATGAGACCGGAGGACGTAGCG 550

97 GTGGCGGTGAGGTTGTATTGTGCGGAAGCTGTGCGCAGCGGGATTACGAC 146
    ||||||||||||||||||||||||||||||||||||||||||||||||||
551 GTGGCGGTGAGGTTGTATTGTGCGGAAGCTGTGCGCAGCGGGATTACGAC 600

147 GATCAACGAAAACGCCGATTCGGCCATCTACCCAGGCAACATCGAGGCCG 196
    ||||||||||||||||||||||||||||||||||||||||||||||||||
601 GATCAACGAAAACGCCGATTCGGCCATCTACCCAGGCAACATCGAGGCCG 650

197 CGATGGCGGTCTATGGTGAGGTGGGTGTGAGGGTCGTCTACGCCCGCATG 246
    ||||||||||||||||||||||||||||||||||||||||||||||||||
651 CGATGGCGGTCTATGGTGAGGTGGGTGTGAGGGTCGTCTACGCCCGCATG 700

247 TTCTTTGATCGGATGGACGGGCGCATTCAAGGGTATGTGGACGCCTTGAA 296
    ||||||||||||||||||||||||||||||||||||||||||||||||||
701 TTCTTTGATCGGATGGACGGGCGCATTCAAGGGTATGTGGACGCCTTGAA 750

297 GGCTCGCTCTCCCCAAGTCGAACTGTGCTCGATCATGGAGGAAACGGCTG 346
    ||||||||||||||||||||||||||||||||||||||||||||||||||
751 GGCTCGCTCTCCCCAAGTCGAACTGTGCTCGATCATGGAGGAAACGGCTG 800

347 TGGCCAAAGATCGGATCACANCCCTGTCAGATCANTATCATGGCACGGCA 396
    ||||||||||||||||||||:||||||||||||:||||||||||||||||
801 TGGCCAAAGATCGGATCACAGCCCTGTCAGATCAGTATCATGGCACGGCA 850

397 NGAGGTCCTATATCANTTTGGCCCGCTCCTGCCACTACCACNGCGGTGAC 446
    :||||||  |||||||:|||||||||||||||||||||||||:|||||||
851 GGAGGTCGTATATCAGTTTGGCCCGCTCCTGCCACTACCACGGCGGTGAC 900

447 ATTTNAANGAATTCCATNGCACAA.CCTTCCCCCGTGATCNGGCGGTAA  495
    |  ||:||:||||  ||:|||||| |||||  ||||||||:||||||||
901 AGTTGAAGGAATGCGATGGCACAAGCCTTCGCCCGTGATCGGGCGGTAA  950

496 TGTNGACCCA........................................ 505
    |||:||| |
951 TGTGGACGCTTCACATGGCGGAGAGCGATCATGATGAGCGGATTCATGGG 1000
```

Fig. 6

| Bacterium | Translation of PCR amplified DNA sequence | | | | |
|---|---|---|---|---|---|
| | 79 | 92 | | | |
| ADP | SHGRQ | FYDWLFNVVY | PGQKAMRPED | VAVAVRLYCA | EAVRSGITTI |
| SG1 | PHGRQ | FYDWLFNVLY | PGQKAMRPED | VAVAVRLYCA | EAVRSGITTI |
| M91-3 | SHGRQ | FYDWLFNVLY | PGQKAMRPED | VAVAVRLYCA | EAVRSGITTI |
| J14a | PHGRQ | FYDWLFNVVY | PGQKAMRPED | VAVAVRLYCA | EAVRSGITTI |
| 38/38 | SHGRQ | FYDWLFNVLY | PGQKAMRPED | VAVAVRLYCA | EAVRSGITTI |
| Clav. | SHGRQ | FYDWLFNVVY | PGQKAMRPED | VAVAVRLYCA | EAVRSGITTI |
| | 125 | | | | 170 |
| ADP | NE.NADSAIY | PGNIEAAMAV | YGEVGVRVVY | ARMFFDRMDG | RIQGYVDALK |
| SG1 | NE.NADSAIY | PGNIEAAMAV | YGEVGVRVVY | ARMFFDRMDG | RIQGYVDALK |
| M91-3 | NE.NADSAIY | PGNIEAAMAV | YGEVGVRVVY | ARMFFDRMDG | RIQGYVDTLK |
| J14a | NE.NADSAIY | PGNIEAAMAV | YGEVGVRVVY | ARMFFDRMDG | RIQGYVDALK |
| 38/38 | NENNADSAIY | PGNIEAAMAV | YGEVGVRVVY | ARMFFDRMDG | RIQGYVDTLK |
| Clav. | NE.NADSAIY | PGNIEAAMAV | YGEVGVRVVY | ARMFFDRMDG | RIQGYVDALK |
| ADP | ARSPQVELCS | IMEETAVAKD | RITALSDQYH | GTAGGRISVW | PAPATTTAVT |
| SG1 | ARSPQVELCS | IMEETAVAKD | RITALSDQYH | GTAGGRISVW | PAPATTTAVT |
| M91-3 | ARSPQVELCS | IMEETAVAKD | RITALSDQYH | GTAGGRISVW | PAPATTTAVT |
| J14a | ARSPQVELCS | IMEETAVAKD | RITALSDQYH | GTAGGRISVW | PAPATTTAVT |
| 38/38 | ARSPQVELCS | IMEETAVAKD | RITALSDQYH | GTAGGRISVW | PAPATTTAVT |
| CLav. | ARSPQVELCS | IMEETAVAKD | RITALSDQYH | GTAGGRISVW | PAPATTTAVT |

Fig. 9

DNA MOLECULES AND PROTEIN DISPLAYING IMPROVED TRIAZINE COMPOUND DEGRADING ABILITY

CROSS-REFERENCE TO RELATED APPLICATION

This application claims priority to PCT/US98/00944, file Jan. 16, 1998, which claims priority to United States Provisional Patent Application, U.S. Ser. No. 60/035,404, filed Jan. 17, 1997.

STATEMENT REGARDING GOVERNMENT RIGHTS

This invention was made with government support from the United States Department of Agriculture-BARD program, Grant No. 94-34339-112. The government may have certain rights in this invention.

BACKGROUND OF THE INVENTION

More than 8 million organic compounds are known and many are thought to be biodegradable by microorganisms, the principle agents for recycling organic matter on Earth. In this context, microbial enzymes represent the greatest diversity of novel catalysts. This is why microbial enzymes are predominant in industrial enzyme technology and in bioremediation, whether used as purified enzymes or in whole cell systems.

There is increased interest in engineering bacterial enzymes for improved industrial performance. For example, site directed mutagenesis of subtilisin has resulted in the development of enzyme variants with improved properties for use in detergents. Most applied enzymes, particularly those used in biodegrading pollutants, however, are naturally evolved. That is, they are unmodified from the form in which they were originally present in a soil bacterium.

For example, most bioremediation is directed against petroleum hydrocarbons, pollutants that are natural products and thus have provided selective pressure for bacterial enzyme evolution over millions of years. Synthetic compounds not resembling natural products are more likely to resist biodegradation and hence accumulate in the environment. This changes over a bacterial evolutionary time scale; compounds considered to be non-biodegradable several decades ago, for example PCBs and tetrachloroethylene, are now known to biodegrade. This is attributed to recent evolution and dispersal of the newly evolved gene(s) throughout microbial populations by mechanisms such as conjugative plasmids and transposable DNA elements.

A better understanding of the evolution of new biodegradative enzymes will reveal how nature cleanses the biosphere. Furthermore, the ability to emulate the process in the laboratory may shave years off the lag period between the introduction of a new molecular compound into the environment and the development of a dispersed microbial antidote that will remove it.

Atrazine [2-chloro-4-(ethylamino)-6-(isopropylamino)-1,3,5-triazine)] is a widely used s-triazine (i.e., symmetric triazine) herbicide for the control of broad-leaf weeds. Approximately 800 million pounds were used in the United States between 1980 and 1990. As a result of this widespread use, for both selective and nonselective weed control, atrazine and other s-triazine-containing compounds have been detected in ground and surface water in several countries.

Numerous studies on the enviromnental fate of atrazine have shown that atrazine is a recalcitrant compound that is transformed to $CO_2$ very slowly, if at all, under aerobic or anaerobic conditions. It has a water solubility of 33 mg/l at 27° C. Its half-life (i.e., time required for half of the original concentration to dissipate) can vary from about 4 weeks to about 57 weeks when present at a low concentration (i.e., less than about 2 parts per million (ppm)) in soil. High concentrations of atrazine, such as those occurring in spill sites have been reported to dissipate even more slowly.

As a result of its widespread use, atrazine is often detected in ground water and soils in concentrations exceeding the maximum contaminant level (MCL) of 3 $\mu$g/l (i.e., 3 parts per billion (ppb)), a regulatory level that took effect in 1992. Point source spills of atrazine have resulted in levels as high as 25 ppb in some wells. Levels of up to 40,000 mg/i (i.e., 40,000 parts per million (ppm)) atrazine have been found in the soil at spill sites more than ten years after the spill incident. Such point source spills and subsequent runoff can cause crop damage and ground water contamination.

There have been numerous reports on the isolation of s-triazine-degrading microorganisms (see, e.g., Behki et al., *J. Agric. Food Chem.*, 34, 746–749 (1986); Behki et al., *Appl. Environ. Microbiol.*, 59, 1955–1959 (1993); Cook, *FEMS Microbiol. Rev.*, 46, 93–116 (1987); Cook et al., *J. Agric. Food Chem.*, 29, 1135–1143 (1981); Erickson et al., *Critical Rev. Environ. Cont.*, 19, 1–13 (1989); Giardina et al., *Agric. Biol. Chem.*, 44, 2067–2072 (1980); Jessee et al., *Appl. Environ. Microbiol.*, 45, 97–102 (1983); Mandelbaum et al., *Appl. Environ. Microbiol.*, 61, 1451–1457 (1995); Mandelbaum et al., *Appl. Environ. Microbiol.*, 59, 1695–1701 (1993); Mandelbaum et al., *Environ. Sci. Technol.*, 27, 1943–1946 (1993); Radosevich et al., *Appl. Environ. Microbiol.*, 61, 297–302 (1995); and Yanze-Kontchou et al., *Appl. Environ. Microbiol.*, 60, 4297–4302 (1994)). Many of the organisms described, however, failed to mineralize atrazine (see, e.g., Cook, *FEMS Microbiol. Rev.*, 46, 93–116 (1987); and Cook et al., *J. Azric. Food Chem.*, 29, 1135–1143 (1981)). While earlier studies have reported atrazine degradation only by mixed microbial consortia, more recent reports have indicated that several isolated bacterial strains can degrade atrazine. In fact, research groups have identified atrazine-degrading bacteria classified in different genera from several different locations in the U.S. (e.g., Minnesota, Iowa, Louisiana, and Ohio) and Switzerland (Basel).

An atrazine-degrading bacterial culture, identified as Pseudomonas sp. strain ADP (Mandelbaum et al., *Appl. Environ. Microbiol.*, 61, 1451–1457 (1995); Mandelbaum et al., *Appl. Environ. Microbiol.*, 59, 1695–1701 (1993); de Souza et al., *J. Bact.*, 178, 4894–4900 (1996); and Mandelbaum et al., *Environ. Sci. Technol.*, 27, 1943–1946 (1993)), was isolated and was found to degrade atiazine at concentrations greater than about 1,000 $\mu$g/ml under growth and non-growth conditions. See also, Radosevich et al., *Appl. Environ. Microbiol.*, 61, 297–302 (1995) and Yanze-Kontchou et al., *Appl. Environ. Microbiol.*, 60, 4297–4302 (1994). Pseudomonas sp. strain ADP (Atrazine Degrading Pseudononas) uses atrazine as a sole source of nitrogen for growth. The organism completely mineralizes the s-triazine ring of atrazine under aerobic growth conditions. That is, this bacteria is capable of degrading the s-triazine ring and mineralizing organic intermediates to inorganic compounds and ions (e.g., $CO_2$).

The genes that encode the enzymes for MELAMINE (2,4,6-triamino-s-triazine) metabolism have been isolated from a Pseudomonas sp. strain. The genes that encode atrazine degradation activity have been isolated from Rhodococcus sp. strains; however, the reaction results in the dealkylation of atrazine. In addition, the gene that encodes atrazine dechlorination has been isolated from a Pseudomonas sp. strain. See, for example, de Souza et al., *Appl. Environ. Microbiol.*, 61, 3373 (1995). The protein expressed by the gene disclosed by de Souza et al., degrades atrazine, for example, at a $V_{max}$ of about 2.6 μmol of hydroxyatrazine per min per mg protein. Although this is significant, it is desirable to obtain genes and the proteins they express that are able to dechlorinate triazine-containing compounds with chlorine moieties at an even higher rate and/or under a variety of conditions, such as, but not limited to, conditions of high temperature (e.g., at least about 45° C. and preferably at least about 65° C.), various pH conditions, and/or under conditions of high salt content (e.g., about 20–30 g/L), or under other conditions in which the wild type enzyme is not stable, efficient, or active. Similarly, it is desirable to obtain genes and proteins encoded by these genes that degrade triazine-containing compounds such as those triazine containing compounds available under the trade names; "AMETRYN", "PROMETRYN", "CYANAZINE", "MELAMINE", "SIMAZINE", as well as TERBUTHYLAZINE and desethyldesisopiopylatriazine. It is also desirable to identify proteins expressed in organisms that degrade triazine-containing compounds in the presence of other nitrogen sources such as ammonia and nitrate.

SUMMARY OF THE INVENTION

The present invention provides isolated and purified DNA molecules that encode atrazine degrading enzymes similar to, but having different catalytic activities from a wild type (i.e. from an isolated but naturally occurring atrazine chlorohydrolase). The term "altered enzymatic activities" is used to refer to homologs of atrazine chlorohydrolase having altered catalytic rates as quantitated by $k_{cat}$ and $K_m$, improved ability to degrade atrazine, altered substrate ranges, altered activities as compared to the native sequence in aqueous solutions, altered stability in solvents, altered active temperature ranges or altered reaction conditions such as salt concentration, pH, improved activity in a soil environment, and the like, as compared with the wild-type atrazine chlorohydrolase (AtzA) protein.

In one preferred embodiment, the present invention provides DNA fragments encoding a homolog of atrazine chlorhydrolase and comprising the sequence selected from the group consisting of SEQ ID NO:3, SEQ ID NO:4, SEQ ID NOS:7–11 and SEQ ID NOS: 17–21. In one embodiment the invention relates to these DNA fragments in a vector, preferably an expression vector. Further, the invention relates to the DNA fragment in a cell. In one embodiment the cell is a bacterium and in a preferred embodiment, the bacterium is *E. coli*.

The invention also relates to s-triazine-degrading proteins hlaving at least one amino acid different from the protein of SEQ ID NO:2, wherein the coding region of the nucleic acid encoding the s-triazine degrading protein has at least 95% homology to SEQ ID NO:1 and wherein the s-triazine-degrading protein has an altered catalytic activity as compared with the protein having the sequence of SEQ ID NO:2. In one embodiment, the protein is selected from the group consisting of SEQ ID NOS:5, 6 and 22–26. In one embodiment the substrate for the s-triazine degrading protein is ATRAZINE. In another embodiment the substrate for the s-triazine degrading protein is TERBUTHYLAZINE and in yet another embodiment the substrate for the s-triazine degrading protein is MELAMINE. In another embodiment this invention relates to a remediation composition comprising a cell producing at least one s-triazine-degrading protein having at least one amino acid different from the protein of SEQ ID NO:2, wherein the coding region of the nucleic acid encoding the s-triazine degrading protein has at least 95% homology to SEQ ID NO:1 and wherein the s-triazine-degrading protein has an altered catalytic activity as compared with the protein having the sequence of SEQ ID NO:2. In a preferred embodiment the composition is suitable for treating soil or water. In another embodiment the remediation composition comprises at least one s-triazine-degrading protein having at least one amino acid different from the protein of SEQ ID NO:2, wherein the coding region of the nucleic acid encoding the s-triazine degrading protein has at least 95% homology to SEQ ID NO:1 and wherein the s-triazine-degrading protein has an altered catalytic activity as compared with the protein having the sequence of SEQ ID NO:2. In a preferred embodiment this composition is also suitable for treating soil or water. In one embodiment the remediation composition comprises the protein bound to an immobilization support. In yet another embodiment, these proteins are homotetramers, such as the homotetramers formed by AtzA.

In another embodiment the invention relates to a protein selected from the group consisting of proteins comprising the amino acid sequences of SEQ ID NOS:5, 6 and 22–26.

In another aspect of this invention, the invention relates to a DNA fragment having a portion of its nucleic acid sequence having at least 95% homology to a nucleic acid sequence consisting of position 236 and ending at position 1655 of SEQ ID NO:1, wherein the DNA fragment is capable of hybridizing under stringent conditions to SEQ ID NO:1 and wherein there is at least one amino acid change in the protein encoded by the DNA fragment as compared with SEQ ID NO:2 and wherein the protein encoded by the DNA fragment is capable of dechlorinating at least one s-triazine-containing compound and has a catalytic activity different from the enzymatic activity of the protein of SEQ ID NO:2. In one embodiment the s-triazine-containing compound is ATRAZINE, TERBUTHYLAZINE, or MELAMINE. In one embodiment.

The invention also relates to a method for treating a sample comprising an s-triazine containing compound comprising the step of adding a adding a protein to a sample comprising an s-triazine-containing compound wherein the protein is encoded by gene having at least a portion of the nucleic acid sequence of the gene having at least 95% homology to the sequence beginning at position 236 and ending at position 1655 of SEQ ID NO:1, wherein the gene is capable of hybridizing under stringent conditions to SEQ ID NO:1, wherein there is at least one amino acid change in the protein encoded by the DNA fragment as compared with SEQ ID NO:2 and wherein the protein has an altered catalytic activity as compared to the protein having the amino acid sequence of SEQ ID NO:2. In one embodiment, the composition comprises bacteria expressing the protein. In one embodiment the s-triazine-containing compound is atrazine, in another the s-triazine-containing compound is TERBUTHYLAZINE and in another the s-triazine containing compound is (2,4,6-triamino-s-triazine). In one embodiment, the protein encoded by the gene is selected from the group consisting of SEQ ID NOS:5, 6 and 22–26.

In another aspect, this invention relates to a method for obtaining homologs of an atrazine chlorohydrolase comprising the steps of obtaining a nucleic acid sequence encoding atrazine chlorohydrolase, mutagenizing the nucleic acid to obtain a modified nucleic acid sequence that encodes for a protein having an amino acid sequence with at least one amino acid change relative to the amino acid sequence of the atrazine chlorohydrolase, screening the proteins encoded by the modified nucleic acid sequence; and selecting proteins with altered catalytic activity as compared to the catalytic activity of the atrazine chlorohydrolase. Preferably, the atrazine chlorohydrolase nucleic acid sequence is SEQ ID NO:1. In one embodiment the altered catalytic activity is an improved ability to degrade ATRAZINE. In another embodiment, the altered catalytic activity is an altered substrate activity.

Other homologs with an improved rate of catalytic activity for atrazine include clones A40, A42, A44, A46 and A60 having nucleic acid sequences (SEQ ID NOS:17–21, respectively). Other homologs capable of better degrading TERBUTHYLAZINE include A42, A44, A46 and A60 as well as A1 and A13.

BRIEF DESCRIPTION OF THE DRAWINGS

FIGS. 1A–C. Nucleotide sequence alignment of wild type atzA (bottom sequence) from Pseudomonas sp. strain ADP and clone (A7) (SEQ ID NO:1 and SEQ ID NO:3).

FIGS. 2A–C. Nucleotide sequence alignment of wild type atzA (bottom sequence) from Pseudomonas sp. strain ADP and clone (T7) (SEQ ID NO:1 and SEQ ID NO:4).

FIG. 3. Amino acid sequence alignment of wild type AtzA (bottom sequence) from Pseudomonas sp. strain ADP and clone (A7) (SEQ ID NO:2 and SEQ ID NO:5).

FIG. 4. Amino acid sequence alignment of wild type AtzA from Pseudomonas sp. strain ADP and clone (T7) (SEQ ID NO:2 and SEQ ID NO:6).

FIGS. 5A–D. Nucleotide sequence alignment of wild type atzA (SEQ ID NO:1 bottom sequence) from Pseudonionas sp. strain ADP and clone (A11). FIG. 5(a) provides the sequence from nucleic acids 11–543 (SEQ ID NO:7), FIG. 5(b) provides the sequence from nucleic acids 454–901 (SEQ ID NO:8), FIG. 5(c) provides the sequence from 1458–1851 (SEQ ID NO:9; N in this sequence indicates that this nucleotide has not been verified) and FIG. 5(d) provides the sequence from nucleic acids 1125–1482 (SEQ ID NO:10) of clone A11. The "N" in these sequences refer to nucleic acids that are being verified.

FIG. 6. Nucleotide sequence alignment of a portion of the nucleic acid sequence of wild type atzA from Pseudomonas sp. strain ADP and nucleic acids 436–963 of clone (A13) (SEQ ID NO:11 and SEQ ID NO:1).

FIG. 7(a) illustrates the % of TERBUTHYLAZINE remaining after exposure to AtzA or a homolog.

FIG. 8(a) provides the % of TERBUTHYLAZINE remaining after a 15 minute exposure to the homolog in the presence or absence of the metals and additives of Samples 1–10.

FIG. 9. is a comparison of PCR amplified fragments using two primers of the atrazine hydrochlorase gene from 6 different types of bacteria; Pseudomonas sp. strain ADP; Ralstonia strain M91-3; Clavibacter (Clav.); Agrobacterium strain J14(a); ND (an organism with no genus assigned) strain 38/38; and Alcaligenes strain SG1 (SEQ ID NOS:12–16).

DETAILED DESCRIPTION OF THE INVENTION

Figure 7A:
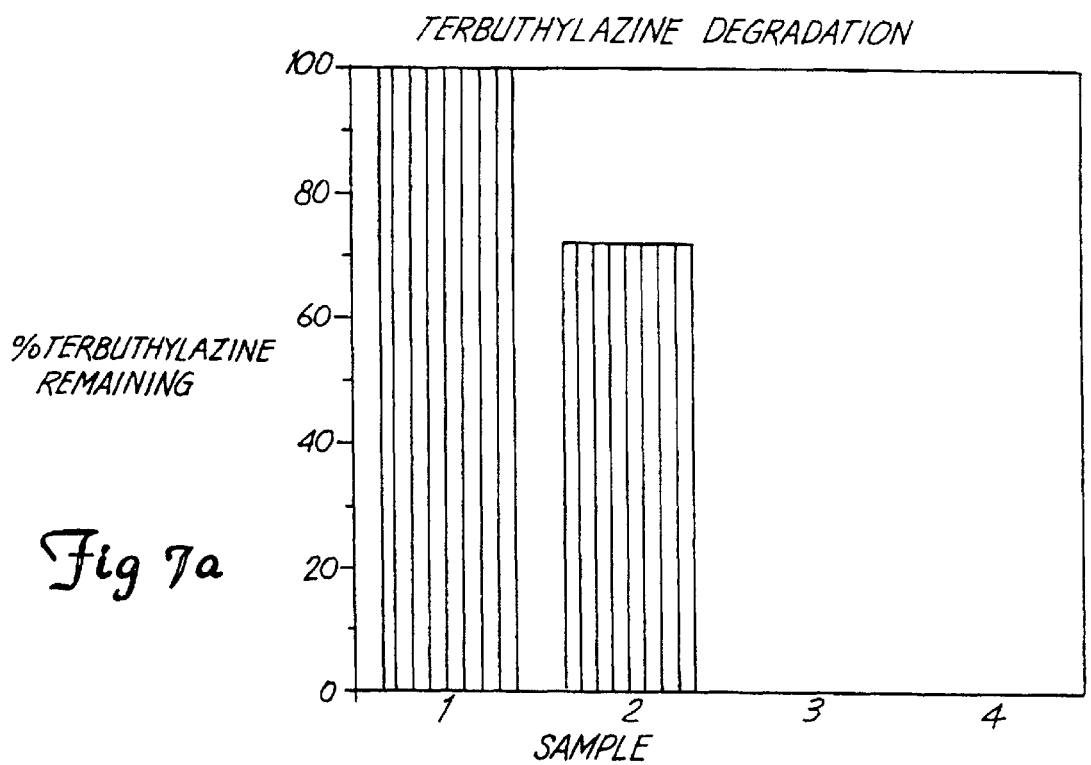
FIGS. 7A and B. is a histogram illustrating the TERBUTHYLAZINE degradative ability of two homologs of this invention (T7=sample 3 and A7=sample 4).

The present invention provides isolated and purified DNA molecules, and isolated and purified proteins, involved in the degradation of s-triazine-containing compounds. The proteins encoded by the genes of this invention are involved in the dechlorination and/or the deamination of s-triazine-containing, compounds. The wild type AtzA protein can catalyze the dechlorinationi of s-triazine-containing compounds but not the deamination of these compounds. The dechlorination reaction occurs on s-triazine containing compounds that include a chlorine atom and at least one alkylamino side chain. Such compounds have the following general formula:

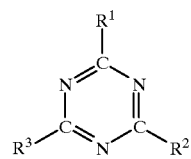

wherein $R^1$=Cl, $R^2$=$NR^4R^5$ (wherein $R^4$ and $R^5$ are each independently H or a $C_{1-3}$ alkyl group), and $R^3$=$NR^6R^7$ (wherein $R^6$ and $R^7$ are each independently H or a $C_{1-3}$ alkyl group), with the proviso that at least one of $R^2$ or $R^3$ is an alkylamino group. As used herein, an "alkylamino" group refers to an amine side chain with one or two alkyl groups attached to the nitrogen atom. Examples of such compounds include atrazine (2-chloro-4-ethylamino-6-isopropylamino-1,3,5-s-triazine), desethylatrazine (2-chloro-4-amino-6-isopropylamino-s-triazine), desisopropylatrazine (2-chloro-4-ethylamino-6-amino-s-triazine), and SIMAZINE (2-chloro-4,6-diethylamino-s-triazine).

Triazine degradation activity is encoded by a gene that is localized to a 21.5-kb EcoRl fragment, and more specifically to a 1.9-kb AvaI fragment, of the genome of Pseudomonas sp. ADP (ADP is strain designiation for Atrazine-degrading Pseudomonas) bacterium. Specifically, these genomic fragments encode proteins involved in s-triazine dechlorination. The rate of degradation of atrazine that results from the expression of these fragments in E. coli is comparable to that seen for native Pseudomonas sp. strain ADP; however, in contrast to what is seen with native Pseudomonas sp. strain ADP, this degradation in E. coli is unaffected by the presence of inorganic nitrogen sources like ammonium chloride. This is particularly advantageous for regions contaminated with nitrogen-containing fertilizers or herbicides, for example. The expression of atrazine degradation activity in the presence of inorganic nitrogen compounds broadens the potential use of recombinant organisms for biodegradation of atrazine in soil and water.

Hydroxyatrazine formation in the environment was previously thought to result solely from the chemical hydrolysis of atrazine (Armstrong et al., Environ. Sci. Technol., 2, 683–689 (1968); deBruijn et al., Gene, 27, 131–149 (1984); and Nair et al., Environ. Sci. Technol., 26, 1627–1634 (1992)). Previous reports suggest that the first step in atrazine degradation by environmental bacteria is dealkylation. Dealkylation produces a product that retains the chloride moiety and is likely to retain its toxicity in the environment. In contrast to these reports, AtzA dechlorinates atrazine and produces a detoxified product in a one-step detoxification reaction that is amenable to exploitation in the remediation industry. There remains a need for atrazine-degrading enzymes with improved activity.

As used herein, the gene encoding a protein capable of dechlorinating atrazine and originally identified in Pseudomonas sp. strain ADP and expressed in E. coli is referred to as "atzA", whereas the protein that it encodes is referred to as "AtzA." Examples of the cloned wild type gene sequence and the amino acid sequence derived from the gene sequence are provided as SEQ ID NO:1 and SEQ ID NO:2 respectively. As also used herein, the terms atrazine chlorohydrolase (AtzA) protein, atrazine chlorohydrolase enzyme, or simply atrazine chlorohydrolase, are used interchangeably, and refer to an atrazine chlorohydrolase enzyme involved in the degradation of atrazine and similar molecules as discussed above.

A "homolog" of atrazine chlorohydrolase is an enzyme derived from the gene sequence encoding atrazine chlorohydrolase where the protein sequence encoded by the gene is modified by amino acid deletion, addition, substitution, or truncation but that nonetheless is capable of dechlorinating or deaminating s-triazine containing compounds. In addition, the homolog of atrazine chlorohydrolase (AtzA) has a nucleic acid sequence that is different from the atzA sequence (SEQ ID NO:1) and produces a protein with modified biological properties or, as used herein, "altered enzymatic activities." These homologs include those with altered catalytic rates as quantitated by $k_{cat}$ and $K_m$, altered substrate ranges, altered activities as compared to the native sequence in aqueous solutions, altered stability in solvents, altered active temperature ranges or altered reaction conditions such as salt concentration, pH, improved activity in a soil environment. and the like, as compared with the wild-type atrazine chlorolhydrolase (AtzA) protein. Thus, provided that two molecules possess enzymatic activity to an s-triazine-containing substrate and one molecule has the gene sequence of atzA (SEQ ID NO:1), the other is considered a homolog of that sequence where 1) the gene sequence of the homolog differs from SEQ ID NO:1 such that there is at least one amino acid change in the protein encoded by SEQ ID NO:1 (i.e., SEQ ID NO:2); 2) the homolog has different enzymatic characteristics from the protein encoded by SEQ ID NO:1 such as, but not limited to, an altered substrate preference, altered rate of activity, or altered conditions for enzymatic activity such as temperature, pH, salt concentration or the like, as discussed supra; and 3) where the coding region of the nucleic acid sequence encoding the variant protein has at least 95% homology to SEQ ID NO:1.

As used herein, the terms "isolated and purified" refer to the isolation of a DNA molecule or protein from its natural cellular environment, and from association with other coding regions of the bacterial genome, so that it can be sequenced, replicated, and/or expressed. Preferably, the isolated and purified DNA molecules of the invention comprise a single coding region. Thus, the present DNA molecules are preferably those consisting of a DNA segment encoding a homolog of atrazine chlorohydrolase.

Using the nucleic acid encoding the wild-type atzA sequence and the amino acid sequence of the wild-type enzyme AtzA, similar atrazine degrading enzymes were identified in other bacteria. In fact, sequencing of the atzA gene in the other bacteria demonstrated a homology of at least 99% to the atzA sequence, suggesting little evolutionary drift (see SEQ ID NOS:12–16). Homologs of the atzA gene could not be identified in the genomes of bacteria that did not metabolize atrazine. This information supports the theory that the atzA gene evolved to metabolize s-triazine-containing compounds.

The studies assessing the prevalence and homology of the atzA gene in a variety of bacterial genera also suggest that atra is likely to be a relatively young, i.e. recently evolved gene. That the gene is recently evolved is supported by the attributes of the gene and the protein encoded by the gene. For example: (i) the gene has a limited s-triazine range that includes atrazine and the structurally analogous herbicide SIMAZINE, but does not act on all s-triazines; (ii) the gene has a high sequence homology to genes isolated from other bacteria that produce proteins with atrazine-degrading activity; (iii) is not organized with the atzB and atzC genes in a contiguous arrangement such as an operon; (iv) the gene lacks the type of coordinate genetic regulation seen, for example, in aromatic hydrocarbon biodegradative pathway genes; (v) the wild-type gene was isolated from a spill site containing high atrazine levels and (vi) it is suggested to have been environmentally undetectable until the last few years.

Genes involved in reactions common to most bacteria and mammals are more highly evolved and have attained catalytic proficiency closer to theoretical perfection. Genes that have evolved more recently have not had the evolutionary opportunity to maximize the level of catalytic efficiency that they could theoretically obtain. These enzymes are suboptimal. Suboptimal enzymes include enzymes that have a second order rate constant, $k_{cat}/K_M$, that is orders of magnitude below the diffusion-controlled limit of enzyme catalysis, $3 \times 10^8$ $M^{-1}s^{31\ 1}$. These enzymes have the potential to evolve higher $k_{cat}$, lower $K_m$, or both. Enzymes with higher $k_{cat}$, lower $K_m$, or both would appear to have selective advantage as a biodegradative enzyme because less enzyme with higher activity would serve the same metabolic need and conserve ATP expended in enzyme biosynthesis. Optimized enzymes have the further advantage of having an improved commercial value resulting from their improved efficiency or improved activity under a defined set of conditions.

Thus, the alzA gene is, potentially, an s-triazine compound-degrading progenitor with the potential for improvement and modification. AtzA is a candidate for studies to generate homologs with improved activity, i.e., enhanced rate, altered pH preference, salt concentration and the like. The $k_{cat}/K_M$ for atrazine chlorohydrolase purified from Pseudomnonias ADP is $5 \times 10^5$ $M^{-1}s^{-1}$, 3 orders of magnitude below the theoretical catalytic limit. That all of the alzA homologous genes from a survey of atrazine-degrading bacteria are so structurally and catalytically similar suggest that the atza gene and the AtzA protein can be improved and will be improved naturally over time. Indeed, most biodegradative enzymes are orders of magnitude below diffusion limiting enzyme rates and, under this hypothesis, are also candidates for gene and protein modifications.

In one embodiment of this invention, a method is disclosed for selecting or screening modified and improved atzA gene sequences that encode protein with improved enzymatic activity, whether the activity is enzymatic rate, using atrazine as a substrate, as compared to the wild-type sequence, or improved activity under any of a variety of reaction conditions including, but not limited to, elevated temperature, salt concentration, altered substrate range, solvent conditions, pH ranges, tolerance or stability to a variety of environmental conditions, or other reaction conditions that may be useful in bioremediation processes. The method preferably includes the steps of obtaining the wild-type atzA gene sequence, mutagenizing the gene sequence to obtain altered atzA sequences, selecting or screening for clones expressing altered AtzA activity and selecting gene sequences encoding AtzA protein with improved s-triazine-degrading activity.

As a first step for practicing the method of this invention, the wild-type atzA sequence (SEQ ID NO:1) is incorporated into a vector or into nucleic acid that is suitable for a particular mutagenesis procedure. The wild type atzA gene was first obtained as a 1.9-kb AvaI genomic fragment that encodes an enzyme that transforms atrazine to hydroxyatrazine, termed atrazine chlorohydrolase. Methods for obtaining this fragment are disclosed by de Souza et al. (*Appl. Environ. Microb.* 61:3373–3378, (1995)). The gene, alzA, has one large ORF (open reading frame) and produces a translation product of about 473 amino acids. A particularly constant portion of this gene appears to occur at position 236 and end at position 1655 of SEQ ID NO:1. The wild-type atzA gene from Pseudomnonias strain ADP includes 1419 nucleotides and encodes a polypeptide of 473 amino acids with an estimated M, of 52,421 and a pI of 6.6. The gene also includes a typical Pseudomonas ribosome binding site, beginning with GGAGA, located 11 bp upstream from the proposed start codon. A potential stop codon is located at position 1655.

The wild-type atzA sequence can be obtained from a variety of sources including a DNA library, containing either genomic or plasmid DNA, obtained from bacteria believed to possess the atzA DNA. Alternatively the original isolate identified as containing the atzA DNA is described in U.S. Pat. No. 5,508.193 and can be accessed as a deposit from the American Type Culture Collection (ATCC No. 55464 Rockville, Md.). Libraries can be screened using oligonucleotide probes, for example, to identify the DNA corresponding to SEQ ID NO:1. SEQ ID NO:1 can also be obtained by PCR (polymerase chain reaction) using primers selected using SEQ ID NO:1 and the nucleic acid obtained from the atzA-containing organism (ATCC No. 55464) deposited with the American Type Culture Collection.

Screening DNA libraries oi- amplifying regions from prokaryotic DNA using synthetic oligonucleotides is a preferred method to obtain the wild-type sequence of this invention. The oligonucleotides should be of sufficient length and sufficiently nondegenerate to minimize false positives. In a preferred strategy, the actual nucleotide sequence(s) of the probe(s) is designed based on regions of the atzA DNA, preferably outside of the reading frame of the gene (the translated reading frame begins at position 236 and ends at position 1655 of SEQ ID NO:1) that have the least codon redundancy.

Cloning of the open reading frame encoding atzA into the appropriate replicable vectors allows expression of the gene product, the AtzA enzyme. and makes the coding region available for further genetic engineering.

The types of mutagenesis procedures that are capable of generating a variety of gene sequences based on a parent sequence, atzA or a previously mutagenized or altered sequence of atzA, are lkown in the art and each method has a preferred vector format. In general, the mutagenesis procedures selected is one that generates at least one modified atzA sequence and preferably a population of modified atzA gene sequences. Selecting or screening procedures are used to identify preferred modified enzymes (i.e., homologs) from the pool of modified sequences.

There are a number of methods in use for creating mutant proteins in a library format from a parent sequence. These include the polymerase chain reaction (Leung, D. W. et al. *Technique* 1:11–15, (1989)), Bartel, D. P. et al. *Science* 261:1411–1418 (1993)), cassette mutagenesis (Arkin, A. et al. *Proc. Natl. Acad. Sci. USA* 89:7811–7815 (1992), Oliphant, A. R. et al., *Gene* 44:177–183 (1986), Hermes, J. D. et al., *Proc. Natl. Acad. Sci. USA* 87:696–700 (1990), Delgrave et al. *Protein Engineerinn* 6:327–331, (1993), Delgrave et al. *Bio/Technology* 1:1548–1552 (1993), and Goldman, E R et al., *Bio/Technology* 10: 1557–1561 (1992)), as well as methods that exploit the standard polymerase chain reaction, including, but not limited to, DNA recombination during in vitiro PCR (Meyerhans, A. et al., *Nucl. Acids Res.* 18:1687–1691 (1990), and Marton et al. *Nucl. Acids Res.* 19:2423–2426, 1991)), in vivo site specific recombination (Nissim et al. *EMBO J.* 13:692–698 (1994), Winter et al. *Ann. Rev. Immunol.* 12:433–55 (1994)), overlap extension and PCR (Hayashi et al. *Biotechniques* 17:310–315 (1994)), applied molecular evolution systems (Bock, L. C. et al., Nature 355:564–566 (1992), Scott, J. K. et al., *Science* 249: 386–390 (1990), Cwirla, S. E. et al. *Proc. Natl . Acad. Sci. USA* 87:6378–6382 (1990), McCafferty, J. et al. *Nature* 348:552–554 (1990)), DNA shuffling systems, including those reported by Stemmer et al. (*Nature* 370:389–391 (1994) and *Proc. Natl. Acad. Sci. (USA)* 91:10747–10751 (1994) and International Patent Application Publication Number WO 95/22625), and random in vivo recombination (see Caren et al. *Bio/Technology* 12: 433–55 (1994), Caloger et al. *FEMS Microbiology Lett.* 97:41–44 (1992), International Patent Application Publication Numbers WO91/01087, to Galizzi and WO90/07576 to Radman, et al.).

Preferably, the method produces libraries with large numbers of mutant nucleic acid sequences that can be easily screened or selected without undue experimentation. Those skilled in the art will recognize that screening and/or selection methods are well documented in the art and those of ordinary skill in the art will be able to use the cited methods as well as other references similarly describing the aforementioned methods to produce pools of variant sequences. Preferred strategies include methods for screening for degradative activity of the s-triazine-containing compound on nutrient plates containing the homolog-encoding bacteria or by use of colormetric assays to detect the release of chlorine ions. Preferred selection assays include methods for selecting for homolog-containing bacterial growth on or in a s-triazine containing medium.

In a preferred method of this invention, gene shuffling, also termed recursive sequence recombination, is used to generate a pool of mutated sequences of the atzA gene. In this method the atzA gene, alone or in combination with the atzB gene, is amplified, such as by PCR, or, alternatively, multiple copies of the gene sequence (atzA and atzB) are isolated and purified. The gene sequence is cut into random fragments using enzymes known in the art, including DNAase I. The fragments are purified and the fragments are incubated with single or double-stranded oligonucleotides where the oligonucleotides comprise an area of identity and an area of heterology to the template gene or gene sequence. The resulting mixture is denatured and incubated with a polymerase to produce annealing of the single-stranded fragments at regions of identity between the single-stranded fragments. Strand elongation results in the formation of a mutagenized double-stranded polynucleotide. These steps are repeated at least once. In this gene shuffling technique, recombination occurs between substantially homologous, but non-identical, sequences of the atzA gene. In the studies provided in Example 2, the atzB gene was not gene-shuffled.

In the technique, published by Stemmer et al. (*Nature*, supra), the reassembled product is amplified by PCR and cloned into a vector. Clones containing the shuffled gene are next used in selection or screening assays. Example 2 discloses the use of a gene shuffling technique to glencrate pools of modified atzA sequences. The gene shuffling technique of Example 2 was modified based on the Stemmer et al. references. In this technique, an entire plasmid containing the atzA and atzB gene in a vector was treated with DNAase I and fragments between 500 and 2000 bp were gel purified. The fragments were assembled in a PCR reaction as provided in Example 2.

Once intact gene sequences are reassembled, they are incorporated into a vector suitable for expressing protein encoded by the reassembled nucleic acid, or as provided in Example 1, where the gene sequences are already in a vector, the vector can be incorporated directly into an organism suitable for replicating the vector. The vector containing the atzA gene is also preferably incorporated into a host suitable for expressing the atzA gene. The host, generally an *E. coli* species, is used in assays to screen or select for clones expressing the AtzA protein under defined conditions. The type of organism can be matched to the mutagenesis procedure and in Example 2, a preferred organism was the *E. coli* strain NM522.

The assays suitable for use in this invention can take any of a variety of forms for determining whether a particular protein produced by the organism containing the variant atzA sequences expresses an enzyme capable of dechlorinating or deaminating s-triazine compounds. Therefore, the types of assays that could be used in this invention include assays that monitor the degradation of s-triazine-containing compounds including ATRAZINE, SIMAZINE or MELAMINE using any of a variety of methods including, but not limited to, HPLC analysis to assess substrate degradation; monitoring clearing of precipitable s-triazine containing substrates, such as atrazine or TERBUTHYLAZINE, on solid media by bacteria containing the homologs of this invention; growth assays in media containing soluble substrate, monitoring the amount of chlorine released, as described by Bergman et al., *Anal. Chem.*, 29, 241–243 (1957) or the amount of nitrogen released; evaluating the derivitized product using gas chromatography and/or mass spectroscopy, solid agar plate assays with varied salt, pH substrate, solvent, or temperature conditions, calorimetric assays such as those provided by Epstein, J. ("Estimation of Microquantitation of Cyanide", (1947) *Analytical Chemistry* 19(4):272–276) and Habig and Jakoby ("Assays for Differentiation of Glutathione s-transferases, *Methods in Enzymology* 77:398–405) as well as radiolabelled assays to assess, for example, the release of radiolabel as a result of enzymatic activity.

In a preferred assay, clones are tested for their ability to degrade s-triazine-containing compounds such as atrazine, SIMAZINE, TERBUTHYLAZFNE (2-chloro-4-(ethylamino)-6-(tertiary butyl-amino)-1,3,5-triazine), desethylatrazine, desisopropylatrazine, MELAMINE, and the like. In these assays, atrazine, or another insoluble s-triazine-containing substrate, is incorporated into a nutrient agar plate as the sole nitrogen source. Concentrations of atrazine or other s-triazine-containing compounds can vary in the plate from about 300 µg/ml to at least about 1000 µg/ml and in a preferred embodiment about 500 µg/ml atrazine is used on the plate. Many s-triazines are relatively insoluble compounds in water and a suspension in an agar plate produces a cloudy appearance. Bacteria capable of metabolizing the insoluble s-triazine-containing compounds produce a clearing on the cloudy agar plate. An exemplary assays is a modified assay disclosed by Mandelbaum et al. (*Appl. Environ. Microbiol.* 61:1451–1453, (1995)) and provided in Example 2. In these assays LB medium can be used with the atrazine because *E. coli* expressing AtzA homologs support atrazine-degrading activity in the presence of other nitrogen sources. The assay demonstrates atrazine degradation by observing clearing zones surrounding clones expressing homologs of AtzA.

Clones are selected from the insoluble substrate assay based on their ability to produce, for example, a clearing in the substrate-containing plates. Similarly, assay conditions can be modified such as, but not limited to, salt, pH, solvent, temperature, and the like, to select clones encoding AtzA homologs capable of degrading a substrate under a variety of test conditions. For example, the pH of the assay can be altered to a pH range of about 5 to about 9. These assays would likely use isolated homolog protein to permit an accurate assessment of the effect of pH. The assay, or a modification of the assay, suitable for elevated temperatures (such as a soluble assay) can employ elevated temperature ranges, for example, between about 50° to about 80° C. The assays can also be modified to include altered salt concentrations including conditions equivalent to salt concentrations of about 2% to at least about 5% and preferably less than about 10% NaCl.

Clones identified as having altered enzymatic activity as compared with the native enzyme are further assessed to rule out if the apparent enhanced activity of the enzyme is the result of a faster or more efficient AtzA protein production or whether the effect observed is the result of an altered atzA gene sequence. For example, in Example 2, the atza was expressed to a high level using pUC18 as a preferred method to rule out higher in vivo activity due to increased expression.

Once triazine-degrading colonies are identified with the desired characteristics, the AtzA homologs are isolated for further analysis. Clones containing putative faster enzyme(s) can be picked, grown in liquid culture, and the protein homolog can be purified, for example, as described (de Souza et al. *J. Bacteriology*, 178:4894–4900 (1996)). The genes encoding the homologs can be modified, as known in the art, for extracellular expression or the homologs can be purified from bacteria. An exemplary method for protein purification is provided in Example 4. In a preferred method, protein was collected from bacteria using ammonium sulfate precipitation and further purified by HPLC (see for example, de Souza et al., *App. Envir. Microbio.* 61:3373–3378 (1995)).

Using these methods, a number of homologs were identified. Homologs can be identified using the assays discussed in association with this invention including the precipitable substrate assays on solid agar as described by Mandelbaum, et al. (supra). Homologs identified using the methods of Example 2 were separately screened for atrazine-degrading activity, for enhanced TERBUTHYLAZINE-degradina activity and for activity against other s-triazine-containing compounds. An assay for TERBUTHYLAZINE degrading activity is provided in Example 6. Two homologs were found to have at least a 10 fold higher activity and contained 8 different amino acids than the native AtzA protein (A7 and T7, see FIGS. 1–4). A subsequent round of DNA shuffling starting with the homolog gene sequence yielded further improvements in activity (A11 and A13 corresponding to nucleic acid SEQ ID NOS:7–10 and SEQ ID NO:11 respectively). This enzyme and other AtzA homologs (clones A40, A42, A44, A46, A60 corresponding to nucleic acid SEQ ID NOS:17–21 and to protein SEQ ID NOS:22–26, respectively) represent catabolic enzymes modified in their biological activity. Preferred homologs identified in initial studies include A7, T7, A11, A44, and A46.

Homologs were also identified with altered substrate activity. Both homologs T7 and A7 were able to degrade TERBUTHYLAZINE better than the wild-type enzyme. Other homologs capable of degrading TERBUTHYLAZINE include A42, A44, A46 and A60.

Atrazine chlorohydrolase converts a herbicide to a nontoxic, non-herbicidal, more highly biodegradable compound and the kinetic improvement of the homologs has important implications for enzymatic environmental remediation of this widely used herbicide. Less protein is required to dechlorinate the same amount of atrazine. Importantly, the protein can also be used for degradation of the s-triazine-compound TERBUTHYLAZINE.

This invention also relates to nucleic acid and protein sequences identified from the homologs of this invention. Peptide and nucleic acid fragments of these sequences are also contemplated and those skilled in the art can readily prepare peptide fragments, oligonucleotides, probes and other nucleic acid fragments based on the sequences of this invention. The homologs of this invention include those with an activity different from the native atrazine chlorohydrolase (AtzA) protein. As noted stipra. an activity that is different from the native atrazine chlorohydrolase protein includes enzymatic activity that is improved or is capable of functioning under different conditions such as salt concentration, temperature, altered substrate, or the like. Preferably, the DNA encoding the homologs hybridize to a DNA molecule complementary to the wild-type coding region of a DNA molecule encoding wild-type AtzA protein, such as the sequence provided in SEQ ID NO:1, under high to moderate stringency hybridization conditions. The homologs preferably have a homology of at least 95% to SEQ ID NO:1. As used herein, "high stringency hybridization conditions" refers to, for example, hybridization conditions in buffer containing 0.25 M $Na_2HPO_4$ (pH 7.4), 7% sodium dodecyl sulfate (SDS), 1% bovine serum albumin (BSA), 1.0 mM ethylene diamine tetraacetic acid (EDTA, pH 8) at 65° C., followed by washing 3× with 0.1% SDS and 0.1× SSC (0.1× SSC contains 0.015 M sodium chloride and 0.0015 M trisodium citrate, pH 7.0) at 65° C.

A number of homologs have been identified using the methods of this invention. For example, SEQ ID NO:3 is the gene sequence of a homolog A7 of the atzA gene that shows enhanced atrazine degradation activity and, surprisingly, also demonstrated enhanced TERBUTHYLAZINE degradation activity. TERBUTHYLAZINE degradation experiments are provided in Example 6. The amino acid sequence of the enzyme encoded by SEQ ID NO:3 identified as SEQ ID NO:5. SEQ ID NO:4 is the gene sequence of the homolog T7 of the alzA gene that shows enhanced atrazine degradation activity and enhanced TERBUTHYLAZINE degradation activity. A summary of the TERBUTHYLAZINE degradation activity for T7 and A7 is provided in Example 6. SEQ ID NO:6 provides the amino acid sequence of the homolog encoded by SEQ ID NO:4. FIG. 1 provides the nucleotide sequence alignment of wild type atzA from SEQ ID NO:1 with SEQ ID NO:3 and FIG.2 provides the nucleotide sequence alignrent of SEQ ID NO:1 with SEQ ID NO:4. FIG. 3 provides the amino acid sequence alignment of SEQ ID NO:2, the amino acid sequence of the protein encoded by SEQ ID NO:1, with SEQ ID NO:5 and FIG. 4 provides the amino acid sequence alignment of SEQ ID NO:2 with SEQ ID NO:6. A review of the sequences encoding A7 and T7 indicate that both homologs have a total of 8 amino acid changes relative to native AtzA (SEQ ID NO:2). Seven amino acid changes are common to both A7 and T7. The nucleic acid sequences of other homologs with altered activity include A40 (nucleic acid SEQ ID NO:17; amino acid sequence SEQ ID NO:22); A42 (nucleic acid SEQ ID NO:18; amino acid sequence SEQ ID NO:23); A44 (nucleic acid SEQ ID NO:19; amino acid sequence SEQ ID NO:24), A46 (nucleic acid SEQ ID NO:20; amino acid sequence SEQ ID NO:25); and A60 (nucleic acid SEQ ID NO:21; amino acid sequence SEQ ID NO:26).

Without intending to limit the scope of this invention, the success attributed to the identification of homologs of AtzA may be based on the recognition that this protein is not evolutionarily mature. Therefore, not all gene sequences are good candidates as the starting material for identifying a number of biological variants of a particular protein and similarly, not all enzymes are amenable to the order of magnitude of rate enhancement by directed evolution using DNA shuffling or other methods. Without intending to limit the scope of this invention, it is believed that some enzymes are already processing substrates at their theoretical rate limit. In these cases, catalysis is limited by the physical diffusion of the substrate onto the catalytic surface of the enzyme. Thus, changes in the enzyme would not likely improve the rate of catalysis. Examples of enzymes that operate at or near catalytic "perfection" are triosephosphate isomerase, fumarase, and crotonase (available from the GenBank database system). Even biodegradative enzymes that hydrolyze toxic substrates fall into this class. For example, the phosphotriesterase that hydrolyzes paraoxon operates near enough to the diffusion limit and suggests that it would not be a good candidate for mutagenic methods to improve the catalytic rate constant of the enzyme with its substrate (see Caldwell et al., *Biochem.* 30:7438–7444 (1991)).

The gene sequences of this invention can be incorporated into a variety of vectors. Preferably, the vector includes a region encoding a homolog of AtzA and the vector can also include other DNA segments operably linked to the coding sequence in an expression cassette, as required for expression of the homologs, such as a promoter region operably linked to the 5' end of the coding DNA sequence, a selectable marker gene, a reporter gene, and the like.

The present invention also provides recombinant cells expressing the homologs of this invention. For example, DNA that expresses the homologs of this invention can be expressed in a variety of bacterial strains including *E. coli* sp. strains and Pseudomononas sp. strains. Other organisms include, but are not limited to, Rhizobium, Bacilluis, Bradyrhizobium, Arthrobacter, Alcaligenes, and other rhizosphere and nonrhizosphere soil microbe strains.

In addition to prokaryotes, eukaryotic microbes such as filamentous fungi or yeast are suitable hosts for vectors encoding atzA or its homologs. *Saccharomyces cerevisiae*, or common baker's yeast, is the most commonly used among lower eukaryotic host microorganisms. However, a number of other genera, species, and strains are commonly available and useful herein, such as *Schizosaccaromyces pombe*, Kluyveromyces hosts such as, e.g., *K. lactis, K. fragilis, K. bulgaricus, K. thermotolerans*, and *K marxianus, Pichia pastoris*, Candida, *Trichoderma reesia*, Neurospora crassa, and filamentous fungi such as, e.g., Neurospora, Penicillium, Tolypocladium, and Aspergillus hosts such as *A. nidulans*.

Prokaryotic cells used to produce the homologs of this invention are cultured in suitable media, as described generally in Maniatis et al., *Molecular Cloning: A Laboratorv Manual*; Cold Spring Harbor Press: Cold Spring Harbor, N.Y. (1989). Any necessary supplements may also be included at appropriate concentrations that would be known to those skilled in the art. In general the *E. coli* expressing the homologs of this invention are readily cultured in LB media (see Maniatis, supra). The culture conditions, such as temperature, pH, and the like, are those previously used with the host cell selected for expression, and will be apparent to those skilled in the art. Induction of cells to express the AtzA protein is accomplished using the procedures required by the particular expression system selected. The host cells referred to in this disclosure are generally cultured in vitro. Cells are harvested, and cell extracts are prepared, using standard laboratory protocols.

This invention also relates to isolated proteins that are the product of the gene sequences of this invention. The isolated proteins are protein homologs of the wild-type atrazine chlorohydrolase enzyme despite their potential for altered substrate preference. The protein can be isolated in a variety of methods disclosed in the art and a preferred method for isolating the protein is provided in Examples 4 and 5 and in the publications of de Souza et al. (supra).

The wild-type AtzA protein acts on Atrazine, desethylatrazine, Desisopropylatrazine and SIMAZINE but did not degrade Desethyldesisopropylatrazine or MELAMINE and only poorly degraded TERBUTHYLAZINE. Homologs identified in this invention have a spectrum of substrate preferences identical to the wild-type AtzA protein and in addition, for example, are able to degrade other substrates such as TERBUTHYLAZINE. That homologs were identified that were capable of degrading two different s-triazine-containing compounds suggests that the methods of this invention can be used on the wild-type progenitor atzA gene or on the homologs produced by this invention to produce even more useful proteins for environmental remediation of s-triazine-containing compounds. Example 7 provides an assay for detecting degradation, including deamination, of a soluble s-triazine-containing compound.

Various environmental remediation techniques are known that utilize high levels of proteins. Bacteria or other hosts expressing the homologs of this invention can be added to a remediation mix or mixture in need of remediation to promote contaminate degradation. Alternatively, isolated AtzA homologs can be added. Proteins can be bound to immobilization supports, such as beads, particles, films, etc., made from latex, polymers, alginate, polyurethane, plastic, glass, polystyrene, and other natural and man-made support materials. Such immobilized protein can be used in packed-bed columns for treating water effluents. The protein can be used to remediate liquid samples, such as contaminated water, or solids. The advantage of some of the homologs identified thus far indicate that the homologs demonstrate an ability to degrade more than one substrate and to degrade the substrate at a faster rate or under different reaction conditions from the native enzyme.

All references and publications cited herein are expressly incorporated by reference into this disclosure. The invention will be further described by reference to the following detailed examples. Particular embodiments of this invention will be discussed in detail and reference has been made to possible variations within the scope of this invention. There area variety of alternative techniques and procedures available to those of skill in the art which would similarly permit one to successfully perform the intended invention that do not detract from the spirit and scope of this invention.

EXAMPLE 1

Isolation of Wild-type atzA Gene from Pseudomoonas sp. Strain ADP Bacterial Strains and Growth Conditions Pseudomnonas sp. strain ADP (Mandelbaum et al., *Appl. Environ. Microbiol.*, 59, 1695–1701 (1993)) was grown at 37° C. on modified minimal salt buffer medium, containing 0.5% (wt/vol) sodium citrate dihydrate. The atrazine stock solution was prepared as described in Mandelbaum et al., *Appl. Environ. Microbiol.*, 61, 1451–1457 (1995)). *Escherichia coli* DH5α was grown in Luria-Bertani (LB) or M63 minimal medium, which are described in Maniatis et al., *Molecular Cloning*: A Laboratory Manual; Cold Spring Harbor Press: Cold Spring Harbor, N.Y. (1989). Tetracycline (15 µg/ml), kanamycin (20 µg/ml), and chloramphenicol (30 µg/ml) were added as required.

To construct the Pseudomonas sp. strain ADP genomic library, total genomic DNA was partially digested with EcoRI, ligated to the EcoRI-digested cosmid vector pLAFR3 DNA, and packaged in vitro. The completed genomic DNA library contained 2000 colonies.

To identify the atrazine degrading clones, the entire gene library was replica-plated onto LB medium containing 500 µg/ml atrazine and 15 µg/ml tetracycline. Fourteen colonies having clearing zones were identified. All fourteen clones degraded atrazine, as determined by HPLC analysis. Cosmid DNA isolated from the fourteen colonies contained cloned DNA fragments which were approximately 22 kb in length. The fourteen clones could be subdivided into six groups on the basis of restriction enzyme digestion analysis using EcoRI. All fourteen clones, however, contained the same 8.7 kb EcoRI fragment. Thirteen of the colonies, in addition to degrading atrazine, also produced an opaque material that surrounded colonies growing on agar medium. Subsequent experiments indicated that the opaque material only was observed in *E. coli* clones which accumulated hydroxyatrazine. Thus, the cloudy material surrounding *E. coli* pMD2–pMD4 colonies was due to the deposition of hydroxyatrazine in the growth medium. The one colony that degraded atrazine without the deposition of the opaque material was selected for further analysis. The clone from this colony was designated pMD1.

EXAMPLE 2

Mutagenesis Procedure

Gene Shuffling. Atz A and B genes were subcloned from pMD1 into pUC 18. The two inserts were reduced in size to remove extraneous DNA. A 1.9 kb AvaI fragment containing atzA was end-filled and cloned into the end-filled AvaI site of pUC18. A 3.9 kb ClaI fragment containing atzB was end-filled and cloned into the HincII site of pUC18. The gene atzA was then excised from pUC18 with EcoRI and BamHI, AtzB with BamH and HindIII, and the two inserts were co-ligated into pUC18 digested with EcoRI and HindIII. The result was a 5.8 kb insert containing AtzA and AtzB in pUC18 (total plasmid size 8.4 kb).

Recursive sequence recombination was performed by modifications of existing procedures (Stemmer, W., *Proc. Natl. Acad. Sci. USA* 91:10747–10751 (1994) and Stemmer, W. *Nature* 370:389–391 (1994)). The entire 8.4 kb plasmid was treated with DNAase I in 50 mM Tris-Cl pH 7.5, 10 mM $MnCl_2$ and fragments between 500 and 2000 bp were gel purified. The fragments were assembled in a PCR reaction using Tth-XL enzyme and buffer from Perkin Elmer, 2.5 mM MgOAc, 400 µM dNTPs and serial dilutions of DNA fragments. The assembly reaction was performed in an MJ Research "DNA Engine" thermocycler programmed with the following cycles:

| 1 | 94° C., 20 seconds |
| 2 | 94° C., 15 seconds |
| 3 | 40° C., 30 seconds |
| 4 | 72° C., 30 seconds + 2 seconds per cycle |
| 5 | go to step 2 39 more times |
| 6 | 4° C. |

The atzA gene could not be amplified from the assembly reaction using the polymerse chain reaction, so instead DNA from the reaction was purified by standard phenol extraction and ethanol precipitation methods and digested with KpnI to linearize the plasmid (the KpnI site in pUC18 was lost during sulbcloning, leaving only the KpnI site in atzA). Linearized plasmid was gel-purified, self-logated overnight and transformed into E Coli strain NM522.

Serial dilutions of the transformation reaction were plated onto LB plates containing 50 μg/ml ampicillin. the remainder of the transformation was stored in 25% gllycerol and frozen at −80° C. Once the transformed cells were titered, the frozen cells were plated at a density of between 200 and 500 on 150 mm diameter plates containing 500 μg/ml atrazine or another substrate and growm at 37° C.

Atrazine att 500 μg/ml forms an insoluble precipitate creating a cloudy apperance on the agar plate. The solubility of atrazine is about 30 μg/ml, therefore for preecipitable substrate assays, such as the assay disclosed here, the atrazine concentration should be preferably greater than 30 μg/ml. Atrzine or hydroxyatrazine were incorporated in solid LB or minimal medium, as described in Mandelbaum et al., $Appl.$ $Environ.$ $Microbiol.$, 61, 1451–1457 (1995), at a final concentration of 500 μg/ml to produce an opaque suspension of small particles in the clear agar. AtzA and the homologs with atrazine-degrading activity convert atrazine into a soluble product. The degradation of atrazine or hydroxyatrazine by wild-type and recombinant bacteria was indicated by a zone of clearing surroundings colonies. The more active the homolog, the more rapidly a clear halor formed on atrazine-containing plates. Positive colonies that most rapidly formed the largest clear zones were selected initially for further analysis. The approximately) 40 best colonies were picked, pooled, grown in the presence of 50 μg/ml ampicillin and plasmid prepared from them. More efficient enzymes can also be tested using atrazine concentrations greater than 500 μg/ml.

The entire process (from DNAase-treatment to plating on atrazine plates) was repeated 4 times as a method for further improving on the rate of enzymatic activity. In several experiments, cells were plated on plates containing 500 μg/ml atrazine and on plates containing 500 μg/ml of the atrazine analogue TERBUTHYLAZINE.

Other compounds can be tested in similar assays replacing atrazine (2-chloro-4-ethlyamino-6-isopropylamino- 1,3,5-s-triazine) for the following compounds: desethylatrazine (2-chloro-4-amino-6-isopropylamino-s-triazilne), deisopropylatrazine (2-chloro-4-ethylamino-6-amino-s-triazine), hydroxyatrazine (2-hydroxy-4-ethylamino-6-isopropylamino-s-triazine), desethylhydroxyatrazine (2-hydroxy-4-amino-6-isopropylamino-s-triazine). desisopropylhydroxyatrazine (2-hydroxy-4-amino-6-isopropylamino-s-triazine), desethyldesisopropylatrazine (2-chloro-4,6-diamino-s-triazine), SIMAZINE (2-chloro-4, 6-diethylamino-s-triazine), TERBUTHYLAZINE (2-chloro-4-ethylamino-6-terbutylamino-s-triazine, and MELAMINE (2,4,6-triamino-s-triazine) were obtained from Ciba Geigy Corp., Greensboro, N.C. Ammelide (2,4-dihydroxy-6-amino-s-triazine), ammeline (2-hydroxy-4,6,-diamino-s-triazine) were obtained from Aldrich Chemical Co., Milwaukee, Wis.

EXAMPLE 3

DNA Sequencing of Wild-Type AtzA and Homolog AtzA Genes

DNA Sequencing. The nucleotide sequence of the approximately 1.9-kb AvaI DNA fragment in vector pACYC184, designated pMD4, or the homologs in pUC 18 or another vector was determined using both DNA strands. DNA was sequenced by using a PRISM Ready Reaction DyeDeoxy Terminator Cycle Sequencing kit (Perkin-Elmer Corp., Norwalk, Conn.) and a ABI Model 373A DNA Sequencer (Applied Biosystems, Foster City, Calif.). Nucleotide sequence was determined initially by subcloning and subsequently by using primers designed based on sequence information obtained from subcloned DNA fragments. The GCG sequence analysis software package (Genetics Computer Group, Inc., Madison, Wis.) was used for all DNA and protein sequence comparisons. Radiolabelled chemicals were obtained from Ciba Geigy Corp., Greensboro, N.C.

EXAMPLE 4

Protein Purification of AtzA or Homologs $E.$ $coli$ transformed with a vector containing the wild type atzA gene or alternatively with a homolog, in a vector capable of directing expression of the gene as a protein, was grown overnight at 37° C. in eight liters of LB medium containing 25 μg/ml chloramphenicol. The culture medium was centrifuged at 10,000×g for 10 minutes at 4° C., washed in 0.85% NaCl, and the cell pellet was resuspended in 50 ml of 25 mM MOPS buffer (3[-N-morpholino]propane-sulfonic acid, pH 6.9), containing phenylmethylsulfonylfluoride (100 μg/ml). The cells were broken by three passages through an Amicon French Pressure Cell at 20,000 pounds per square inch (psi) at 4° C. Cell-free extract was obtained by centrifugation at 10,000×g for 15 minutes. The supernatant was clarified by centrifuigation at 18,000×g for 60 minutes and solid $NH_4SO_4$ was added, with stirring, to a final concentration of 20% (wt/vol) at 4° C. The solution was stirred for 30 minutes at 4° C. and centrifuged at 12,000×g for 20 minutes. The precipitated material was resuspended in 50 ml of 25 mM MOPS buffer (pH 6.9), and dialyzed overnight at 4° C. against 1 liter of 25 mM MOPS buffer (pH 6.9).

Where purified protein was desired, the solution was loaded onto a Mono Q HR 16/10 Column (Pharmacia LKB Biotechnology, Uppsala, Sweden). The column was washed with 25 mM MOPS buffer (pH 6.9), and the protein was eluted with a 0–0.5 M KCl gradient. Protein eluting from the column was monitored at 280 nm by using a Pharmacia U.V. protein detector. Pooled fractions containing the major peak were dialyzed overnight against 1 liter 25 mM MOPS buffer (pH 6.9). The dialyzed material was assayed for atrazine degradation ability by using HPLC analysis (see above) and analyzed for purity by sodium dodecyl sulfate (SDS) polyacrylamide gel electrophoreses (Laemlli).

Protein Verification: Protein subunit sizes were determined by SDS polyacrylamide gel electrophoresis by comparison to known standard proteins, using a Mini-Protean II gel apparatus (Biorad, Hercules, Calif.). The size of the holoenzyme was determined by gel filtration chromatography on a Superose 6 HR (1.0×30.0 cm) column, using an FPLC System (Pharmacia, Uppsala, Sweden). The protein was eluted with 25 mM MOPS buffer (pH 6.9) containing 0.1 M NaCl. Proteins with known molecular weights were used as chromatography standards. Isoelectric point determinations were done using a Pharmacia Phast-Gel System and Pharmacia IEF 3-9 media. A Pharmacia broad-range pI calibration kit was used for standards.

Enzyme Kinetics. Purified AtzA protein and homologs of the protein at 50 $\mu$g/ml, were separately added to 500 $\mu$l of different concentrations of atrazine (23.3 $\mu$M, 43.0 $\mu$M, 93 $\mu$M, 233 $\mu$M, and 435 $\mu$M in 25 mM MOPS buffer, pH 6.9) or another s-triazine-containing compound and reactions were allowed to proceed at room temperature for 2, 5, 7, and 10 minutes. The reactions were stopped by boiling the reaction tubes at specific times, the addition of 500 $\mu$l acetonitrile and rapid freezing at $-80°$ C. Thawed samples were centrifuged at 14,000 rpm for 10 minutes, the supernatants were filtered through a 0.2 $\mu$M filter, and placed into crimp-seal HPLC vials. HPLC analysis was done as described above. Based on HPLC data, initial rates of atrazine degradation and hydroxyatrazine formation were calculated and Michaelis Menton and Lineweaver Burke plots were constructed.

Effect of simple nitrogen sources on atrazine degradation. From experiments done with Pseudomonas species strain ADP on solid media with 500 ppm atrazine and varying concentrations of ammonium chloride, ammonium chloride concentrations as low as 0.6–1.2 mM were sufficient to inhibit visible clearing on the plates, even after 2 weeks of incubation either at 28° C. or 37° C. With similar experiments using E. coli DH5α (pMD1 or pMD2) and other E. coli strains, atrazine degradation was observed in the presence of ammonium chloride concentrations as high as 48 mM. This value is almost 40–80 fold higher than the wild-type tolerance for ammonium chloride with concomitant atrazine degradation. Therefore, it was not necessary to use media free of exogenous ammonia in the screening assays.

EXAMPLE 5

Further Characterization of the Enzymatic Activity of the Homologs

Analysis of atrazine metabolism by E. coli clones. The extent and rate of atrazine degradation was determined in liquid culture. E. coli clones containing plasmids capable of expressing the lhomologs were compared to Pseudomonas sp. strain ADP for their ability to transform ring-labelled [$^{14}$C]-atrazine to water-soluble metabolites. This method, which measures [$^{14}$C]-label partitioning between organic and aqueous phases, had previously been used with Pseudomonas sp. ADP to show the transformation of atrazine to metabolites that partition into the aqueous phase, in Mandelbaum et al., *Appl. Environ. Microbiol.*, 61, 1451–1457 (1995). When Pseudomonas sp. strain ADP or E. coli capable of expressing the homologs of this invention were incubated for 2 hours with [$^{14}$C]-atrazine, 98%, 97%, 88%, and 92%, respectively, of the total recoverable radioactivity was found in the aqueous phase. Greater than 90% of the initial radioactivity was accounted for as atrazine plus water soluble metabolites, indicating that little or no $^{14}CO_2$ was formed. In contrast, forty-four percent of the radioactivity was lost from the Pseudomonas ADP culture after 18.5 hours. In previous studies done with Pseudomonas sp. strain ADP and ring-labelled $^{14}$C-atrazine, radiolabel was lost from culture filtrates as $^{14}CO_2$ (see, e.g., Mandelbaum et al., *Appl. Environ. Microbiol.*, 61, 1451–1457 (1995)). Retention of the radiolabel is indicative of lack or inhibition of enzymatic activity. While these studies were performed for AtzA, similar studies are used to assess the activity of the homologs of this invention.

EXAMPLE 6

Assays to Detect Homologs of AtzA on TERBUTHYLAZINE

TERBUTHYLAZINE was incorporated in solid LB medium at a final concentration of about 400–500 $\mu$g/ml to produce an opaque suspension of sample particles in the clear agar. The degradation of terbuthyalazine by recombinant bacteria was indicated by a zone of clearing surrounding the colonies. HPLC analysis was performed with a Hewlett Packard HP 1090 Liquid Chromatograph system equipped with a photodiode array detector and interfaced to an HP 79994A Chemstation. TERBUTHYLAZINE and its metabolites were resolved by using an analytical $C^{18}$ reverse-phase Nova-Pak HPLC column (4-$\mu$m-diameter spherical packing, 150 by 3.9 mm; Waters Chromatography, Milford, Mass.) and an acetonitrile (ACN) gradient, in water, at a flow rate of 1.0 ml $min^{-1}$. Linear gradients of 0 to 6 min, 10 to 25% ACN; 6 to 21 min, 25 to 65% ACN; 21 to 23 min, 65 to 100% ACN; and 23 to 25 min, 100% ACN were used. Spectral data of the column eluent were acquired between 200 and 400 nm (12-nm bandwidth per channel) at a sampling frequency of 640 ms. Spectra were referenced against a signal of 500 nm.

Figure 7B:
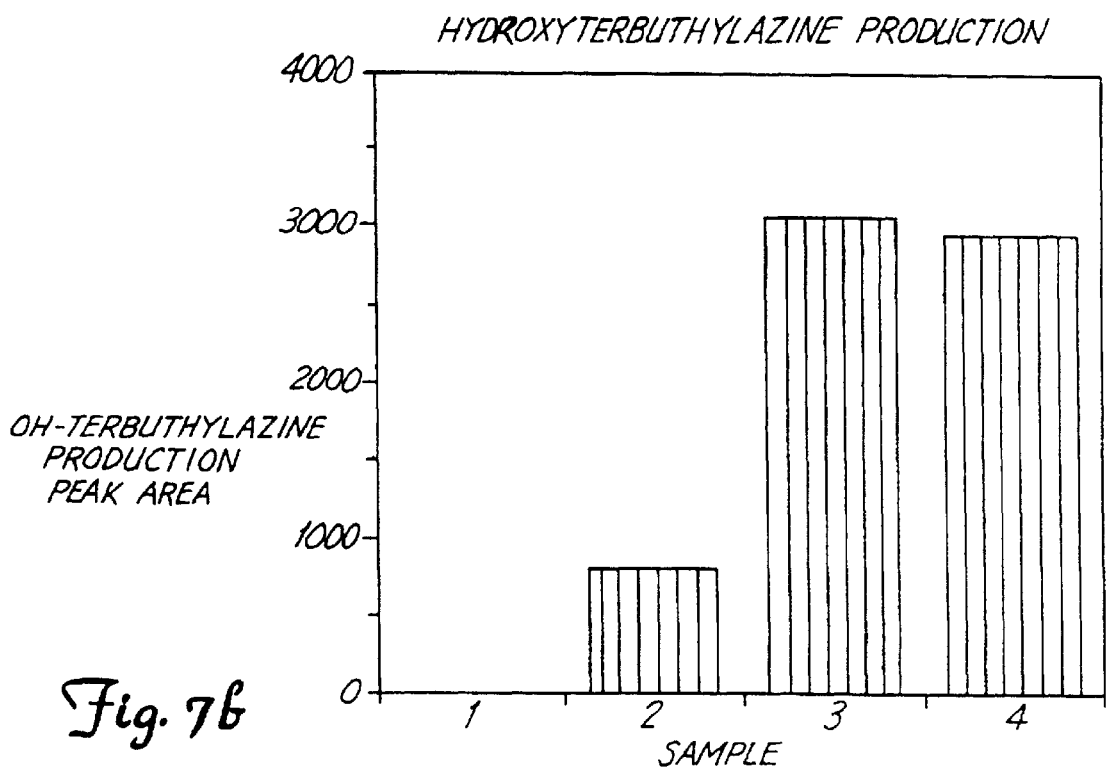
FIG. 7(b) illustrates the relative amount of hydroxyterbuthylazine as a measure of TERBUTHYLAZINE degradation.
Figure 8A:
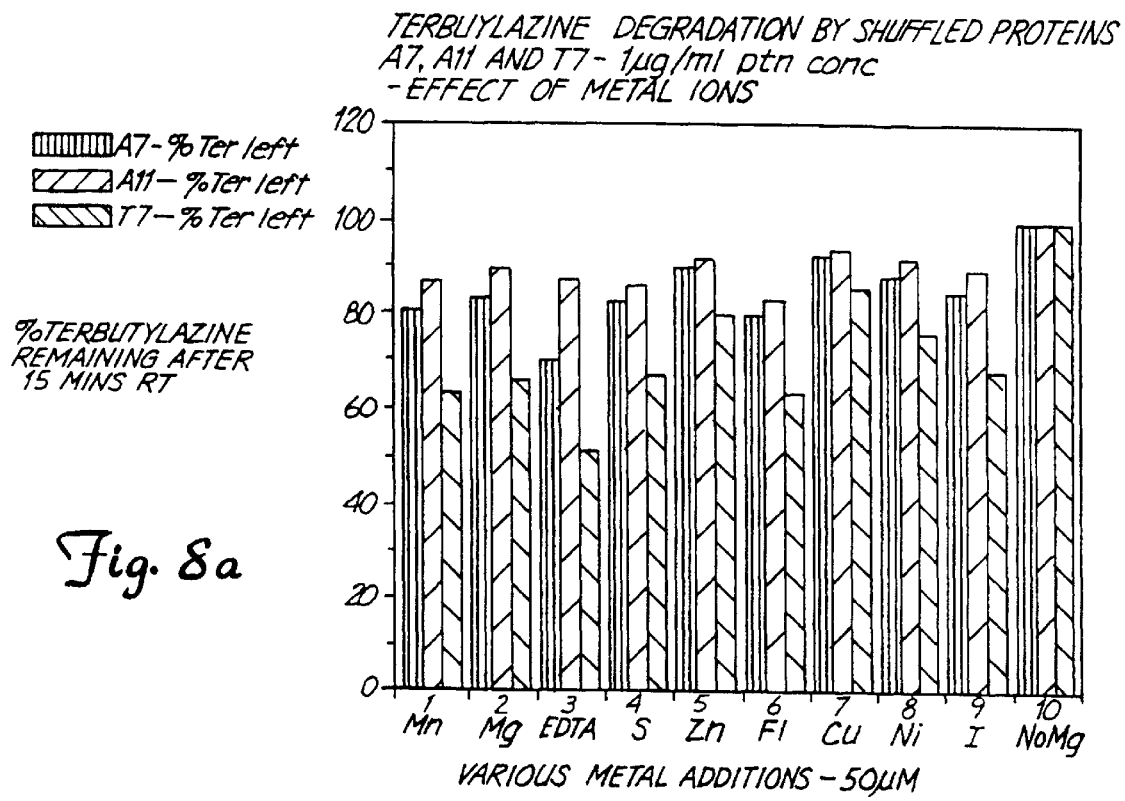
FIGS. 8A and B. is another set of histograms illustrating the terbutylazine degradative ability of three homologs A7, A11, and T7.
Figure 8B:
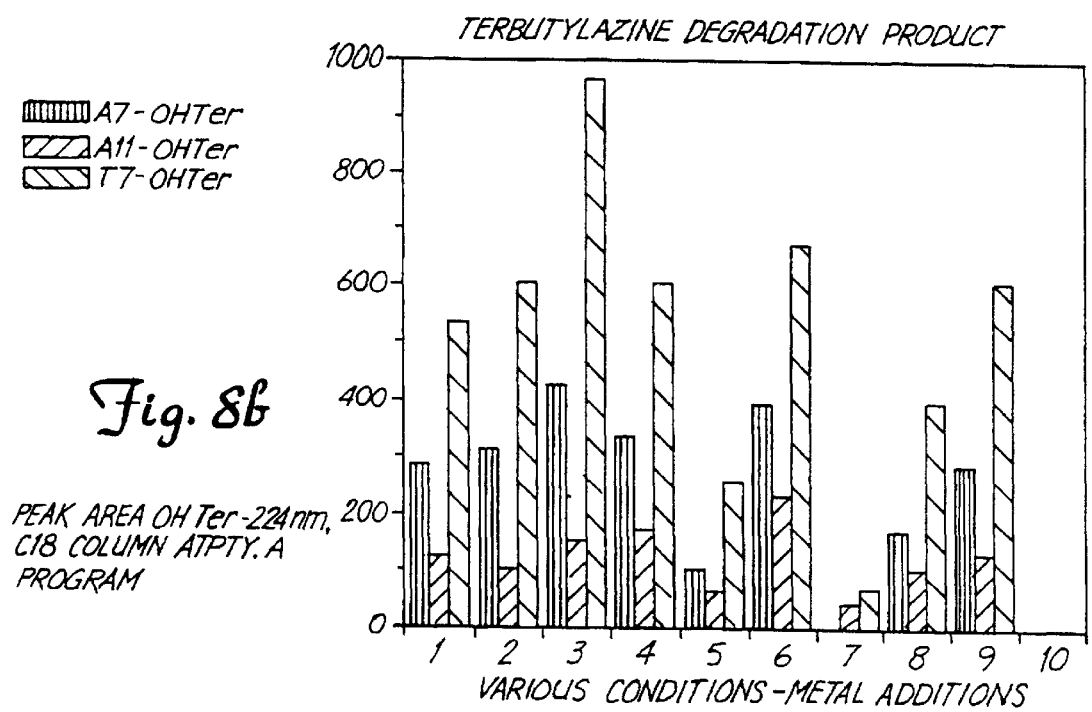
FIG. 8(b) provides the relative amount of hydroxterbuthylazine in the presence or absence of the metals and compounds of Samples 1–10.

Comparative results of an assay to assess TERBUTHYLAZINE degradation is provided in FIGS. 7 and 8. FIG. 7(a) provides a histogram demonstrating the relative percentage of TERBUTHYLAZINE remaining in samples tested while FIG. 7(b) provides a measure of the production of hydroxyterbuthylazine as a measure of TERBUTHYLAZINE degradation. Sample 1 is a control sample without enzyme. Sample 2 uses a two fold excess of AtzA protein as compared to the concentration of homolog added in Sample 3 and Sample 4. Sample 3 employed the T7 homolog (SEQ ID NO:6) and Sample 4 employed the A7 homolog (SEQ ID NO:5). Results were determined by HPLC as described above. FIG. 8(a) provides the percentage of TERBUTHYLAZINE remaining after a 15 minute exposure to homologs A7, Al 1, and T7. Samples 1–10 refer to the effect of homolog activity in the presence of 50 uM of: Manganese (1); Mangnesium (2), EDTA (3); cobalt (4); zinc (5); iron (6); copper (7); nickel (8); no metal (9); or no eznyme (I10). FIG. 8(b) provides the relative amount of hydroxyterbuthylazine as a measure of TERBUTHYLAZINE degradation for homologs A7 (solid bar), A11 (hatched bar), or T7 (open bar) in the presence or absence of additives 1–10 (supra).

EXAMPLE 7

Assays to Detect Homologs of AtzA on "MELAMINE"

"MELAMINE" (2, 4, 6-triamino-s-triazine) at a concentration of at least about 1 mM to about 5 mM and preferably about 2 mM MELAMINE is incorporated into solid minimal nutrient media as the sole nitrogen source. Bacteria are distributed on the plate and growth of the organisms is indicative of their ability to degrade MELAMINE, thereby releasing ammonia for growth. Growth is evidence of the ability of the organisms expressing the homologs of this invention to deaminate MELAMINE. There is more than one nitrogen-containing group in MELAMINE. Therefore the selection of larger colonies on MELAMINE containing solid minimal nutrient media could be used to select for faster MELAMINE-degrading homologs.

A comparison of the nucleic acid sequence from a wild type MELAMINE degrading Pseudomonas NRRLB 12227 strain as compared to the atzA gene sequence indicated a homology of more than 90% over a 500 base pair sequence obtained from NRRLB using primer selected that were internal to atzA suggesting that homologs of atzA could be identified that degrade "MELAMINE." This strain did not degrade atrazine. Moreover, homologs identified using the methods of Example 2 are subjected to further mutagenesis and colonies capable of growing in MELAMINE can be identified. Colonies containing the protein AtzA are tested for growth in MELAMINE under identical conditions. Other s-triazine containing compounds such as the pesticides available under the tradenames "AMETRYN", "PROMETRYN", "PROMETRON", "ATRATON" and "CYROMAZINE" could also function as substrates for other homologs of this invention.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A DNA fragment encoding a homolog of atrazine chlorohydrolase and comprising the sequence selected from the group consisting of SEQ ID NO:3, SEQ ID NO:4, and SEQ ID NOS:17–21.

2. An expression vector comprising the DNA fragment of claim 1.

3. A cell comprising the expression vector of claim 2.

4. The cell of claim 3 wherein the cell is a bacterium.

5. The bacterium of claim 4 wherein the bacterium is *E. coli*.

6. A DNA fragment encoding a homolog of atrazine chlorohydrolase wherein said DNA fragment has at least 95% homology to SEQ ID NO: 1 and wherein said DNA comprises a sequence selected from the group consisting of SEQ ID NOs: 7–11.

7. An expression vector comprising the DNA fragment of claim 6.

8. A cell comprising the expression vector of claim 7.

9. The cell of claim 8 wherein the cell is a bacterium.

10. The bacterium of claim 9 wherein the bacterium is *E. coli*.

* * * * *

UNITED STATES PATENT AND TRADEMARK OFFICE
CERTIFICATE OF CORRECTION

PATENT NO.     : 6,265,201 B1
DATED          : July 24, 2001
INVENTOR(S)    : Lawrence P. Wackett et al.

It is certified that error appears in the above-identified patent and that said Letters Patent is hereby corrected as shown below:

Title page,
Item [56], OTHER PUBLICATIONS,
Please delete "Hydoly-" and insert -- Hydroly -- therefor.
Please delete "*Agic.*" and insert -- *Agric.* -- therefor
Please delete "indentifying" and insert -- identifying -- therefor.
Please delete "Bacteriol" and insert -- Bacterial -- therefor.
Please delete *"Bacterial."* and insert -- *Bacteriol.* -- therefor.
Please delete "Active Fractions for" and insert -- Active Fractions from -- therefor.
Please delete "Effects" and insert -- Effect -- therefor.
Please delete "Indentification" and insert -- Identification -- therefor.

Column 3,
Line 53, please delete "hlaving" and insert -- having -- therefor.

Column 5,
Line 20, after "(SEQ ID NO:1 and SEQ ID NO:3).", please insert -- The boxed sequences indicate areas of nonidentity between the two nucleotide sequences. --;
Line 23, after "(SEQ ID NO:1 and SEQ ID NO:4).", please insert -- The boxed sequences indicate areas of nonidentity between the two nucleotide sequences.--;
Line 26, after "(SEQ ID NO:2 and SEQ ID NO:5).", please insert -- The boxed sequences indicate areas of nonidentity between the two amino acid sequences. Start, indicates beginning of the protein; Stop, indicates end of the protein. --;
Line 29, after "(SEQ ID NO:2 and SEQ ID NO:6)", please insert -- The boxed sequences indicate areas of nonidentity between the two amino acid sequences. Start, indicates beginning of the protein; Stop, indicates end of the protein. --;
Line 31, please delete "Pseudonionas" and insert -- Pseudomonas -- therefor.
Line 39, after "of clone A11", insert -- The boxed sequences indicate areas of nonidentity between the two nucleotide sequences. --;
Line 40, after "that are being verified.", please insert -- The four "C" nucleotides depicted above the top sequence in 5(a) and the eleven "G" nucleotides depicted above the top sequence in 5(b) indicate the correct nucleotide sequence of the top sequence. --;

Column 8,
Line 1, please delete "atra" and insert -- atzA -- therefor.
Line 36, please delete "alzA" and insert -- atzA -- therefor.

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Column 9,
Line 35, please delete "oi-" and insert -- or -- therefor.
Line 48, please delete "enzyme." and insert -- enzyme, -- therefor.
Line 53, please delete "Ikown" and insert -- known -- therefor.

Column 11,
Line 49, please delete "TERBUTHYLAZFNE" and insert -- TERBUTHYLAZINE -- therefor.

Column 15,
Line 64, please delete "Pseudomoonas" and insert -- Pseudomonas -- therefor.
Line 66, please delete "Pseudomnonas" and insert -- Pseudomonas -- therefor.

Column 17,
Line 19, please delete "ampicillin." and insert -- ampicillin, -- therefor.
Line 24, please delete "growm" and insert -- grown -- therefor.
Line 25, please delete "att" and insert -- at -- therefor.

Column 18,
Line 8, please delete "AtzA" and insert -- atzA -- therefor.

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings,
Please delete Fig. 1A and insert the following therefor:

```
                                1/16
  1 .............................................GCGA   4
                                                 ||||
  1 CTCGGGTAACTTCTTGAGCGCGGCCACAGCAGCCTTGATCATGAAGGCGA  50

5 GCATGGTGACCTTGACGCCGCTCTTTTCGTTCTCTTTGTTGAACTGCACG  54
    |||||||||||||||||||||||||||||||||||||||||||||||||
 51 GCATGGTGACCTTGACGCCGCTCTTTTCGTTCTCTTTGTTGAACTGCACG 100

55 CGAAAGGCTTCCAGGTCGGTGATGTCCGCGTCGTCGTGGTTGGTGACGTG 104
    |||||||||||||||||||||||||||||||||||||||||||||||||
101 CGAAAGGCTTCCAGGTCGGTGATGTCCGCGTCGTCGTGGTTGGTGACGTG 150

105 CGGGATGACCACCCAGTTGCGGTGCAGGTTTTTCGATGGCATAATATCTG 154
    |||||||||||||||||||||||||||||||||||||||||||||||||
151 CGGGATGACCACCCAGTTGCGGTGCAGGTTTTTCGATGGCATAATATCTG 200

155 CGTTGCGACGTGTAACACACTATTGGAGACATATCATGCAAACGCTCAGC 204
    |||||||||||||||||||||||||||||||||||||||||||||||||
201 CGTTGCGACGTGTAACACACTATTGGAGACATATCATGCAAACGCTCAGC 250

205 ATCCAGCACGGTACCCTCGTCACGATGGATCAGTACCGCAGAGTCCTTGG 254
    |||||||||||||||||||||||||||||||||||||||||||||||||
251 ATCCAGCACGGTACCCTCGTCACGATGGATCAGTACCGCAGAGTCCTTGG 300

255 GGATAGCTGGGTTCACGTGCAGGATGGACGGATCGTCGCGCTCGGAGTGC 304
    |||||||||||||||||||||||||||||||||||||||||||||||||
301 GGATAGCTGGGTTCACGTGCAGGATGGACGGATCGTCGCGCTCGGAGTGC 350

305 ACGCCGAGTCGGTGCCTCCGCCAGCGGATCGGGTGATCGATGCACGCGGC 354
    |||||||||||||||||||||||||||||||||||||||||||||||||
351 ACGCCGAGTCGGTGCCTCCGCCAGCGGATCGGGTGATCGATGCACGCGGC 400

355 AAGGTCGTGTTACCCGGTTTCATCAATGCCCACACCCATGTGAACCAGAT 404
    |||||||||||||||||||||||||||||||||||||||||||||||||
401 AAGGTCGTGTTACCCGGTTTCATCAATGCCCACACCCATGTGAACCAGAT 450

405 CCTCCTGCGCGGAGGGCCCTCGCACGG CGTCAATTCTATGACTGGCTGT 454
    |||||||||||||||||||||||||||| ||||||||||||||||||||
451 CCTCCTGCGCGGAGGGCCCTCGCACGG A CGTCAATTCTATGACTGGCTGT 500

455 TCAACGTTGTGTATCCGGGACAAAAGGCGATGAGACCGGAGGACGTAGCG 504
    |||||||||||||||||||||||||||||||||||||||||||||||||
501 TCAACGTTGTGTATCCGGGACAAAAGGCGATGAGACCGGAGGACGTAGCG 550

505 GTGGCGGTGAGGTTGTATTGTGCGGAAGCTGTGCGCAGCGGGATTACGAC 554
    |||||||||||||||||||||||||||||||||||||||||||||||||
551 GTGGCGGTGAGGTTGTATTGTGCGGAAGCTGTGCGCAGCGGGATTACGAC 600

555 GATCAACGAAAACGCCGATTCGGCCATCTACCCAGGCAACATCGAGGCCG 604
    |||||||||||||||||||||||||||||||||||||||||||||||||
601 GATCAACGAAAACGCCGATTCGGCCATCTACCCAGGCAACATCGAGGCCG 650
```

*Fig. 1A*

UNITED STATES PATENT AND TRADEMARK OFFICE
CERTIFICATE OF CORRECTION

PATENT NO. : 6,265,201 B1  
DATED : July 24, 2001  
INVENTOR(S) : Lawrence P. Wackett et al.

Page 4 of 13

It is certified that error appears in the above-identified patent and that said Letters Patent is hereby corrected as shown below:

Drawings (cont'd),
Please delete Fig. 1B and insert the following therefor:

2/16

```
605 CGATGGCGGTCTATGGTGAGGTGGGTGTGAGGGTCGTCTACGCCCGCATG 654
    ||||||||||||||||||||||||||||||||||||||||||||||||||
651 CGATGGCGGTCTATGGTGAGGTGGGTGTGAGGGTCGTCTACGCCCGCATG 700

655 TTCTTTGATCGGATGGACGGGCGCATTCAAGGGTATGTGGACGCCTTGAA 704
    ||||||||||||||||||||||||||||||||||||||||||||||||||
701 TTCTTTGATCGGATGGACGGGCGCATTCAAGGGTATGTGGACGCCTTGAA 750

705 GGCTCGCTCTCCCCAAGTCGAACTGTGCTCGATCATGGAGGAACGGCTG 754
    |||||||||||||||||||||||||||||||||||||||||||||||||
751 GGCTCGCTCTCCCCAAGTCGAACTGTGCTCGATCATGGAGGAACGGCTG 800

755 TGGCCAAAGATCGGATCACAGCCCTGTCAGATCAGTATCATGGCACGGCA 804
    ||||||||||||||||||||||||||||||||||||||||||||||||||
801 TGGCCAAAGATCGGATCACAGCCCTGTCAGATCAGTATCATGGCACGGCA 850

805 GGAGGTCGTATATCAGTTTGGCCCGCTCCTGCCACTACCACGGCGGTGAC 854
    ||||||||||||||||||||||||||||||||||||||||||||||||||
851 GGAGGTCGTATATCAGTTTGGCCCGCTCCTGCCACTACCACGGCGGTGAC 900

855 AGTTGAAGGAATGCGATGGGCACAAGCCTTCGCCCGTGATCGGGCGGTAA 904
    ||||||||||||||||||||||||||||||||||||||||||||||||||
901 AGTTGAAGGAATGCGATGGGCACAAGCCTTCGCCCGTGATCGGGCGGTAA 950

905 TGTGGACGCTTCACATGGCGGAGAGCGATCATGATGAGCGGATTCATGGG 954
    ||||||||||||||||||||||||||||||||||||||||||||||||||
951 TGTGGACGCTTCACATGGCGGAGAGCGATCATGATGAGCGGATTCATGGG 1000

955 ATGAGTCCCGCCGAGTACATGGAGTGTTACGGACTCTTGGATGAGCGTCT 1004
     ||||||||||||||||||||||||||||||||||||||||||||||||||
1001 ATGAGTCCCGCCGAGTACATGGAGTGTTACGGACTCTTGGATGAGCGTCT 1050

1005 GCAGGTCGCGCATTGCGTGTACTTTGACCGGAAGGATGTTCGGCTGCTGC 1054
     ||||||||||||||||||||||||||||||||||||||||||||||||||
1051 GCAGGTCGCGCATTGCGTGTACTTTGACCGGAAGGATGTTCGGCTGCTGC 1100

1055 ACCGCCACAATGTGAAGGTCGCGTCGCAGGTTGTGAGCAATGCCTACCTC 1104
     ||||||||||||||||||||||||||||||||||||||||||||||||||
1101 ACCGCCACAATGTGAAGGTCGCGTCGCAGGTTGTGAGCAATGCCTACCTC 1150

1105 GGCTCAGGGGTGGCCCCCGTGCCAGAGATGGTGGAGCGCGGCATGGCCGT 1154
     ||||||||||||||||||||||||||||||||||||||||||||||||||
1151 GGCTCAGGGGTGGCCCCCGTGCCAGAGATGGTGGAGCGCGGCATGGCCGT 1200

1155 GGGCATTGGAACAGATAACGGGAATAGTAATGACTCCGTAACATGATCG 1204
     |||||||||||||||||||||||||||||||||||||||||||||||||
1201 GGGCATTGGAACAGATAACGGGAATAGTAATGACTCCGCAACATGATCG 1250

1205 GAGACATGAAGTTTATGGCCCATATTCACCGCGCGGTGCATCGGGATGCG 1254
     ||||||||||||||||||||||||||||||||||||||||||||||||||
1251 GAGACATGAAGTTTATGGCCCATATTCACCGCGCGGTGCATCGGGATGCG 1300
```

Fig 1B

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 1C and insert the following therefor:

*3/16*

```
1255 GACGTGCTGACCCCAGAGAAGATTCTTGAAATGGCGACGATCGATGGGGC 1304
     ||||||||||||||||||||||||||||||||||||||||||||||||||
1301 GACGTGCTGACCCCAGAGAAGATTCTTGAAATGGCGACGATCGATGGGGC 1350

1305 GCGTTCGTTGGGAATGGACCACGAGATTGGTTCCATCGAAACCGGCAAGC 1354
     ||||||||||||||||||||||||||||||||||||||||||||||||||
1351 GCGTTCGTTGGGAATGGACCACGAGATTGGTTCCATCGAAACCGGCAAGC 1400

1355 GCGCGGACCTTATCCTGCTTGACCTGCGTCAC CTCAGACGACTC TCAC 1404
     ||||||||||||||||||||||||||||||||| |||||||||||||
1401 GCGCGGACCTTATCCTGCTTGACCTGCGTCA CCTCAGACGACTC  TCA 1447

1405 CATCATTTGGCGGCCACGATCGTGTTTCAGGCTTACGGCAATGAGGTGGA 1454
     ||||||||||||||||||||||||||||||||||||||||||||||||||
1448 CATCATTTGGCGGCCACGATCGTGTTTCAGGCTTACGGCAATGAGGTGGA 1497

1455 CACTGTCCTGATTGACGGAAACGTTGTGATGGAGAACCGCCGCTTGAGCT 1504
     ||||||||||||||||||||||||||||||||||||||||||||||||||
1498 CACTGTCCTGATTGACGGAAACGTTGTGATGGAGAACCGCCGCTTGAGCT 1547

1505 TTCTTCCCCCTGAACGTGAGTTGGCGTTCCTTGAGGAAGCGCAGAGCCGC 1554
     ||||||||||||||||||||||||||||||||||||||||||||||||||
1548 TTCTTCCCCCTGAACGTGAGTTGGCGTTCCTTGAGGAAGCGCAGAGCCGC 1597

1555 GCCACAGCTATTTTGCAGCGGGCGAACATGGTGGCTAACCCAGCTTGGCG 1604
     ||||||||||||||||||||||||||||||||||||||||||||||||||
1598 GCCACAGCTATTTTGCAGCGGGCGAACATGGTGGCTAACCCAGCTTGGCG 1647

1605 CAGCCTCTAGGAAATGACGCCGTTGCTGCATCCGCCGCCCCTTGAGGAAA 1654
     ||||||||||||||||||||||||||||||||||||||||||||||||||
1648 CAGCCTCTAGGAAATGACGCCGTTGCTGCATCCGCCGCCCCTTGAGGAAA 1697

1655 TCGCTGCCATCTTGGCGCGGCTCGGATTGGGGGGCGGACATGACCTTGAT 1704
     ||||||||||||||||||||||||||||||||||||||||||||||||||
1698 TCGCTGCCATCTTGGCGCGGCTCGGATTGGGGGGCGGACATGACCTTGAT 1747

1705 GGATACAGAATTGCCATGAATGCGGCACTTCCGTCCTTCGCTCGTGTGGA 1754
     ||||||||||||||||||||||||||||||||||||||||||||||||||
1748 GGATACAGAATTGCCATGAATGCGGCACTTCCGTCCTTCGCTCGTGTGGA 1797

1755 ATCGTTGGTAGGTGAGGGTCGACTGCGGGCGCCAGCTTCCCGAAGA GTG 1804
     |||||||||||||||||||||||||||||||||||||||||||||| |||
1798 ATCGTTGGTAGGTGAGGGTCGACTGCGGGCGCCAGCTTCCCGAAGA GTG 1847

1805 AAAG....... 1808
     ||||
1848 AAAGGCCCGAG 1858
```

*Fig. 1C*

Page 5 of 13

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 2A and insert the following therefor:

4/16

```
  1 ...............GAGCGCGCCACAGCAGCCTTGATCATGAAGGCGA  35
                   ||||||||||||||||||||||||||||||||||
  1 CTCGGGTAACTTCTTGAGCGCGCCACAGCAGCCTTGATCATGAAGGCGA  50

36 GCATGGTGACCTTGACGCCGCTCTTTTCGTTCTCTTTGTTGAACTGCACG  85
    |||||||||||||||||||||||||||||||||||||||||||||||||
 51 GCATGGTGACCTTGACGCCGCTCTTTTCGTTCTCTTTGTTGAACTGCACG 100

86 CGAAAGGCTTCCAGGTCGGTGATGTCCGCGTCGTCGTGGTTGGTGACGTG 135
    |||||||||||||||||||||||||||||||||||||||||||||||||
101 CGAAAGGCTTCCAGGTCGGTGATGTCCGCGTCGTCGTGGTTGGTGACGTG 150

136 CGGGATGACCACCCAGTTGCGGTGCAGGTTTTTCGATGCCTAATATCTG  185
    ||||||||||||||||||||||||||||||||||||||||| |||||||
151 CGGGATGACCACCCAGTTGCGGTGCAGGTTTTTCGATGGCATAATATCTG 200

186 CGTTGCGACGTGTAACACACTATTGGAGACATATCATGCAAACGCTCAGC 235
    |||||||||||||||||||||||||||||||||||||||||||||||||
201 CGTTGCGACGTGTAACACACTATTGGAGACATATCATGCAAACGCTCAGC 250

236 ATCCAGCACGGTACCCTCGTCACGATGGATCAGTACCGCAGAGTCCTTGG 285
    |||||||||||||||||||||||||||||||||||||||||||||||||
251 ATCCAGCACGGTACCCTCGTCACGATGGATCAGTACCGCAGAGTCCTTGG 300

286 GGATAGCTGGGTTCACGTGCAGGATGGACGGATCGTCGCGCTCGGAGTGC 335
    |||||||||||||||||||||||||||||||||||||||||||||||||
301 GGATAGCTGGGTTCACGTGCAGGATGGACGGATCGTCGCGCTCGGAGTGC 350

336 ACGCCGAGTCGGTGCCTCCGCCAGCGGATCGGGTGATCGATGCACGCGGC 385
    |||||||||||||||||||||||||||||||||||||||||||||||||
351 ACGCCGAGTCGGTGCCTCCGCCAGCGGATCGGGTGATCGATGCACGCGGC 400

386 AAGGTCGTGTTACCCGGTTTCATCAATGCCCACACCCATGTGAACCAGAT 435
    |||||||||||||||||||||||||||||||||||||||||||||||||
401 AAGGTCGTGTTACCCGGTTTCATCAATGCCCACACCCATGTGAACCAGAT 450

436 CCTCCTGCGCGGAGGGCCCTCGCACGGCGTCAATTCTATGACTGGCTGT  485
    ||||||||||||||||||||||||||| |||||||||||||||||||||
451 CCTCCTGCGCGGAGGGCCCTCGCACGGAGTCAATTCTATGACTGGCTGT  500

486 TCAACGTTGTGTATCCGGGACAAAAGGCGATGAGACCGGAGGACGTAGCG 535
    |||||||||||||||||||||||||||||||||||||||||||||||||
501 TCAACGTTGTGTATCCGGGACAAAAGGCGATGAGACCGGAGGACGTAGCG 550

536 GTGGCGGTGAGGTTGTATTGTGCGGAAGCTGTGCGCAGCGGGATTACGAC 585
    |||||||||||||||||||||||||||||||||||||||||||||||||
551 GTGGCGGTGAGGTTGTATTGTGCGGAAGCTGTGCGCAGCGGGATTACGAC 600

586 GATCAACGAAAACGCCGATTCGGCCATCTACCCAGGCAACATCGAGGCCG 635
    |||||||||||||||||||||||||||||||||||||||||||||||||
601 GATCAACGAAAACGCCGATTCGGCCATCTACCCAGGCAACATCGAGGCCG 650
```

*FIG. 2A*

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 2B and insert the following therefor:

5/16

```
 636 CGATGGCGGTCTATGGTGAGGTGGGTGTGAGGGTCGTCTACGCCCGCATG  685
     ||||||||||||||||||||||||||||||||||||||||||||||||||
 651 CGATGGCGGTCTATGGTGAGGTGGGTGTGAGGGTCGTCTACGCCCGCATG  700

686 TTCTTTGATCGGATGGACGGGCGCATTCAAGGGTATGTGGACGCCTTGAA  735
     ||||||||||||||||||||||||||||||||||||||||||||||||||
 701 TTCTTTGATCGGATGGACGGGCGCATTCAAGGGTATGTGGACGCCTTGAA  750

736 GGCTCGCTCTCCCCAAGTCGAACTGTGCTCGATCATGGAGGAAACGGCTG  785
     ||||||||||||||||||||||||||||||||||||||||||||||||||
 751 GGCTCGCTCTCCCCAAGTCGAACTGTGCTCGATCATGGAGGAAACGGCTG  800

786 TGGCCAAAGATCGGATCACAGCCCTGTCAGATCAGTATCATGGCACGGCA  835
     ||||||||||||||||||||||||||||||||||||||||||||||||||
 801 TGGCCAAAGATCGGATCACAGCCCTGTCAGATCAGTATCATGGCACGGCA  850

836 GGAGGTCGTATATCAGTTTGGCCCGCTCCTGCCACTACCACGGCGGTGAC  885
     ||||||||||||||||||||||||||||||||||||||||||||||||||
 851 GGAGGTCGTATATCAGTTTGGCCCGCTCCTGCCACTACCACGGCGGTGAC  900

886 AGTTGAAGGAATGCGATGGGCACAAGCCTTCGCCCGTGATCGGGCGGTAA  935
     ||||||||||||||||||||||||||||||||||||||||||||||||||
 901 AGTTGAAGGAATGCGATGGGCACAAGCCTTCGCCCGTGATCGGGCGGTAA  950

936 TGTGGACGCTTCACATGGCGGAGAGCGATCATGATGAGCGGATTCATGGG  985
     ||||||||||||||||||||||||||||||||||||||||||||||||||
 951 TGTGGACGCTTCACATGGCGGAGAGCGATCATGATGAGCGGATTCATGGG 1000

986 ATGAGTCCCGCCGA[T]ACATGGAGTGTTACGGACTCTTGGATGAGCGTCT 1035
     |||||||||||||| |||||||||||||||||||||||||||||||||||
1001 ATGAGTCCCGCCGA[G]ACATGGAGTGTTACGGACTCTTGGATGAGCGTCT 1050

1036 GCAGGTCGCGCATTGCGTGTACTTTGACCGGAAGGATGTTCGGCTGCTGC 1085
     ||||||||||||||||||||||||||||||||||||||||||||||||||
1051 GCAGGTCGCGCATTGCGTGTACTTTGACCGGAAGGATGTTCGGCTGCTGC 1100

1086 ACCGCCACAATGTGAAGGTCGCGTCGCAGGTTGTGAGCAATGCCTACCTC 1135
     ||||||||||||||||||||||||||||||||||||||||||||||||||
1101 ACCGCCACAATGTGAAGGTCGCGTCGCAGGTTGTGAGCAATGCCTACCTC 1150

1136 GGCTCAGGGGTGGCCCCCGTGCCAGAGATGGTGGAGCGCGGCATGGCCGT 1185
     ||||||||||||||||||||||||||||||||||||||||||||||||||
1151 GGCTCAGGGGTGGCCCCCGTGCCAGAGATGGTGGAGCGCGGCATGGCCGT 1200

1186 GGGCATTGGAACAGATAACGGGAATAGTAATGACTCCG[T]AACATGATCG 1235
     ||||||||||||||||||||||||||||||||||||||  ||||||||||
1201 GGGCATTGGAACAGATAACGGGAATAGTAATGACTCCG[A]AACATGATCG 1250

1236 GAGACATGAAGTTTATGGCCCATATTCACCGCGCGGTGCATCGGGATGCG 1285
     ||||||||||||||||||||||||||||||||||||||||||||||||||
1251 GAGACATGAAGTTTATGGCCCATATTCACCGCGCGGTGCATCGGGATGCG 1300
```

*Fig. 2B*

Page 7 of 13

UNITED STATES PATENT AND TRADEMARK OFFICE
CERTIFICATE OF CORRECTION

PATENT NO.    : 6,265,201 B1
DATED         : July 24, 2001
INVENTOR(S)   : Lawrence P. Wackett et al.

It is certified that error appears in the above-identified patent and that said Letters Patent is hereby corrected as shown below:

Drawings (cont'd),
Please delete Fig. 2C and insert the following therefor:

6/16

```
1286 GACGTGCTGACCCCAGAGAAGATTCTTGAAATGGCGACGATCGATGGGGC 1335
     ||||||||||||||||||||||||||||||||||||||||||||||||||
1301 GACGTGCTGACCCCAGAGAAGATTCTTGAAATGGCGACGATCGATGGGGC 1350

1336 GCGTTCGTTGGGAATGGACCACGAGATTGGTTCCATCGAAACCGGCAAGC 1385
     ||||||||||||| ||||||||||||||||||||||||||||||||||||
1351 GCGTTCGTTGGGAATGGACCACGAGATTGGTTCCATCGAAACCGGCAAGC 1400

1386 GCGCGGACCTTATCCTGCTTGACCTGCGTCACCCTCAGACGACTCTTCAC 1435
     |||||||||||||||||||||||||||||||| |||||||||||||
1401 GCGCGGACCTTATCCTGCTTGACCTGCGTCA CCTCAGACGACTC  TCA 1447

1436 CATCATTTGGCGGCCACGATCGTGTTTCAGGCTTACGGCAATGAGGTGGA 1485
     ||||||||||||||||||||||||||||||||||||||||||||||||||
1448 CATCATTTGGCGGCCACGATCGTGTTTCAGGCTTACGGCAATGAGGTGGA 1497

1486 CACTGTCCTGATTGACGGAAACGTTGTGATGGAGAACCGCCGCTTGAGCT 1535
     ||||||||||||||||||||||||||||||||||||||||||||||||||
1498 CACTGTCCTGATTGACGGAAACGTTGTGATGGAGAACCGCCGCTTGAGCT 1547

1536 TTCTTCCCCCTGAACGTGAGTTGGCGTTCCTTGAGGAAGCGCAGAGCCGC 1585
     ||||||||||||||||||||||||||||||||||||||||||||||||||
1548 TTCTTCCCCCTGAACGTGAGTTGGCGTTCCTTGAGGAAGCGCAGAGCCGC 1597

1586 GCCACAGCTATTTTGCAGCGGGCGAACATGGTGGCTAACCCAGCTTGGCG 1635
     ||||||||||||||||||||||||||||||||||||||||||||||||||
1598 GCCACAGCTATTTTGCAGCGGGCGAACATGGTGGCTAACCCAGCTTGGCG 1647

1636 CAGCCTCTAGGAAATGACGCCGTTGCTGCATCCGCCGCCCCTTGAGGAAA 1685
     ||||||||||||||||||||||||||||||||||||||||||||||||||
1648 CAGCCTCTAGGAAATGACGCCGTTGCTGCATCCGCCGCCCCTTGAGGAAA 1697

1686 TCGCTGCCATCTTGGCGCGGCTCGGATTGGGGGGCGGACATGACCTTGAT 1735
     ||||||||||||||||||||||||||||||||||||||||||||||||||
1698 TCGCTGCCATCTTGGCGCGGCTCGGATTGGGGGGCGGACATGACCTTGAT 1747

1736 GGATACAGAATTGCCATGAATGCGGCACTTCCGTCCTTCGCTCGTGTGGA 1785
     ||||||||||||||||||||||||||||||||||||||||||||||||||
1748 GGATACAGAATTGCCATGAATGCGGCACTTCCGTCCTTCGCTCGTGTGGA 1797

1786 ATCGTTGGTAGGTGAGGGTCGACTGCGGGCGCCAGCTTCCCGAAGAAGTG 1835
     |||||||||||||||||||||||||||||||||||||||||||||| |||
1798 ATCGTTGGTAGGTGAGGGTCGACTGCGGGCGCCAGCTTCCCGAAGAGGTG 1847

1836 AAAGGCCCGAG 1846
     |||||||||||
1848 AAAGGCCCGAG 1858
```

*Fig. 2C*

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 3 and insert the following therefor:

7/16

```
  1 ...............ASMVTLTPLFSFSLLNCTRKASRSVMSASSWLVTC  35
                   ||||||||||||||||||||||||||||||||||
  1 SGNFLSAATAALIMKASMVTLTPLFSFSLLNCTRKASRSVMSASSWLVTC  50

36 GMTTQLRCRFFDGIISALRRVTHYWRHIMQTLSIQHGTLVTMDQYRRVLG  85
    |||||||||||||||||||||||||||||||||||||||||||||||||
 51 GMTTQLRCRFFDGIISALRRVTHYWRHIMQTLSIQHGTLVTMDQYRRVLG 100
                                 -START
 86 DSWVHVQDGRIVALGVHAESVPPPADRVIDARGKVVLPGFINAHTHVNQI 135
    |||||||||||||||||||||||||||||||||||||||||||||||||
101 DSWVHVQDGRIVALGVHAESVPPPADRVIDARGKVVLPGFINAHTHVNQI 150

136 LLRGGPSHGRQFYDWLFNVVYPGQKAMRPEDVAVAVRLYCAEAVRSGITT 185
    |||||||||||||||||||||||||||||||||||||||||||||||||
151 LLRGGPSHGRQFYDWLFNVVYPGQKAMRPEDVAVAVRLYCAEAVRSGITT 200

186 INENADSAIYPGNIEAAMAVYGEVGVRVVYARMFFDRMDGRIQGYVDALK 235
    |||||||||||||||||||||||||||||||||||||||||||||||||
201 INENADSAIYPGNIEAAMAVYGEVGVRVVYARMFFDRMDGRIQGYVDALK 250

236 ARSPQVELCSIMEGTAVAKDRITALSDQYHGTAGGRISVWPAPATTTAVT 285
    |||||||||||||:|||||||||||||||||||||||||||||||||||
251 ARSPQVELCSIMESTAVAKDRITALSDQYHGTAGGRISVWPAPATTTAVT 300

286 VEGMRWAQAFARDRAVMWTLHMAESDHDERIHGMSPAEYMECYGLLDERL 335
    |||||||||||||||||||||||||||||||||||||||||||||||||
301 VEGMRWAQAFARDRAVMWTLHMAESDHDERIHGMSPAEYMECYGLLDERL 350

336 QVAHCVYFDRKDVRLLHRHNVKVASQVVSNAYLGSGVAPVPEMVERGMAV 385
    |||||||||||||||||||||||||||||||||||||||||||||||||
351 QVAHCVYFDRKDVRLLHRHNVKVASQVVSNAYLGSGVAPVPEMVERGMAV 400

386 GIGTDNGNSNDSVNMIGDMKFMAHIHRAVHRDADVLTPEKILEMATIDGA 435
    ||||||||||||:||||||||||||||||||||||||||||||||||||
401 GIGTDNGNSNDSANMIGDMKFMAHIHRAVHRDADVLTPEKILEMATIDGA 450

436 RSLGMDHEIGSIETGKRADLILLDLRHPQTTPHHLAATIVFQAYGNEVD  485
    ||||||||||||||||||||||||||| -  .||||||||||||||||
451 RSLGMDHEIGSIETGKRADLILLDLRHLRRLS.HHLAATIVFQAYGNEVD  499

486 TVLIDGNVVMENRRLSFLPPERELAFLEEAQSRATAILQRANMVANPAWR 535
    |||||||||||||||||||||||||||||||||||||||||||||||||
500 TVLIDGNVVMENRRLSFLPPERELAFLEEAQSRATAILQRANMVANPAWR 549
    STOP
536 SLOEMTPLLHPPPLEEIAAILARLGLGGGHDLDGYRIAMNAALPSFARVE 585
    |||||||||||||||||||||||||||||||||||||||||||||||||
550 SLOEMTPLLHPPPLEEIAAILARLGLGGGHDLDGYRIAMNAALPSFARVE 599

586 SLVGEGRLRAPASRRSE... 602
    |||||||||||||||:|
600 SLVGEGRLRAPASRRGERPE 619
```

Fig. 3

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 4 and insert the following therefor:

*8/16*

```
  1 .....SAATAALIMKASMVTLTPLFSFSLLNCTRKASRSVMSASSWLVTC  45
        |||||||||||||||||||||||||||||||||||||||||||||
  1 SGNFLSAATAALIMKASMVTLTPLFSFSLLNCTRKASRSVMSASSWLVTC  50

46 GMTTQLRCRFFDGVISALRRVTHYWRHIMQTLSIQHGTLVTMDQYRRVLG  95
    ||||||||||||| |||||||||||||||||||||||||||||||||||
 51 GMTTQLRCRFFDGIISALRRVTHYWRHIMQTLSIQHGTLVTMDQYRRVLG 100
                                  .START
 96 DSWVHVQDGRIVALGVHAESVPPPADRVIDARGKVVLPGFINAHTHVNQI 145
    |||||||||||||||||||||||||||||||||||||||||||||||||
101 DSWVHVQDGRIVALGVHAESVPPPADRVIDARGKVVLPGFINAHTHVNQI 150

146 LLRGGPSHGRQFYDWLFNVVYPGQKAMRPEDVAVAVRLYCAEAVRSGITT 195
    |||||||||||||||||||||||||||||||||||||||||||||||||
151 LLRGGPSHGRQFYDWLFNVVYPGQKAMRPEDVAVAVRLYCAEAVRSGITT 200

196 INENADSAIYPGNIEAAMAVYGEVGVRVVYARMFFDRMDGRIQGYVDALK 245
    |||||||||||||||||||||||||||||||||||||||||||||||||
201 INENADSAIYPGNIEAAMAVYGEVGVRVVYARMFFDRMDGRIQGYVDALK 250

246 ARSPQVELCSIMEETAVAKDRITALSDQYHGTAGGRISVWPAPATTTAVT 295
    |||||||||||||||||||||||||||||||||||||||||||||||||
251 ARSPQVELCSIMEETAVAKDRITALSDQYHGTAGGRISVWPAPATTTAVT 300

296 VEGMRWAQAFARDRAVMWTLHMAESDHDERIHGMSPADYMECYGLLDERL 345
    ||||||||||||||||||||||||||||||||||||| |||||||||||
301 VEGMRWAQAFARDRAVMWTLHMAESDHDERIHGMSPAEYMECYGLLDERL 350

346 QVAHCVYFDRKDVRLLHRHNVKVASQVVSNAYLGSGVAPVPEMVERGMAV 395
    |||||||||||||||||||||||||||||||||||||||||||||||||
351 QVAHCVYFDRKDVRLLHRHNVKVASQVVSNAYLGSGVAPVPEMVERGMAV 400

396 GIGTDNGNSNDSVNMIGDMKFMAHIHRAVHRDADVLTPEKILEMATIDGA 445
    ||||| |||||| ||||||||||||||||||||||||||||||||||||
401 GIGTDNGNSNDSANMIGDMKFMAHIHRAVHRDADVLTPEKILEMATIDGA 450

446 RSLGMDHEIGSIETGKRADLILLDLRHPQTTPHHHLAATIVFQAYGNEVD 495
    |||||||||||||||||||||||||||  . |||||||||||||||||
451 RSLGMDHEIGSIETGKRADLILLDLRHLRRLS.HHLAATIVFQAYGNEVD 499

496 TVLIDGNVVMENRRLSFLPPERELAFLEEAQSRATAILQRANMVANPAWR 545
    |||||||||||||||||||||||||||||||||||||||||||||||||
500 TVLIDGNVVMENRRLSFLPPERELAFLEEAQSRATAILQRANMVANPAWR 549
    STOP
546 SLQEMTPLLHPPPLEEIAAILARLGLGGGHDLDGYRIAMNAALPSFARVE 595
    |||||||||||||||||||||||||||||||||||||||||||||||||
550 SLQEMTPLLHPPPLEEIAAILARLGLGGGHDLDGYRIAMNAALPSFARVE 599

596 SLVGEGRLRAPASRRSERPE 615
    ||||||||||||||| ||||
600 SLVGEGRLRAPASRRGERPE 619
```

*Fig. 4*

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 5A and insert the following therefor:

*9/16*

```
                              C
545  CGGTATCGGGGAATTNTTGAGCGCGGCCACAGCAGCCNTGATCATGAAGG  496
     ||   |  ||:||||||||||||||||||||:|||||||||||
  1  ...CTCGGGTAACTTCTTGAGCGCGGCCACAGCAGCCTTGATCATGAAGG   47

495  CGAGCATGGTGACCTNGACGCCGTNTTTTNGTTNTTTTTTGTTGAACTGC  446
     ||||||||||||||:|||||||  :  |||:   |:  1  |||||||||||||
 48  CGAGCATGGTGACCTTGACGCCGCTCTTTTCGTTCTCTTTGTTGAACTGC   97

445  ACGCGAAAGG[TTCCAGGTCGGTGATGTCCGCGTCGTCGTGGTTGGTGAC  397
     ||||||||||||||||||||||||||||||||||||||||||||||
 98  ACGCGAAAGG[TTCCAGGTCGGTGATGTCCGCGTCGTCGTGGTTGGTGAC  147

396  GTGCGGGATGACCACCCAGNTGCGGTGCAGGTTTTTCGATGGCATAATAT  347
     ||||||||||||||||||:|||||||||||||||||||||||||
148  GTGCGGGATGACCACCCAGTTGCGGTGCAGGTTTTTCGATGGCATAATAT  197

346  CTGCGTTGCGACGTGTAACACACTANTGGAGACATATCATGCAAACGCTC  297
     ||||||||||||||||||||||||||:|||||||||||||||||||||||
198  CTGCGTTGCGACGTGTAACACACTATTGGAGACATATCATGCAAACGCTC  247

296  AGCATCCAGCACGGTACCCTCGTCACGATGGATCAGTACCGCAGAGTCCT  247
     ||||||||||||||||||||||||||||||||||||||||||||||||||
248  AGCATCCAGCACGGTACCCTCGTCACGATGGATCAGTACCGCAGAGTCCT  297
                C
246  TGGGGATAGNTGGGTTCACGTGCAGGATGGACGGATCGTCGCGCTCGGAG  197
     ||||||||:|||||||||||||||||||||||||||||||||||||||
298  TGGGGATAGCTGGGTTCACGTGCAGGATGGACGGATCGTCGCGCTCGGAG  347

196  TGCACGCCGAGTCGGTGCCTCCGCCAGCGGATCGGGTGATCGATGCACGC  147
     ||||||||||||||||||||||||||||||||||||||||||||||||||
348  TGCACGCCGAGTCGGTGCCTCCGCCAGCGGATCGGGTGATCGATGCACGC  397

146  GGCAAGGTCGTGTTACCCGGTTTCATCAATGCCCACACCCATGTGAACCA   97
     ||||||||||||||||||||||||||||||||||||||||||||||||||
398  GGCAAGGTCGTGTTACCCGGTTTCATCAATGCCCACACCCATGTGAACCA  447
                                C              C
 96  GATCCTCCTGCGCGGAGGGCCNTCGCACGG[TGTCAATTNTATGACTGGC   47
     |||||||||||||||||||:||||||||| |||||||:|||||||||
448  GATCCTCCTGCGCGGAGGGCCCTCGCACGG[AGTCAATTCTATGACTGGC  497

46  TGTTCAACGTTGTGTATCCGGGACAAAAGGCGATGAGACCGGAGGA....    1
     ||||||||||||||||||||||||||||||||||||||||||||
498  TGTTCAACGTTGTGTATCCGGGACAAAAGGCGATGAGACCGGAGGACGTA  547
```

*Fig. 5A*

UNITED STATES PATENT AND TRADEMARK OFFICE
CERTIFICATE OF CORRECTION

PATENT NO. : 6,265,201 B1
DATED : July 24, 2001
INVENTOR(S) : Lawrence P. Wackett et al.

It is certified that error appears in the above-identified patent and that said Letters Patent is hereby corrected as shown below:

Drawings (cont'd),
Please delete Fig. 5B and insert the following therefor:

10/16

```
  1 ...CCTGCGCGGAGGGCCTCGCACGGGGTCAATTCTATGACTGGCTGT  47
         |||||||||||||| ||||||  |||||||||||||||||||||
451    CCTCCTGCGCGGAGGGCCTTGCACGGAGTCAATTCTATGACTGGCTGT 500
                                                   G
 48    TCAACGTTGTGTATCCGGGACAAAAGGCGATGAGACCGGAGGACGTANCG  97
       |||||||||||||||||||||||||||||||||||||||||||||||| ||
501    TCAACGTTGTGTATCCGGGACAAAAGGCGATGAGACCGGAGGACGTAGCG 550

98    GTGGCGGTGAGGTTGTATTGTGCGGAAGCTGTGCGCAGCGGGATTACGAC 147
       ||||||||||||||||||||||||||||||||||||||||||||||||||
551    GTGGCGGTGAGGTTGTATTGTGCGGAAGCTGTGCGCAGCGGGATTACGAC 600
                    G
148    GATCAACGAAAACNCCGATTCGGCCATCTACCCAGGCAACATCGAGGCCG 197
       |||||||||||| |||||||||||||||||||||||||||||||||||||
601    GATCAACGAAAACGCCGATTCGGCCATCTACCCAGGCAACATCGAGGCCG 650

198    CGATGGCGGTCTATGGTGAGGTGGGTGTGACGGTCGTCTACGCCCGCATG 247
       |||||||||||||||||||||||||||||||| |||||||||||||||||
651    CGATGGCGGTCTATGGTGAGGTGGGTGTGAGGGTCGTCTACGCCCGCATG 700

248    TTCTTTGATCGGATGGACGGGCGCATTCAAGGGTATGTGGACGCCTTGAA 297
       ||||||||||||||||||||||||||||||||||||||||||||||||||
701    TTCTTTGATCGGATGGACGGGCGCATTCAAGGGTATGTGGACGCCTTGAA 750
                                         G     G
298    GGCTCGCTCTCCCCAAGTCGAACTGTGCTCGATCATGGANGAAACNGCTG 347
       ||||||||||||||||||||||||||||||||||||||||| ||||| ||||
751    GGCTCGCTCTCCCCAAGTCGAACTGTGCTCGATCATGGAGGAAACGGCTG 800
                                 G     G   G       G
348    TGGCCAAAGATCGGATCACANCCCTGTCANATCANTATCATGGCACNGCA 397
       |||||||||||||||||||| ||||||| |||| |||||||||||||| ||
801    TGGCCAAAGATCGGATCACAGCCCTGTCAGATCAGTATCATGGCACGGCA 850
       G         G                           G
398    NGAGGTCCTATATCANTTTTGGCCCGCTCCTGCCACTACCACNGCGGTGAC 447
        ||||||  ||||||| |||||||||||||||||||||||||| |||||||
851    GGAGGTCGTATATCAGTTTGGCCCGCTCCTGCCACTACCACGGCGGTGAC 900

448    ATTTAAANGAATCCATGGGCCA....ACCTCCCCCGTGATCCGGCGGTAA 493
       || || ||||  |   || ||      | || ||||||||| ||||||||
901    AGTTGAAGGAATGCGATGGGCACAAGCCTTCGCCCGTGATCGGGCGGTAA 950

494    TGTGAC.................................... 499
       ||||
951    TGTGGACGCTTCACATGGCGGAGAGCGATCATGATGAGCGGATTCATGGG 1000
```

Fig. 5B

UNITED STATES PATENT AND TRADEMARK OFFICE
CERTIFICATE OF CORRECTION

PATENT NO.    : 6,265,201 B1
DATED         : July 24, 2001
INVENTOR(S)   : Lawrence P. Wackett et al.

It is certified that error appears in the above-identified patent and that said Letters Patent is hereby corrected as shown below:

Drawings (cont'd),
Please delete Fig. 5D and insert the following therefor:

12/16

```
   1 .......CGGCCACGATCGTGTTTCAGGCTTACGGCAATGAGGTGGACAC  43
           ||||||||||||||||||||||||||||||||||||
1451 CATTTGGCGGCCACGATCGTGTTTCAGGCTTACGGCAATGAGGTGGACAC 1500

44 TGTCCTGATTGACGGAAACGTTGTGATGGAGAACCGCCGCTTGAGCTTTC  93
     ||||||||||||||||||||||||||||||||||||||||||||||||||
1501 TGTCCTGATTGACGGAAACGTTGTGATGGAGAACCGCCGCTTGAGCTTTC 1550

94 TTCCCCCTGAACGTGAGTTGGCGTTCCTTGAGGAAGCGCAGAGCCGCGCC 143
     ||||||||||||||||||||||||||||||||||||||||||||||||||
1551 TTCCCCCTGAACGTGAGTTGGCGTTCCTTGAGGAAGCGCAGAGCCGCGCC 1600

144 ACAGCTATTTTGCA  GGGCG  AACATGGTGGCTAACCCAGCTTGGCGCA 193
     ||||||||||||||  |||||  |||||||||||||||||||||||||||
1601 ACAGCTATTTTGCA  GGGCG  AACATGGTGGCTAACCCAGCTTGGCGCA 1649

194 GCCTCTAGGAAATGACGCCGTTGCTGCATCCGCCGCCCCTTGAGGAAATC 243
     ||||||||||||||||||||||||||||||||||||||||||||||||||
1650 GCCTCTAGGAAATGACGCCGTTGCTGCATCCGCCGCCCCTTGAGGAAATC 1699

244 GCTGCCATCTTGGCGCGGCTCGGATTGGGGGGCGGACATGACCTTGATGG 293
     ||||||||||||||||||||||||||||||||||||||||||||||||||
1700 GCTGCCATCTTGGCGCGGCTCGGATTGGGGGGCGGACATGACCTTGATGG 1749

294 ATACAGAATTGCCATGAATGCGGCACTTCCGTCCTTCGCTCGTGTGGAAT 343
     ||||||||||||||||||||||||||||||||||||||||||||||||||
1750 ATACAGAATTGCCATGAATGCGGCACTTCCGTCCTTCGCTCGTGTGGAAT 1799

344 CGTTGGTAGGTGAGGGTCGACTGCGGGCGCCAGCTTCCCGAAGAGGTGAA 393
     ||||||||||||||||||||||||||||||||||||||||||||||||||
1800 CGTTGGTAGGTGAGGGTCGACTGCGGGCGCCAGCTTCCCGAAGAGGTGAA 1849

394 AGCCCGAGGATCCTCTAGAGTCCGATTTTTCCGATGTCATCACCGGCGCG 443
     || ||  |
1850 AGGCCCGAG.......................................  1858
```

Fig. 5D

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1858 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CTCGGGTAAC TTCTTGAGCG CGGCCACAGC AGCCTTGATC ATGAAGGCGA GCATGGTGAC      60

CTTGACGCCG CTCTTTTCGT TCTCTTTGTT GAACTGCACG CGAAAGGCTT CCAGGTCGGT     120

GATGTCCGCG TCGTCGTGGT TGGTGACGTG CGGGATGACC ACCCAGTTGC GGTGCAGGTT     180

TTTCGATGGC ATAATATCTG CGTTGCGACG TGTAACACAC TATTGGAGAC ATATCATGCA     240

AACGCTCAGC ATCCAGCACG GTACCCTCGT CACGATGGAT CAGTACCGCA GAGTCCTTGG     300

GGATAGCTGG GTTCACGTGC AGGATGGACG GATCGTCGCG CTCGGAGTGC ACGCCGAGTC     360

GGTGCCTCCG CCAGCGGATC GGGTGATCGA TGCACGCGGC AAGGTCGTGT TACCCGGTTT     420

CATCAATGCC CACACCCATG TGAACCAGAT CCTCCTGCGC GGAGGGCCCT CGCACGGACG     480

TCAATTCTAT GACTGGCTGT TCAACGTTGT GTATCCGGGA CAAAAGGCGA TGAGACCGGA     540

GGACGTAGCG GTGGCGGTGA GGTTGTATTG TGCGGAAGCT GTGCGCAGCG GGATTACGAC     600

GATCAACGAA AACGCCGATT CGGCCATCTA CCCAGGCAAC ATCGAGGCCG CGATGGCGGT     660

CTATGGTGAG GTGGGTGTGA GGGTCGTCTA CGCCCGCATG TTCTTTGATC GGATGGACGG     720

GCGCATTCAA GGGTATGTGG ACGCCTTGAA GGCTCGCTCT CCCCAAGTCG AACTGTGCTC     780

GATCATGGAG GAAACGGCTG TGGCCAAAGA TCGGATCACA GCCCTGTCAG ATCAGTATCA     840

TGGCACGGCA GGAGGTCGTA TATCAGTTTG GCCCGCTCCT GCCACTACCA CGGCGGTGAC     900

AGTTGAAGGA ATGCGATGGG CACAAGCCTT CGCCCGTGAT CGGGCGGTAA TGTGGACGCT     960

TCACATGGCG GAGAGCGATC ATGATGAGCG GATTCATGGG ATGAGTCCCG CCGAGTACAT    1020

GGAGTGTTAC GGACTCTTGG ATGAGCGTCT GCAGGTCGCG CATTGCGTGT ACTTTGACCG    1080

GAAGGATGTT CGGCTGCTGC ACCGCCACAA TGTGAAGGTC GCGTCGCAGG TTGTGAGCAA    1140

TGCCTACCTC GGCTCAGGGG TGGCCCCCGT GCCAGAGATG GTGGAGCGCG GCATGGCCGT    1200
```

```
GGGCATTGGA ACAGATAACG GGAATAGTAA TGACTCCGCA ACCATGATCG AGACATGAA    1260

GTTTATGGCC CATATTCACC GCGCGGTGCA TCGGGATGCG GACGTGCTGA CCCCAGAGAA    1320

GATTCTTGAA ATGGCGACGA TCGATGGGGC GCGTTCGTTG GGAATGGACC ACGAGATTGG    1380

TTCCATCGAA ACCGGCAAGC GCGCGGACCT TATCCTGCTT GACCTGCGTC ACCTCAGACG    1440

ACTCTCACAT CATTTGGCGG CCACGATCGT GTTTCAGGCT TACGGCAATG AGGTGGACAC    1500

TGTCCTGATT GACGGAAACG TTGTGATGGA GAACCGCCGC TTGAGCTTTC TTCCCCCTGA    1560

ACGTGAGTTG GCGTTCCTTG AGGAAGCGCA GAGCCGCGCC ACAGCTATTT TGCAGCGGGC    1620

GAACATGGTG GCTAACCCAG CTTGGCGCAG CCTCTAGGAA ATGACGCCGT TGCTGCATCC    1680

GCCGCCCCTT GAGGAAATCG CTGCCATCTT GGCGCGGCTC GGATTGGGGG GCGGACATGA    1740

CCTTGATGGA TACAGAATTG CCATGAATGC GGCACTTCCG TCCTTCGCTC GTGTGGAATC    1800

GTTGGTAGGT GAGGGTCGAC TGCGGGCGCC AGCTTCCCGA AGAGGTGAAA GGCCCGAG     1858
```

(2) INFORMATION FOR SEQ ID NO:2:

(i) SEQUENCE CHARACTERISTICS:
        (A) LENGTH: 473 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gln Thr Leu Ser Ile Gln His Gly Thr Leu Val Thr Met Asp Gln
 1               5                  10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

Arg Val Ile Asp Ala Arg Gly Lys Val Val Leu Pro Gly Phe Ile Asn
        50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Tyr Pro Gly Gln
                85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
        210                 215                 220

Gly Met Arg Trp Ala Gln Ala Phe Ala Arg Asp Arg Ala Val Met Trp
225                 230                 235                 240
```

```
Thr Leu His Met Ala Glu Ser Asp His Asp Glu Arg Ile His Gly Met
            245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
            290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Ala Asn
            325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
            370                 375                 380

Glu Thr Gly Lys Arg Ala Asp Leu Ile Leu Leu Asp Leu Arg His Leu
385                 390                 395                 400

Arg Arg Leu Ser His His Leu Ala Ala Thr Ile Val Phe Gln Ala Tyr
            405                 410                 415

Gly Asn Glu Val Asp Thr Val Leu Ile Asp Gly Asn Val Val Met Glu
            420                 425                 430

Asn Arg Arg Leu Ser Phe Leu Pro Pro Glu Arg Glu Leu Ala Phe Leu
            435                 440                 445

Glu Glu Ala Gln Ser Arg Ala Thr Ala Ile Leu Gln Arg Ala Asn Met
            450                 455                 460

Val Ala Asn Pro Ala Trp Arg Ser Leu
465                 470

(2) INFORMATION FOR SEQ ID NO:3:

(i) SEQUENCE CHARACTERISTICS:
        (A) LENGTH: 1808 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCGAGCATGG TGACCTTGAC GCCGCTCTTT TCGTTCTCTT TGTTGAACTG CACGCGAAAG      60

GCTTCCAGGT CGGTGATGTC CGCGTCGTCG TGGTTGGTGA CGTGCGGGAT GACCACCCAG     120

TTGCGGTGCA GGTTTTTCGA TGGCATAATA TCTGCGTTGC GACGTGTAAC ACACTATTGG     180

AGACATATCA TGCAAACGCT CAGCATCCAG CACGGTACCC TCGTCACGAT GGATCAGTAC     240

CGCAGAGTCC TTGGGGATAG CTGGGTTCAC GTGCAGGATG GACGGATCGT CGCGCTCGGA     300

GTGCACGCCG AGTCGGTGCC TCCGCCAGCG GATCGGGTGA TCGATGCACG CGGCAAGGTC     360

GTGTTACCCG GTTTCATCAA TGCCCACACC CATGTGAACC AGATCCTCCT GCGCGGAGGG     420

CCCTCGCACG GCGTCAATT CTATGACTGG CTGTTCAACG TTGTGTATCC GGGACAAAAG     480

GCGATGAGAC CGGAGGACGT AGCGGTGGCG GTGAGGTTGT ATTGTGCGGA AGCTGTGCGC     540

AGCGGGATTA CGACGATCAA CGAAAACGCC GATTCGGCCA TCTACCCAGG CAACATCGAG     600
```

```
GCCGCGATGG CGGTCTATGG TGAGGTGGGT GTGAGGGTCG TCTACGCCCG CATGTTCTTT        660

GATCGGATGG ACGGGCGCAT TCAAGGGTAT GTGGACGCCT TGAAGGCTCG CTCTCCCCAA        720

GTCGAACTGT GCTCGATCAT GGAGGGAACG GCTGTGGCCA AGATCGGAT CACAGCCCTG         780

TCAGATCAGT ATCATGGCAC GGCAGGAGGT CGTATATCAG TTTGGCCCGC TCCTGCCACT        840

ACCACGGCGG TGACAGTTGA AGGAATGCGA TGGGCACAAG CCTTCGCCCG TGATCGGGCG        900

GTAATGTGGA CGCTTCACAT GGCGGAGAGC GATCATGATG AGCGGATTCA TGGGATGAGT        960

CCCGCCGAGT ACATGGAGTG TTACGGACTC TTGGATGAGC GTCTGCAGGT CGCGCATTGC       1020

GTGTACTTTG ACCGGAAGGA TGTTCGGCTG CTGCACCGCC ACAATGTGAA GGTCGCGTCG       1080

CAGGTTGTGA GCAATGCCTA CCTCGGCTCA GGGGTGGCCC CCGTGCCAGA GATGGTGGAG       1140

CGCGGCATGG CCGTGGGCAT TGGAACAGAT AACGGGAATA GTAATGACTC CGTAAACATG       1200

ATCGGAGACA TGAAGTTTAT GGCCCATATT CACCGCGCGG TGCATCGGGA TGCGGACGTG       1260

CTGACCCCAG AGAAGATTCT TGAAATGGCG ACGATCGATG GGGCGCGTTC GTTGGGAATG       1320

GACCACGAGA TTGGTTCCAT CGAAACCGGC AAGCGCGCGG ACCTTATCCT GCTTGACCTG       1380

CGTCACCCTC AGACGACTCC TCACCATCAT TTGGCGGCCA CGATCGTGTT TCAGGCTTAC       1440

GGCAATGAGG TGGACACTGT CCTGATTGAC GGAAACGTTG TGATGGAGAA CCGCCGCTTG       1500

AGCTTTCTTC CCCCTGAACG TGAGTTGGCG TTCCTTGAGG AAGCGCAGAG CCGCGCCACA       1560

GCTATTTTGC AGCGGGCGAA CATGGTGGCT AACCCAGCTT GGCGCAGCCT CTAGGAAATG       1620

ACGCCGTTGC TGCATCCGCC GCCCCTTGAG GAAATCGCTG CCATCTTGGC GCGGCTCGGA       1680

TTGGGGGGCG GACATGACCT TGATGGATAC AGAATTGCCA TGAATGCGGC ACTTCCGTCC       1740

TTCGCTCGTG TGGAATCGTT GGTAGGTGAG GGTCGACTGC GGGCGCCAGC TTCCCGAAGA       1800

AGTGAAAG                                                                1808

(2) INFORMATION FOR SEQ ID NO:4:

(i) SEQUENCE CHARACTERISTICS:
        (A) LENGTH: 1846 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GAGCGCCGCC ACAGCAGCCT TGATCATGAA GGCGAGCATG GTGACCTTGA CGCCGCTCTT         60

TTCGTTCTCT TTGTTGAACT GCACGCGAAA GGCTTCCAGG TCGGTGATGT CCGCGTCGTC        120

GTGGTTGGTG ACGTGCGGGA TGACCACCCA GTTGCGGTGC AGGTTTTTCG ATGGCGTAAT        180

ATCTGCGTTG CGACGTGTAA CACACTATTG GAGACATATC ATGCAAACGC TCAGCATCCA        240

GCACGGTACC CTCGTCACGA TGGATCAGTA CCGCAGAGTC CTTGGGGATA GCTGGGTTCA        300

CGTGCAGGAT GGACGGATCG TCGCGCTCGG AGTGCACGCC GAGTCGGTGC CTCCGCCAGC        360

GGATCGGGTG ATCGATGCAC GCGGCAAGGT CGTGTTACCC GGTTTCATCA ATGCCCACAC        420

CCATGTGAAC CAGATCCTCC TGCGCGGAGG GCCCTCGCAC GGGCGTCAAT TCTATGACTG        480

GCTGTTCAAC GTTGTGTATC CGGGACAAAA GGCGATGAGA CCGGAGGACG TAGCGGTGGC        540

GGTGAGGTTG TATTGTGCGG AAGCTGTGCG CAGCGGGATT ACGACGATCA ACGAAAACGC        600

CGATTCGGCC ATCTACCCAG GCAACATCGA GGCCGCGATG GCGGTCTATG GTGAGGTGGG        660

TGTGAGGGTC GTCTACGCCC GCATGTTCTT TGATCGGATG GACGGGCGCA TTCAAGGGTA        720
```

```
TGTGGACGCC TTGAAGGCTC GCTCTCCCCA AGTCGAACTG TGCTCGATCA TGGAGGAAAC    780

GGCTGTGGCC AAAGATCGGA TCACAGCCCT GTCAGATCAG TATCATGGCA CGGCAGGAGG    840

TCGTATATCA GTTTGGCCCG CTCCTGCCAC TACCACGGCG GTGACAGTTG AAGGAATGCG    900

ATGGGCACAA GCCTTCGCCC GTGATCGGGC GGTAATGTGG ACGCTTCACA TGGCGGAGAG    960

CGATCATGAT GAGCGGATTC ATGGGATGAG TCCCGCCGAT TACATGGAGT GTTACGGACT   1020

CTTGGATGAG CGTCTGCAGG TCGCGCATTG CGTGTACTTT GACCGGAAGG ATGTTCGGCT   1080

GCTGCACCGC CACAATGTGA AGGTCGCGTC GCAGGTTGTG AGCAATGCCT ACCTCGGCTC   1140

AGGGGTGGCC CCCGTGCCAG AGATGGTGGA GCGCGGCATG GCCGTGGGCA TTGGAACAGA   1200

TAACGGGAAT AGTAATGACT CCGTAAACAT GATCGGAGAC ATGAAGTTTA TGGCCCATAT   1260

TCACCGCGCG GTGCATCGGG ATGCGGACGT GCTGACCCCA GAGAAGATTC TTGAAATGGC   1320

GACGATCGAT GGGGCGCGTT CGTTGGGGAT GGACCACGAG ATTGGTTCCA TCGAAACCGG   1380

CAAGCGCGCG GACCTTATCC TGCTTGACCT GCGTCACCCT CAGACGACTC CTCACCATCA   1440

TTTGGCGGCC ACGATCGTGT TTCAGGCTTA CGGCAATGAG GTGGACACTG TCCTGATTGA   1500

CGGAAACGTT GTGATGGAGA ACCGCCGCTT GAGCTTTCTT CCCCCTGAAC GTGAGTTGGC   1560

GTTCCTTGAG GAAGCGCAGA GCCGCGCCAC AGCTATTTTG CAGCGGGCGA ACATGGTGGC   1620

TAACCCAGCT TGGCGCAGCC TCTAGGAAAT GACGCCGTTG CTGCATCCGC CGCCCCTTGA   1680

GGAAATCGCT GCCATCTTGG CGCGGCTCGG ATTGGGGGGC GGACATGACC TTGATGGATA   1740

CAGAATTGCC ATGAATGCGG CACTTCCGTC CTTCGCTCGT GTGGAATCGT TGGTAGGTGA   1800

GGGTCGACTG CGGGCGCCAG CTTCCCGAAG AAGTGAAAGG CCCGAG              1846
```

(2) INFORMATION FOR SEQ ID NO:5:

(i) SEQUENCE CHARACTERISTICS:
        (A) LENGTH: 601 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Ala Ser Met Val Thr Leu Thr Pro Leu Phe Ser Phe Ser Leu Leu Asn
1               5                   10                  15

Cys Thr Arg Lys Ala Ser Arg Ser Val Met Ser Ala Ser Ser Trp Leu
            20                  25                  30

Val Thr Cys Gly Met Thr Thr Gln Leu Arg Cys Arg Phe Phe Asp Gly
        35                  40                  45

Ile Ile Ser Ala Leu Arg Arg Val Thr His Tyr Trp Arg His Ile Met
    50                  55                  60

Gln Thr Leu Ser Ile Gln His Gly Thr Leu Val Thr Met Asp Gln Tyr
65                  70                  75                  80

Arg Arg Val Leu Gly Asp Ser Trp Val His Val Gln Asp Gly Arg Ile
                85                  90                  95

Val Ala Leu Gly Val His Ala Glu Ser Val Pro Pro Ala Asp Arg
            100                 105                 110

Val Ile Asp Ala Arg Gly Lys Val Val Leu Pro Gly Phe Ile Asn Ala
        115                 120                 125

His Thr His Val Asn Gln Ile Leu Leu Arg Gly Gly Pro Ser His Gly
    130                 135                 140

Arg Gln Phe Tyr Asp Trp Leu Phe Asn Val Val Tyr Pro Gly Gln Lys
```

-continued

```
145                 150                 155                 160
Ala Met Arg Pro Glu Asp Val Ala Val Ala Val Arg Leu Tyr Cys Ala
                165                 170                 175
Glu Ala Val Arg Ser Gly Ile Thr Thr Ile Asn Glu Asn Ala Asp Ser
                180                 185                 190
Ala Ile Tyr Pro Gly Asn Ile Glu Ala Ala Met Ala Val Tyr Gly Glu
                195                 200                 205
Val Gly Val Arg Val Val Tyr Ala Arg Met Phe Phe Asp Arg Met Asp
            210                 215                 220
Gly Arg Ile Gln Gly Tyr Val Asp Ala Leu Lys Ala Arg Ser Pro Gln
225                 230                 235                 240
Val Glu Leu Cys Ser Ile Met Glu Gly Thr Ala Val Ala Lys Asp Arg
                245                 250                 255
Ile Thr Ala Leu Ser Asp Gln Tyr His Gly Thr Ala Gly Gly Arg Ile
                260                 265                 270
Ser Val Trp Pro Ala Pro Ala Thr Thr Thr Ala Val Thr Val Glu Gly
                275                 280                 285
Met Arg Trp Ala Gln Ala Phe Ala Arg Asp Arg Ala Val Met Trp Thr
                290                 295                 300
Leu His Met Ala Glu Ser Asp His Asp Glu Arg Ile His Gly Met Ser
305                 310                 315                 320
Pro Ala Glu Tyr Met Glu Cys Tyr Gly Leu Leu Asp Glu Arg Leu Gln
                325                 330                 335
Val Ala His Cys Val Tyr Phe Asp Arg Lys Asp Val Arg Leu Leu His
                340                 345                 350
Arg His Asn Val Lys Val Ala Ser Gln Val Val Ser Asn Ala Tyr Leu
                355                 360                 365
Gly Ser Gly Val Ala Pro Val Pro Glu Met Val Glu Arg Gly Met Ala
        370                 375                 380
Val Gly Ile Gly Thr Asp Asn Gly Asn Ser Asn Asp Ser Val Asn Met
385                 390                 395                 400
Ile Gly Asp Met Lys Phe Met Ala His Ile His Arg Ala Val His Arg
                405                 410                 415
Asp Ala Asp Val Leu Thr Pro Glu Lys Ile Leu Glu Met Ala Thr Ile
                420                 425                 430
Asp Gly Ala Arg Ser Leu Gly Met Asp His Glu Ile Gly Ser Ile Glu
            435                 440                 445
Thr Gly Lys Arg Ala Asp Leu Ile Leu Leu Asp Leu Arg His Pro Gln
        450                 455                 460
Thr Thr Pro His His His Leu Ala Ala Thr Ile Val Phe Gln Ala Tyr
465                 470                 475                 480
Gly Asn Glu Val Asp Thr Val Leu Ile Asp Gly Asn Val Val Met Glu
                485                 490                 495
Asn Arg Arg Leu Ser Phe Leu Pro Pro Glu Arg Glu Leu Ala Phe Leu
                500                 505                 510
Glu Glu Ala Gln Ser Arg Ala Thr Ala Ile Leu Gln Arg Ala Asn Met
            515                 520                 525
Val Ala Asn Pro Ala Trp Arg Ser Leu Glu Met Thr Pro Leu Leu His
        530                 535                 540
Pro Pro Pro Leu Glu Glu Ile Ala Ala Ile Leu Ala Arg Leu Gly Leu
545                 550                 555                 560
Gly Gly Gly His Asp Leu Asp Gly Tyr Arg Ile Ala Met Asn Ala Ala
                565                 570                 575
```

```
Leu Pro Ser Phe Ala Arg Val Glu Ser Leu Val Gly Glu Gly Arg Leu
            580                 585                 590

Arg Ala Pro Ala Ser Arg Arg Ser Glu
            595                 600

(2) INFORMATION FOR SEQ ID NO:6:

(i) SEQUENCE CHARACTERISTICS:
        (A) LENGTH: 614 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ser Ala Ala Thr Ala Ala Leu Ile Met Lys Ala Ser Met Val Thr Leu
1               5                   10                  15

Thr Pro Leu Phe Ser Phe Ser Leu Leu Asn Cys Thr Arg Lys Ala Ser
            20                  25                  30

Arg Ser Val Met Ser Ala Ser Ser Trp Leu Val Thr Cys Gly Met Thr
            35                  40                  45

Thr Gln Leu Arg Cys Arg Phe Phe Asp Gly Val Ile Ser Ala Leu Arg
        50                  55                  60

Arg Val Thr His Tyr Trp Arg His Ile Met Gln Thr Leu Ser Ile Gln
65                  70                  75                  80

His Gly Thr Leu Val Thr Met Asp Gln Tyr Arg Arg Val Leu Gly Asp
                85                  90                  95

Ser Trp Val His Val Gln Asp Gly Arg Ile Val Ala Leu Gly Val His
            100                 105                 110

Ala Glu Ser Val Pro Pro Ala Asp Arg Val Ile Asp Ala Arg Gly
            115                 120                 125

Lys Val Val Leu Pro Gly Phe Ile Asn Ala His Thr His Val Asn Gln
        130                 135                 140

Ile Leu Leu Arg Gly Gly Pro Ser His Gly Arg Gln Phe Tyr Asp Trp
145                 150                 155                 160

Leu Phe Asn Val Val Tyr Pro Gly Gln Lys Ala Met Arg Pro Glu Asp
            165                 170                 175

Val Ala Val Ala Val Arg Leu Tyr Cys Ala Glu Ala Val Arg Ser Gly
            180                 185                 190

Ile Thr Thr Ile Asn Glu Asn Ala Asp Ser Ala Ile Tyr Pro Gly Asn
        195                 200                 205

Ile Glu Ala Ala Met Ala Val Tyr Gly Glu Val Gly Val Arg Val Val
210                 215                 220

Tyr Ala Arg Met Phe Phe Asp Arg Met Asp Gly Arg Ile Gln Gly Tyr
225                 230                 235                 240

Val Asp Ala Leu Lys Ala Arg Ser Pro Gln Val Glu Leu Cys Ser Ile
            245                 250                 255

Met Glu Glu Thr Ala Val Ala Lys Asp Arg Ile Thr Ala Leu Ser Asp
            260                 265                 270

Gln Tyr His Gly Thr Ala Gly Gly Arg Ile Ser Val Trp Pro Ala Pro
        275                 280                 285

Ala Thr Thr Thr Ala Val Thr Val Glu Gly Met Arg Trp Ala Gln Ala
            290                 295                 300

Phe Ala Arg Asp Arg Ala Val Met Trp Thr Leu His Met Ala Glu Ser
305                 310                 315                 320
```

```
Asp His Asp Glu Arg Ile His Gly Met Ser Pro Ala Asp Tyr Met Glu
            325                 330                 335
Cys Tyr Gly Leu Leu Asp Glu Arg Leu Gln Val Ala His Cys Val Tyr
        340                 345                 350
Phe Asp Arg Lys Asp Val Arg Leu Leu His Arg His Asn Val Lys Val
            355                 360                 365
Ala Ser Gln Val Val Ser Asn Ala Tyr Leu Gly Ser Gly Val Ala Pro
    370                 375                 380
Val Pro Glu Met Val Glu Arg Gly Met Ala Val Gly Ile Gly Thr Asp
385                 390                 395                 400
Asn Gly Asn Ser Asn Asp Ser Val Asn Met Ile Gly Asp Met Lys Phe
            405                 410                 415
Met Ala His Ile His Arg Ala Val His Arg Asp Ala Asp Val Leu Thr
            420                 425                 430
Pro Glu Lys Ile Leu Glu Met Ala Thr Ile Asp Gly Ala Arg Ser Leu
            435                 440                 445
Gly Met Asp His Glu Ile Gly Ser Ile Glu Thr Gly Lys Arg Ala Asp
    450                 455                 460
Leu Ile Leu Leu Asp Leu Arg His Pro Gln Thr Thr Pro His His His
465                 470                 475                 480
Leu Ala Ala Thr Ile Val Phe Gln Ala Tyr Gly Asn Glu Val Asp Thr
            485                 490                 495
Val Leu Ile Asp Gly Asn Val Val Met Glu Asn Arg Arg Leu Ser Phe
            500                 505                 510
Leu Pro Pro Glu Arg Glu Leu Ala Phe Leu Glu Glu Ala Gln Ser Arg
        515                 520                 525
Ala Thr Ala Ile Leu Gln Arg Ala Asn Met Val Ala Asn Pro Ala Trp
    530                 535                 540
Arg Ser Leu Glu Met Thr Pro Leu Leu His Pro Pro Leu Glu Glu
545                 550                 555                 560
Ile Ala Ala Ile Leu Ala Arg Leu Gly Leu Gly Gly His Asp Leu
            565                 570                 575
Asp Gly Tyr Arg Ile Ala Met Asn Ala Ala Leu Pro Ser Phe Ala Arg
        580                 585                 590
Val Glu Ser Leu Val Gly Glu Gly Arg Leu Arg Ala Pro Ala Ser Arg
            595                 600                 605
Arg Ser Glu Arg Pro Glu
    610

(2) INFORMATION FOR SEQ ID NO:7:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGGTATCGGG GAATTCTTGA GCGCGGCCAC AGCAGCCNTG ATCATGAAGG CGAGCATGGT      60

GACCTNGACG CCGTNTTTTN GTTNTTTTTT GTTGAACTGC ACGCGAAAGG TTCCAGGTCG     120

GTGATGTCCG CGTCGTCGTG GTTGGTGACG TGCGGGATGA CCACCCAGNT GCGGTGCAGG    180

TTTTTCGATG GCATAATATC TGCGTTGCGA CGTGTAACAC ACTANTGGAG ACATATCATG    240
```

| | |
|---|---|
| CAAACGCTCA GCATCCAGCA CGGTACCCTC GTCACGATGG ATCAGTACCG CAGAGTCCTT | 300 |
| GGGGATAGCT GGGTTCACGT GCAGGATGGA CGGATCGTCG CGCTCGGAGT GCACGCCGAG | 360 |
| TCGGTGCCTC CGCCAGCGGA TCGGGTGATC GATGCACGCG GCAAGGTCGT GTTACCCGGT | 420 |
| TTCATCAATG CCCACACCCA TGTGAACCAG ATCCTCCTGC GCGGAGGGCC CTCGCACGGG | 480 |
| CGTCAATTCT ATGACTGGCT GTTCAACGTT GTGTATCCGG ACAAAAGGC GATGAGACCG | 540 |
| GAGGA | 545 |

(2) INFORMATION FOR SEQ ID NO:8:

(i) SEQUENCE CHARACTERISTICS:
        (A) LENGTH: 499 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | |
|---|---|
| CCTGCGCGGA GGGCCTCCGC ACGGGCGTCA ATTCTATGAC TGGCTGTTCA ACGTTGTGTA | 60 |
| TCCGGGACAA AAGGCGATGA GACCGGAGGA CGTAGCGGTG GCGGTGAGGT TGTATTGTGC | 120 |
| GGAAGCTGTG CGCAGCGGGA TTACGACGAT CAACGAAAAC GCCGATTCGG CCATCTACCC | 180 |
| AGGCAACATC GAGGCCGCGA TGGCGGTCTA TGGTGAGGTG GGTGTGAGGG TCGTCTACGC | 240 |
| CCGCATGTTC TTTGATCGGA TGGACGGGCG CATTCAAGGG TATGTGGACG CCTTGAAGGC | 300 |
| TCGCTCTCCC CAAGTCGAAC TGTGCTCGAT CATGGAGGAA ACGGCTGTGG CCAAAGATCG | 360 |
| GATCACAGCC CTGTCAGATC AGTATCATGG CACGGCAGGA GGTCCTATAT CAGTTTGGCC | 420 |
| CGCTCCTGCC ACTACCACGG CGGTGACATT TAAANGAATC CATGGGCCAA CCTCCCCCGT | 480 |
| GATCCGGCGG TAATGTGAC | 499 |

(2) INFORMATION FOR SEQ ID NO:9:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | |
|---|---|
| TNGCAGGTTG TGAGCATGCT ACTTCGGTTC AGGNGTGGCC CCCGTGCCAG AGATGGTGGA | 60 |
| GCGCGGCATG GCCGTGGGCA TTGGAACAGA TAACGGGAAT AGTAATGACT CCGTAAACAT | 120 |
| GATCGGAGAC ATGAAGTTTA TGGCCCATAT TCACCGCGCG GTGCATCGGG ATGCGGACGT | 180 |
| GCTGACCCCA GAGAAGATTN TTGAAATGGC GACGATCGAT GGGGCGCGTT TCGTTGGGGA | 240 |
| TGGACCACGA GATTGGTTCC ATCGAAACCG GCAAGCGCGC GGACCTTATC CTGCTTGACC | 300 |
| TGCGTCACCC TCAGACGACT CCTCACCATC ATTTGGCGGC CACGATCGTG TTTCAGGCTT | 360 |

(2) INFORMATION FOR SEQ ID NO:10:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:10:

```
CGGCCACGAT CGTGTTTCAG GCTTACGGCA ATGAGGTGGA CACTGTCCTG ATTGACGGAA      60
ACGTTGTGAT GGAGAACCGC CGCTTGAGCT TTCTTCCCCC TGAACGTGAG TTGGCGTTCC     120
TTGAGGAAGC GCAGAGCCGC GCCACAGCTA TTTTGCATCG GGCGAAACAT GGTGGCTAAC     180
CCAGCTTGGC GCAGCCTCTA GGAAATGACG CCGTTGCTGC ATCCGCCGCC CCTTGAGGAA     240
ATCGCTGCCA TCTTGGCGCG GCTCGGATTG GGGGCGGAC ATGACCTTGA TGGATACAGA      300
ATTGCCATGA ATGCGGCACT TCCGTCCTTC GCTCGTGTGG AATCGTTGGT AGGTGAGGGT     360
CGACTGCGGG CGCCAGCTTC CCGAAGAGGT GAAAGCCCGA GGATCCTCTA GAGTCCGATT     420
TTTCCGATGT CATCACCGGC GCG                                              443
```

(2) INFORMATION FOR SEQ ID NO:11:

(i) SEQUENCE CHARACTERISTICS:
  (A) LENGTH: 505 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:11:

```
CCTGCGCGGA GGCCTCCGCA CGGGCGTCAA TTCTATGACT GGCTGTTCAA CGTTGTGTAT      60
CCGGGACAAA AGGCGATGAG ACCGGAGGAC GTANCGGTGG CGGTGAGGTT GTATTGTGCG     120
GAAGCTGTGC GCAGCGGGAT TACGACGATC AACGAAAACG CCGATTCGGC CATCTACCCA     180
GGCAACATCG AGGCCGCGAT GCGGTCTAT GGTGAGGTGG GTGTGAGGGT CGTCTACGCC      240
CGCATGTTCT TTGATCGGAT GGACGGGCGC ATTCAAGGGT ATGTGGACGC CTTGAAGGCT     300
CGCTCTCCCC AAGTCGAACT GTGCTCGATC ATGGAGGAAA CGGCTGTGGC CAAAGATCGG     360
ATCACANCCC TGTCAGATCA NTATCATGGC ACGGCANGAG GTCCTATATC ANTTTGGCCC     420
GCTCCTGCCA CTACCACNGC GGTGACATTT NAANGAATTC CATNGGCACA ACCTTCCCCC     480
GTGATCNGGC GGTAATGTNG ACCCA                                            505
```

(2) INFORMATION FOR SEQ ID NO:12:

(i) SEQUENCE CHARACTERISTICS:
  (A) LENGTH: 144 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:12:

```
Pro His Gly Arg Gln Phe Tyr Asp Trp Leu Phe Asn Val Leu Tyr Pro
1               5                  10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Ala Leu Lys Ala Arg
                85                  90                  95
```

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
        115                 120                 125

Gly Arg Ile Ser Val Trp Pro Ala Pro Ala Thr Thr Thr Ala Val Thr
    130                 135                 140

(2) INFORMATION FOR SEQ ID NO:13:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Ser His Gly Arg Gln Phe Tyr Asp Trp Leu Phe Asn Val Leu Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Thr Leu Lys Ala Arg
                85                  90                  95

Ser Pro Gln Val Glu Leu Cys Ser Ile Met Glu Glu Thr Ala Val Ala
            100                 105                 110

Lys Asp Arg Ile Thr Ala Leu Ser Asp Gln Tyr His Gly Thr Ala Gly
        115                 120                 125

Gly Arg Ile Ser Val Trp Pro Ala Pro Ala Thr Thr Thr Ala Val Thr
    130                 135                 140

(2) INFORMATION FOR SEQ ID NO:14:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Pro His Gly Arg Gln Phe Tyr Asp Trp Leu Phe Asn Val Val Tyr Pro
1               5                   10                  15

Gly Gln Lys Ala Met Arg Pro Glu Asp Val Ala Val Ala Val Arg Leu
            20                  25                  30

Tyr Cys Ala Glu Ala Val Arg Ser Gly Ile Thr Thr Ile Asn Glu Asn
        35                  40                  45

Ala Asp Ser Ala Ile Tyr Pro Gly Asn Ile Glu Ala Ala Met Ala Val
    50                  55                  60

Tyr Gly Glu Val Gly Val Arg Val Val Tyr Ala Arg Met Phe Phe Asp
65                  70                  75                  80

Arg Met Asp Gly Arg Ile Gln Gly Tyr Val Asp Ala Leu Lys Ala Arg

```
                          85                  90                  95
Ser Pro Gln Val Glu Leu Cys Ser Ile Met Glu Thr Ala Val Ala
                    100                 105                 110

Lys Asp Arg Ile Thr Ala Leu Ser Asp Gln Tyr His Gly Thr Ala Gly
            115                 120                 125

Gly Arg Ile Ser Val Trp Pro Ala Pro Ala Thr Thr Thr Ala Val Thr
    130                 135                 140
```

(2) INFORMATION FOR SEQ ID NO:15:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Ser His Gly Arg Gln Phe Tyr Asp Trp Leu Phe Asn Val Leu Tyr Pro
1               5                   10                  15

Gly Gln Lys Ala Met Arg Pro Glu Asp Val Ala Val Ala Val Arg Leu
                20                  25                  30

Tyr Cys Ala Glu Ala Val Arg Ser Gly Ile Thr Thr Ile Asn Glu Asn
            35                  40                  45

Asn Ala Asp Ser Ala Ile Tyr Pro Gly Asn Ile Glu Ala Ala Met Ala
    50                  55                  60

Val Tyr Gly Glu Val Gly Val Arg Val Tyr Ala Arg Met Phe Phe
65                  70                  75                  80

Asp Arg Met Asp Gly Arg Ile Gln Gly Tyr Val Asp Thr Leu Lys Ala
                85                  90                  95

Arg Ser Pro Gln Val Glu Leu Cys Ser Ile Met Glu Thr Ala Val
                    100                 105                 110

Ala Lys Asp Arg Ile Thr Ala Leu Ser Asp Gln Tyr His Gly Thr Ala
            115                 120                 125

Gly Gly Arg Ile Ser Val Trp Pro Ala Pro Ala Thr Thr Thr Ala Val
    130                 135                 140

Thr
145
```

(2) INFORMATION FOR SEQ ID NO:16:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Ser His Gly Arg Gln Phe Tyr Asp Trp Leu Phe Asn Val Val Tyr Pro
1               5                   10                  15

Gly Gln Lys Ala Met Arg Pro Glu Asp Val Ala Val Ala Val Arg Leu
                20                  25                  30

Tyr Cys Ala Glu Ala Val Arg Ser Gly Ile Thr Thr Ile Asn Glu Asn
            35                  40                  45

Ala Asp Ser Ala Ile Tyr Pro Gly Asn Ile Glu Ala Ala Met Ala Val
    50                  55                  60
```

-continued

```
Tyr Gly Glu Val Gly Val Arg Val Val Tyr Ala Arg Met Phe Phe Asp
 65                  70                  75                  80

Arg Met Asp Gly Arg Ile Gln Gly Tyr Val Asp Ala Leu Lys Ala Arg
                 85                  90                  95

Ser Pro Gln Val Glu Leu Cys Ser Ile Met Glu Glu Thr Ala Val Ala
                100                 105                 110

Lys Asp Arg Ile Thr Ala Leu Ser Asp Gln Tyr His Gly Thr Ala Gly
            115                 120                 125

Gly Arg Ile Ser Val Trp Pro Ala Pro Ala Thr Thr Thr Ala Val Thr
        130                 135                 140
```

(2) INFORMATION FOR SEQ ID NO:17:

(i) SEQUENCE CHARACTERISTICS:
        (A) LENGTH: 1633 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
CGCGAAAGGC TTCCAGGTCG GTGATGTCCG CGTCGTCGTG GTTGGTGACG TGCGGGATGA    60
CCACCCAGTC GCGGTGCAGG TTTTTCGATG GCATAATATC TGCGTTGCGA CGTGTAACAC   120
ACTATTGGAG ACATATCATG CAAACGCTCA GCATCCAGCA CGGTACCCTC GTCACGATGG   180
ATCAATACCG CAGAGTCCTT GGGGATAGCT GGGTTCACGT GCAGGATGGA CGGATCGTCG   240
CGCTCGGAGT GCACGCCAAG TCGGTGCCTC CGCCAGCGGA TCGGGTGATC GATGCACGCG   300
GCAAGGTCGT GTTACCCGGT TTCATCAATG CCCACACCCA TGTGAACCAG ATCCTCCTGC   360
GCGGAGGGCC CTCGCACGGG CGTCAATTCT ATGACTGGCT GTTCAACGTT GTGTATCCGG   420
GACAAAAGGC GATGAGACCG GAGGACGTAG CGGTGGCGGT GAGGTTGTAT TGTGCGGAAG   480
CTGTGCGCAG CGGGATTACG ACGATCAACG AAAACGCCGA TTCGGCCATC TACCCAGGCA   540
ACATCGAGGC CGCGATGGCG GTCTATGGTG AGGTGGGTGT GAGGGTCGTC TACGCCCGCA   600
TGTTCTTTGA TCGGATGGAC GGGCGCATTC AAGGGTATGT GGACGCCTTG AAGGCTCGCT   660
CTCCCCAAGT CGAACTGTGC TCGATCATGG AGGAAACGGC TGTGGCCAAA GATCGGATCA   720
CAGCCCTGTC AGATCAGTAT CATGGCACGG CAGGAGGTCG TATATCAGTT TGGCCCGCTC   780
CTGCCACTAC CACGGCGGTG ACAGTTGAAG GAATGCGATG GCACAAGCC TTCGCCCGTG    840
ATCGGGCGGT AATGTGGACG CTTCACATGG CGGAGAGCGA TCATGATGGG CGGATTCATG   900
GGATGAGTCC CGCCGAGTAC ATGGAGTGTT ACGGACTCTT GGATGAGCGT CTGCAGGTCG   960
CGCATTGCGT GTACTTTGAC CGGAAGGATG TTCGGCTGCT GCACCGCCAC AATGTGAAGG  1020
TCGCGTCGCA GGTTGTGAGC AATGCCTACC TCGGCTCAGG GGTGGCCCCC GTGCCAGAGA  1080
TGGTGGAGCG CGGCATGGCC GTGGGCATTG GAACAGATAA CGGGAATAGT AATGACTCCG  1140
TAAACATGAT CGGAGACATG AAGTTTATGG CCCATATTCA CCGCGCGGTG CATCGGGATG  1200
CGGACGTGCT GACCCCAGAG AAGATTCTTG AAATGGCGAC GATCGATGGG GCGCGTTCGT  1260
TGGGGATGGA CCACGAGATT GGTTCCATCG AAACCGGCAA GCGCGCGGAC CTTATCCTGC  1320
TTGACCTGCG TCACCCTCAG ACGACTCCTC ACCATCATTT GGCGGCCACG ATCGTGTTTC  1380
AGGCTTACGG CAATGAAGTG GACACTGTCC TGATTGACGG AAACGTTGTG ATGGAGAACC  1440
GCTGCTTGAG CTTTCTTCCC CCTGAACGTG AGTTGGCGTT CCTTGAGGGA GCGCAGAGCC  1500
GCGCCACAGC TATTTTGCAG CGGGCGAACA TGGTGGCTAA CCCAGCTTGG CGCAGCCTCT  1560
```

-continued

```
AGGAAATGAC GCCGTTGCTG CATCCGCCGC CCCTTGAGGA AATCGCTGCC ATCTTGGCGC    1620

GGCTCGGATT GGG                                                       1633
```

(2) INFORMATION FOR SEQ ID NO:18:

(i) SEQUENCE CHARACTERISTICS:
        (A) LENGTH: 1598 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
TCGTGGTTGG TGACGTGCGG GATGACCACC CAGTCGCGGT GCAGGTTTTT CGATGGCATA      60

ATATCTGCGT TGCGACGTGT AACACACTAT TGGAGACATA TCATGCAAAC GCTCAGCATC     120

CAGCACGGTA CCCTCGTCAC GATGGATCAG TACCGCAGAG TCCTTGGGGA TAGCTGGGTT     180

CACGTGCAGG ATGGACGGAT CGTCGCGCTC GGAGTGCACG CCGAGTCGGT GCCTCCGCCA     240

GCGGATCGGG TGATCGATGC ACGCGGCAAG GTCGTGTTAC CCGGTTTCAT CAATGCCCAC     300

ACCCATGTGA ACCAGATCCT CCTGCGCGGA GGGCCCTCGC ACGGGCGTCA ATTCTATGAC     360

TGGCTGTTCA ACGTTGTGTA TCCGGGACAA AAGGCGATGA GACCGGAGGA CGTAGCGGTG     420

GCGGTGAGGT TGTATTGTGC GGAAGCTGTG CGCAGCGGGA TTACGACGAT CAACGAAAAC     480

GCCGATTCGG CCATCTACCC AGGCAACATC GAGGCCGCGA TGGCGGTCTA TGGTGAGGTG     540

GGTGTGAGGG TCGTCTACGC CCGCATGTTC TTTGATCGGA TGGACGGGCG CATTCAAGGG     600

TATGTGGACG CCTTGAAGGC TCGCTCTCCC CAAGTCGAAC TGTGCTCGAT CATGGAGGAA     660

ACGGCTGTGG CCAAAGATCG GATCACAGCC CTGTCAGATC AGTATCATGG CACGGCAGGA     720

GGTCGTATAT CAGTTTGGCC CGCTCCTGCC ACTACCACGG CGGTGACAGT TGAAGGAATG     780

CGATGGGCAC AAGCCTTCGC CCGTGATCGG GCGGTAATGT GGACGCTTCA CATGGCGGAG     840

AGCGATCATG ATGAGCGGAT TCATGGGATG AGTCCCGCCG AGTACATGGA GTGTCACGGA     900

CTCTTGGATG AGCGTCTGCA GGTCGCGCAT TGCGTGTACT TTGACCGGAA GGATGTTCGG     960

CTGCTGCACC GCCACAATGT GAAGGTCGCG TCGCAGGTTG TGAGCAATGC CTACCTCGGC    1020

TCAGGGGTGG CCCCCGTGCC AGAGATGGTG GAGCGCGGCA TGGCCATGGG CATTGGAACA    1080

GATAACGGGA ATAGTAATGA CTCCGTAAAC ATGATCGGAG ACATGAAGTT TATGGCCCAT    1140

ATTCACCGCG CGGTGCATCG GGATGCGGAC GTGCTGACCC AGAGAAGAT TCTTGAAATG     1200

GCGACGATCG ATGGGCGCG TTCGTTGGGA ATGGACCACG AGATTGGTTC CATCGAAACC     1260

GGCAAGCGCG CGGACCTTAT CCTGCTTGAC CTGCGTCACC CTCAGACGAC TCCTCACCAT    1320

CATTTGGCGG CCACGATCGT GTTTCAGGCT TACGGCAATG AGGTGGACAC TGTCCTGATT    1380

GACGGAAACG TTGTGATGGA GAACCGCCGC TTGAGCTTTC TTCCCCCTGA ACGTGAGTTG    1440

GCGTTCCTTG AGGAAGCGCA GAGCCGCGCC ACAGCTATTT GCAGCGGGC GAACATGGTG     1500

GCTAACCCAG CTTGGCGCAG CCTCTAGGAA ATGACGCCGT TGCTGCATCC GCCGCCCCTT    1560

GAGGAAATCG CTGCCATCTT GGCGCGGCTC GGATTGGG                            1598
```

(2) INFORMATION FOR SEQ ID NO:19:

(i) SEQUENCE CHARACTERISTICS:
        (A) LENGTH: 1586 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:19:

```
ACGTGCGGGA TGACCACCCA GTTGCGGTGC AGGTTTTTCG ATGGCGTAAT ATCTGCGTTG     60

CGACGTGTAA CACACTATTG GAGACATATC ATGCAAACGC TCAGCATCCA GCACGGTACC    120

CTCGTCACGA TGGATCAGTA CCGCAGAGTC CTTGGGGATA GCTGGGTTCA CGTGCAGGAT    180

GGACGGATCG TCGCGCTCGG AGTGCACGCC GAGTCGGTGC CTCCGCCAGC GGATCGGGTG    240

ATCGATGCAC GCGGCAAGGT CGTGTTACCC GGTTTCATCA ATGCCCACAC CCATGTGAAC    300

CAGATCCTCC TGCGCGGAGG GCCCTCGCAC GGGCGTCAAT TCTATGACTG GCTGTTCAAC    360

GTTGTGTATC CGGGACAAAA GGCGATGAGA CCTGAGGACG TAGCGGTGGC GGTGAGGTTG    420

TATTGTGCGG AAGCTGTGCG CAGCGGGATT ACGACGATCA ACGAAAACGC CGATTCGGCC    480

ATCTACCCAG GCAACATCGA GGCCGCGATG GCGGTCTATG GTGAGGTGGG TGTGAGGGTC    540

GTCTACGCCC GCATGTTCTT TGATCGGATG GACGGGCGCA TTCAAGGGTA TGTGGACGCC    600

TTGAAGGCTC GCTCTCCCCA AGTCGAACTG TGCTCGATCA TGGAGGAAAC GGCTGTGGCC    660

AAAGATCGGA TCACAGCCCT GTCAGATCAG TATCATGGCA CGGCAGGAGG TCGTATATCA    720

GTTTGGCCCG CTCCTGCCAC TACCACGGCG GTGACAGTTG AAGGAATGCG ATGGGCACAA    780

GCCTTCGCCC GTGATCGGGC GGTAATGTGG ACGCTTCACA TGGCGGAGAG CGATCATGAT    840

GAGCGGATTC ATGGGATGAG TCCCGCCGAG TACATGGAGT GTTACGGACT CTTGGATGAG    900

CGTCTGCAGG TCGCGCATTG CGTGTACTTT GACCGGAAGG ATGTTCGGCT GCTGCACCGC    960

CACAATGTGA AGGTCGCGTC GCAGGTTGTG AGCAATGCCT ACCTCGGCTC AGGGGTGGCC   1020

CCCGTGCCAG AGATGGTGGA GCGCGGCATG GCCGTGGGCA TTGGAACAGA TAACGGGAAT   1080

AGTAATGACT CCGTAAACAT GATCGGAGAC ATGAAGTTTA TGGCCCATAT TCACCGCGCG   1140

GTGCATCGGG ATGCGGACGT GCTGACCCCA GAGAAGATTC TTGAAATGGC GACAATCGAT   1200

GGGGCGCGTT CGTTGGGAAT GGACCACGAG ATTGGTTCCA TCGAAACCGG CAAGCGCGCG   1260

GACCTTATCC TGCTTGACCT GCGTCACCCT CAGACGACTC CTCACCATCA TTTGGCGGCC   1320

ACGATCGTGT TTCAGGCTTA CGGCAATGAG GTGGACACTG TCCTGATTGA CGGAAACGTT   1380

GTGATGGAGA ACCGCCGCTT GAGCTTTCTT CCCCCTGAAC GTGAGTTGGC GTTCCTTGAG   1440

GAAGCGCAGA GCCGCGCCAC AGCTATTTTG CAGCGGGCGA ACATGGTGGC TAACCCAGCT   1500

TGGCGCAGCC TCTAGGAAAT GACGCCGTTG CTGCATCCGC TGCCCCTTGA GGAAATCGCT   1560

GCCATCTTGG CGCGGCTCGG ATTGGG                                       1586
```

(2) INFORMATION FOR SEQ ID NO:20:

(i) SEQUENCE CHARACTERISTICS:
        (A) LENGTH: 1597 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CGTGGTTGGT GACGTGGGGG ATGACCACCC AGTCGCGGTG CAGGTTTTTC GATGGCATAA     60

TATCTGCGTT GCGACGTGTA ACACACTATT GGAGACATAT CATGCAAACG CTCAGCATCC    120

AGCACGGTAC CCTCGTCACG ATGGATCAGT ACCGCAGAGT CCTTGGGGAT AGCTGGGTTC    180
```

```
ACGTGCAGGA TGGACGGATC GTCGCGCTCG GAGTGCACGC CGAGTCGGTG CCTCCGCCAG      240

CGGATCAGGT GATCGATGCA CGCGGCAAGG TCGTGTTACC CGGTTTCATC AATGCCCACA      300

CCCATGTGAA CCAGATCCTC CTGCGCGGAG GGCCCTCGCA CGGGCGTCAA TTCCATGACT      360

GGCTGTTCAA CGTTGTGTAT CCGGGACAAA AGGCGATGAG ACCGGAGGAC GTAGCGGTGG      420

CGGTGAGGTT GTATTGTGCA GAAGCTGTGC GCAGCGGGAT TACGACGATT AACGAAAACG      480

CCGATTCGGC CATCTACCCA GGCAACATCG AGGCCGCGAT GGCGGTCTAT GGTGAGGTGG      540

GTGTGAGGGT CGTCTACGCC CGCATGTTCT TTGATCGGAT GGACGGGCGC ATTCAAGGGT      600

ATGTGGACGC CTTGAAGGCT CGCTCTCCCC AAGTCGAACT GTGCTCGATC ATGGAGGAAA      660

CGGCTGTGGC CAAAGATCGG ATCACAGCCC TGTCAGATCA GTATCATGGC ACGGCAGGAG      720

GTCGTATATC AGTTTGGCCC GCTCCTGCCA CTACCACGGC GGTGACAGTT GAAGGAATGC      780

GATGGGCACA AGCCTTCGCC CGTGATCGGG CGGTAATGTG GACGCTTCAC ATGGCGGAGA      840

GCGATCATGA TGGGCGGATT CATGGGATGA GTCCCGCCGA GTACATGGAG TGTTACGGAC      900

TCTTGGATGA GCGTCTGCAG GTCGCGCATT GCGTGTACTT TGACCGGAAG GATGTTCGGC      960

TGCTGCACCG CCACAATGTG AAGGTCGCGT CGCAGGTTGT GAGCAATGCC TACCTCGGCT     1020

CAGGGGTGGC CCCCGTGCCA GAGATGGTGG AGCGCGGCAT GGCCGTGGGC ATTGGAACAG     1080

ATAACGGGAA TAGTAATGAC TCCGTAAACA TGATCGGAGA CATGAAGTTT ATGGCCCATA     1140

TTCACCGCGC GGTGCATCGG GATGCGGACG TGCTGACCCC AGAGAAGATT CTTGAAATGG     1200

CAACGATCGA TGGGGCGCGT TCGTTGGGAA TGGACCACGA GATTGGTTCC ATCGAAACCG     1260

GCAAGCGCGC GGACCTTATC CTGCTTGACC TGCGTCACCC TCAGACGACT CCTCACCATC     1320

ATTTGGCGGC CACGATCGTG TTTCAGGCTT ACGGCAATGA GGTGGACACT GTCCTGATTG     1380

ACGGAAACGT TGTGATGGAG AACCGCCGCT TGAGCTTTCT TCCCCCTGAA CGTGAGTTGG     1440

CGTTCCTTGA GGAAGCGCAG AGCCGCGCCA CAGCTATTTT GCAGCGGGCG AACATGGTGG     1500

CTAACCCAGC TTGGCGCAGC CTCTAGGAAA TGACGCCGTT GCTGCATCCG CCGCCCCTTG     1560

AGGAAATCGC TGCCATCTTG GCGCGGCTCG GATTGGG                             1597
```

(2) INFORMATION FOR SEQ ID NO:21:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GTGACCTTGA CGCCGCTCTT TTCGTTCTCT TGTTGAACT GCACGCGAAT GGCTTCCAGT        60

TCGATGATGT CCGCGTCGTC GTGGTTGGTG ACGTGCGGGA TGACCACCCA GTCGCGGTGC      120

AGGTTTTTCG ATGGCATAAT ATCTGCGTTG CGACGTGTAA CACACTATTG GAGACATATC      180

ATGCAAACGC TCAGCATCCA GCACGGTACC CTCGTCACGA TGGATCAGTA CCGCAGAGTC      240

CTTGGGGATA GCTGGGTTCA CGTGCAGGAT GGACGGATCG TCGCGCTCGG AGTGCACGCC      300

GAGTCGGTGC CTCCGCCAGC GGATCGGTG ATTGATGCAC GCGGCAAGGT CGTGTTACCC      360

GGTTTCATCA ATGCCCACAC CCATGTGAAC CAGATCCTCC TGCGCGGAGG CCTCGCACGG      420

GCGTCAATTC TATGACTGGC TGTTCAACGT TGTGTATCCG GGACAAAAGG CGATGAGACC      480

GGAGGACGTA GCGGTGGCGG TGAGGTTGTA TTGTGCGGAA GCTGTGCGCA GCGGGATTAC      540
```

```
                                                        -continued

GACGATCAAC GAAAACGCCG ATTCGGCCAT CTACCCAGGC AACATCGAGG CCGCGATGGC    600

GGTCTATGGT GAGGTGGGTG TGAGGGTCGT CTACGCCCGC ATGTTCTTTG ATCGGATGGA    660

CAGGCGCATT CAAGGGTATG TGGACGCCTT GAAGGCTCGC TCTCCCCAAG TCGAACTGTG    720

CTCGATCATG GAGGAAACGG CTGTGGCCAA AGATCGGATC ACAGCCCTGT CAGATCAGTA    780

TCATGGCACG GCAGGAGGTC GTATATCAGT TTGGCCCGCT CCTGCCACTA CCACGGCGGT    840

GACAGTTGAA GGAATGCGAT GGGCACAAGC CTTCGCCCGT GATCGGGCGG TAATGTGGAC    900

GCTTCACATG GCGGAGAGCG ATCATGATGA GCGGATTCAT GGGATGAGTC CGCCGAGTA    960

CATGGAGTGT TACGGACTCT TGGATGAGCG TCTGCAGGTC GCGCATTGCG TGTACTTTGA   1020

CCGGAAGGAT ATTCGGCTGC TGCACCGCCA CAATGTGAAG GTCGCGTCGC AGGCTGTGAG   1080

CAATGCCTAC CTCGGCTCAG GGGTGGCCCC CGTGCCAGAG ATGGTGGAGC GCGGCATGGC   1140

CGTGGGCATT GGAACAGATA ACGGGAATAG TAATGACTCC GTAAACATGA TCGGAGACAT   1200

GAAGTTTATG GCCCATATTC ACCGCGCGGT GCATCGGGAT GCGGACGTGC TGACCCCAGA   1260

GAAGATTCTT GAAATGGCGA CGATCGATGG GGCGCGTTCG TTGGGAATGG ACCACGAGAT   1320

TGGTTCCATC GAAACCGGCA AGCGCGCGGA CCTTATCCTG CTTGACCTGC GTCACCCTCA   1380

GACGACTCCT CACCATCATT TGGCGGCCAC GATCGTGTTT CAGGCTTACG GCAATGAGGT   1440

GGACACTGTC CTGATTGACG GAAACGTTGT GATGGAGAAC CGCCGCTTGA GCTTTCTTCC   1500

CCCTGAACGT GAGTTGGCGT TCCTTGAGGA AGCGCAGAGC CGCGCCACAG CTATTTTGCA   1560

GCGGGCGAAC ATGGTGGCCA ACCCAGCTTG GCGCAGCCTC TAGGAAATGA CGCCGTTGCT   1620

GCATCCGCCG CCCCTTGAGG AAATCGCTGC CATCTTGGCG CAGCTCGGAT TGGG           1674

(2) INFORMATION FOR SEQ ID NO:22:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Lys Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
```

-continued

```
145                 150                 155                 160
Asp Gly Arg Ile Gln Gly Tyr Val Asp Ala Leu Lys Ala Arg Ser Pro
                165                 170                 175
Gln Val Glu Leu Cys Ser Ile Met Glu Glu Thr Ala Val Ala Lys Asp
                180                 185                 190
Arg Ile Thr Ala Leu Ser Asp Gln Tyr His Gly Thr Ala Gly Gly Arg
                195                 200                 205
Ile Ser Val Trp Pro Ala Pro Ala Thr Thr Thr Ala Val Thr Val Glu
            210                 215                 220
Gly Met Arg Trp Ala Gln Ala Phe Ala Arg Asp Arg Ala Val Met Trp
225                 230                 235                 240
Thr Leu His Met Ala Glu Ser Asp His Asp Gly Arg Ile His Gly Met
                245                 250                 255
Ser Pro Ala Glu Tyr Met Glu Cys Tyr Gly Leu Leu Asp Glu Arg Leu
                260                 265                 270
Gln Val Ala His Cys Val Tyr Phe Asp Arg Lys Asp Val Arg Leu Leu
                275                 280                 285
His Arg His Asn Val Lys Val Ala Ser Gln Val Val Ser Asn Ala Tyr
                290                 295                 300
Leu Gly Ser Gly Val Ala Pro Val Pro Glu Met Val Glu Arg Gly Met
305                 310                 315                 320
Ala Val Gly Ile Gly Thr Asp Asn Gly Asn Ser Asn Asp Ser Val Asn
                325                 330                 335
Met Ile Gly Asp Met Lys Phe Met Ala His Ile His Arg Ala Val His
                340                 345                 350
Arg Asp Ala Asp Val Leu Thr Pro Glu Lys Ile Leu Glu Met Ala Thr
                355                 360                 365
Ile Asp Gly Ala Arg Ser Leu Gly Met Asp His Glu Ile Gly Ser Ile
                370                 375                 380
Glu Thr Gly Lys Arg Ala Asp Leu Ile Leu Leu Asp Leu Arg His Pro
385                 390                 395                 400
Gln Thr Thr Pro His His His Leu Ala Ala Thr Ile Val Phe Gln Ala
                405                 410                 415
Tyr Gly Asn Glu Val Asp Thr Val Leu Ile Asp Gly Asn Val Val Met
                420                 425                 430
Glu Asn Arg Cys Leu Ser Phe Leu Pro Pro Glu Arg Glu Leu Ala Phe
                435                 440                 445
Leu Glu Gly Ala Gln Ser Arg Ala Thr Ala Ile Leu Gln Arg Ala Asn
                450                 455                 460
Met Val Ala Asn Pro Ala Trp Arg Ser Leu Glu Met Thr Pro Leu Leu
465                 470                 475                 480
His Pro Pro Leu Glu Glu Ile Ala Ala Ile Leu Ala Arg Leu Gly
                485                 490                 495
```

(2) INFORMATION FOR SEQ ID NO:23:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Met Gln Thr Leu Ser Ile Gln His Gly Thr Leu Val Thr Met Asp Gln

-continued

```
1               5                    10                   15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
                35                  40                  45

Arg Val Ile Asp Ala Arg Gly Lys Val Val Leu Pro Gly Phe Ile Asn
 50                 55                  60

Ala His Thr His Val Asn Gln Ile Leu Leu Arg Gly Gly Pro Ser His
 65                 70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
               100                 105                 110

Ala Glu Ala Val Arg Ser Gly Ile Thr Thr Ile Asn Glu Asn Ala Asp
               115                 120                 125

Ser Ala Ile Tyr Pro Gly Asn Ile Glu Ala Ala Met Ala Val Tyr Gly
 130                135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
                195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys His Gly Leu Leu Asp Glu Arg Leu
                260                 265                 270

Gln Val Ala His Cys Val Tyr Phe Asp Arg Lys Asp Val Arg Leu Leu
                275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Met Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
                355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430
```

```
Glu Asn Arg Arg Leu Ser Phe Leu Pro Pro Glu Arg Glu Leu Ala Phe
        435                 440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu Glu Met Thr Pro Leu Leu
465                 470                 475                 480

His Pro Pro Pro Leu Glu Glu Ile Ala Ala Ile Leu Ala Arg Leu Gly
                485                 490                 495
```

(2) INFORMATION FOR SEQ ID NO:24:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Phe Tyr Asp Trp Leu Phe Asn Val Val Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
    130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285
```

```
His Arg His Asn Val Lys Val Ala Ser Gln Val Ser Asn Ala Tyr
    290             295                 300

Leu Gly Ser Gly Val Ala Pro Val Pro Glu Met Val Glu Arg Gly Met
305             310              315                 320

Ala Val Gly Ile Gly Thr Asp Asn Gly Asn Ser Asn Asp Ser Val Asn
            325             330              335

Met Ile Gly Asp Met Lys Phe Met Ala His Ile His Arg Ala Val His
            340             345             350

Arg Asp Ala Asp Val Leu Thr Pro Glu Lys Ile Leu Glu Met Ala Thr
        355             360             365

Ile Asp Gly Ala Arg Ser Leu Gly Met Asp His Glu Ile Gly Ser Ile
370             375             380

Glu Thr Gly Lys Arg Ala Asp Leu Ile Leu Leu Asp Leu Arg His Pro
385             390             395             400

Gln Thr Thr Pro His His His Leu Ala Ala Thr Ile Val Phe Gln Ala
            405             410             415

Tyr Gly Asn Glu Val Asp Thr Val Leu Ile Asp Gly Asn Val Val Met
            420             425             430

Glu Asn Arg Arg Leu Ser Phe Leu Pro Pro Glu Arg Glu Leu Ala Phe
        435             440             445

Leu Glu Glu Ala Gln Ser Arg Ala Thr Ala Ile Leu Gln Arg Ala Asn
450             455             460

Met Val Ala Asn Pro Ala Trp Arg Ser Leu Glu Met Thr Pro Leu Leu
465             470             475             480

His Pro Leu Pro Leu Glu Glu Ile Ala Ala Ile Leu Ala Arg Leu Gly
            485             490             495

(2) INFORMATION FOR SEQ ID NO:25:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
            35                  40                  45

Gln Val Ile Asp Ala Arg Gly Lys Val Val Leu Pro Gly Phe Ile Asn
50              55                  60

Ala His Thr His Val Asn Gln Ile Leu Leu Arg Gly Gly Pro Ser His
65              70                  75                  80

Gly Arg Gln Phe His Asp Trp Leu Phe Asn Val Val Tyr Pro Gly Gln
            85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Glu Asn Ala Asp
        115                 120                 125

Ser Ala Ile Tyr Pro Gly Asn Ile Glu Ala Ala Met Ala Val Tyr Gly
130                 135                 140
```

```
Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
            165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Gly Arg Ile His Gly Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
        290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu Glu Met Thr Pro Leu Leu
465                 470                 475                 480

His Pro Pro Pro Leu Glu Glu Ile Ala Ala Ile Leu Ala Arg Leu Gly
                485                 490                 495
```

(2) INFORMATION FOR SEQ ID NO:26:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

-continued

```
Met Gln Thr Leu Ser Ile Gln His Gly Thr Leu Val Thr Met Asp Gln
 1               5                  10                 15

Tyr Arg Arg Val Leu Gly Asp Ser Trp Val His Val Gln Asp Gly Arg
                20                  25                 30

Ile Val Ala Leu Gly Val His Ala Glu Ser Val Pro Pro Pro Ala Asp
                35                  40                 45

Arg Val Ile Asp Ala Arg Gly Lys Val Val Leu Pro Gly Phe Ile Asn
            50                  55                 60

Ala His Thr His Val Asn Gln Ile Leu Leu Arg Gly Gly Pro Ser His
 65                  70                  75                 80

Gly Arg Gln Phe Tyr Asp Trp Leu Phe Asn Val Val Tyr Pro Gly Gln
                    85                  90                 95

Lys Ala Met Arg Pro Glu Asp Val Ala Val Ala Val Arg Leu Tyr Cys
                100                 105                110

Ala Glu Ala Val Arg Ser Gly Ile Thr Thr Ile Asn Glu Asn Ala Asp
                115                 120                125

Ser Ala Ile Tyr Pro Gly Asn Ile Glu Ala Ala Met Ala Val Tyr Gly
            130                 135                140

Glu Val Gly Val Arg Val Val Tyr Ala Arg Met Phe Phe Asp Arg Met
145                 150                 155                160

Asp Arg Arg Ile Gln Gly Tyr Val Asp Ala Leu Lys Ala Arg Ser Pro
                    165                 170                175

Gln Val Glu Leu Cys Ser Ile Met Glu Glu Thr Ala Val Ala Lys Asp
                180                 185                190

Arg Ile Thr Ala Leu Ser Asp Gln Tyr His Gly Thr Ala Gly Gly Arg
                195                 200                205

Ile Ser Val Trp Pro Ala Pro Ala Thr Thr Thr Ala Val Thr Val Glu
            210                 215                220

Gly Met Arg Trp Ala Gln Ala Phe Ala Arg Asp Arg Ala Val Met Trp
225                 230                 235                240

Thr Leu His Met Ala Glu Ser Asp His Asp Glu Arg Ile His Gly Met
                    245                 250                255

Ser Pro Ala Glu Tyr Met Glu Cys Tyr Gly Leu Leu Asp Glu Arg Leu
                260                 265                270

Gln Val Ala His Cys Val Tyr Phe Asp Arg Lys Asp Ile Arg Leu Leu
                275                 280                285

His Arg His Asn Val Lys Val Ala Ser Gln Ala Val Ser Asn Ala Tyr
                    290                 295                300

Leu Gly Ser Gly Val Ala Pro Val Pro Glu Met Val Glu Arg Gly Met
305                 310                 315                320

Ala Val Gly Ile Gly Thr Asp Asn Gly Asn Ser Asn Asp Ser Val Asn
                    325                 330                335

Met Ile Gly Asp Met Lys Phe Met Ala His Ile His Arg Ala Val His
                340                 345                350

Arg Asp Ala Asp Val Leu Thr Pro Glu Lys Ile Leu Glu Met Ala Thr
                355                 360                365

Ile Asp Gly Ala Arg Ser Leu Gly Met Asp His Glu Ile Gly Ser Ile
            370                 375                380

Glu Thr Gly Lys Arg Ala Asp Leu Ile Leu Leu Asp Leu Arg His Pro
385                 390                 395                400

Gln Thr Thr Pro His His Leu Ala Ala Thr Ile Val Phe Gln Ala
                405                 410                415
```

-continued

```
Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
            450                 455                 460

Met Val Ala Asn Pro Ala Trp Arg Ser Leu Glu Met Thr Pro Leu Leu
465                 470                 475                 480

His Pro Pro Pro Leu Glu Glu Ile Ala Ala Ile Leu Ala Gln Leu Gly
            485                 490                 495
```